United States Patent
Bergan et al.

(10) Patent No.: US 10,231,949 B2
(45) Date of Patent: *Mar. 19, 2019

(54) INHIBITION OF CANCER CELL MOTILITY

(71) Applicant: Northwestern University, Evanston, IL (US)

(72) Inventors: Raymond C. Bergan, Chicago, IL (US); Karl A. Scheidt, Evanston, IL (US); Li Xu, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/839,322

(22) Filed: Dec. 12, 2017

(65) Prior Publication Data
US 2018/0153853 A1 Jun. 7, 2018

Related U.S. Application Data

(62) Division of application No. 14/935,040, filed on Nov. 6, 2015, now Pat. No. 9,839,625.

(60) Provisional application No. 62/076,297, filed on Nov. 6, 2014.

(51) Int. Cl.
*A61K 31/353* (2006.01)
*A61K 45/06* (2006.01)
*A61K 31/4188* (2006.01)
*A61K 31/167* (2006.01)

(52) U.S. Cl.
CPC .......... *A61K 31/353* (2013.01); *A61K 31/167* (2013.01); *A61K 31/4188* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,312,806 A | 1/1982 | Lambert et al. | |
| 5,216,002 A | 6/1993 | Gidda et al. | |
| 5,238,931 A | 8/1993 | Yoshikawa et al. | |
| 5,294,630 A | 3/1994 | Blake et al. | |
| 5,368,854 A | 11/1994 | Rennick | |
| 5,391,555 A | 2/1995 | Marshall et al. | |
| 5,506,213 A | 4/1996 | Carson et al. | |
| 5,552,439 A | 9/1996 | Panetta | |
| 5,756,449 A | 5/1998 | Anderson et al. | |
| 5,792,795 A | 8/1998 | Buser et al. | |
| 5,834,021 A | 11/1998 | Speiers | |
| 5,888,969 A | 3/1999 | Girten et al. | |
| 5,889,028 A | 3/1999 | Sandborn et al. | |
| 5,932,214 A | 8/1999 | Lobb et al. | |
| 8,481,760 B2 | 7/2013 | Bergan et al. | |
| 8,742,141 B2 | 6/2014 | Bergan et al. | |
| 9,839,625 B2 * | 12/2017 | Bergan .................. | A61K 31/353 |
| 2004/0147597 A1 | 7/2004 | Lin | |
| 2006/0167037 A1 | 7/2006 | Kelly et al. | |
| 2013/0123266 A1 | 5/2013 | Zagury et al. | |
| 2016/0128973 A1 | 5/2016 | Bergan et al. | |

FOREIGN PATENT DOCUMENTS

| | | |
|---|---|---|
| WO | WO 2007/126871 | 11/2007 |
| WO | WO 2010/042933 | 4/2010 |
| WO | WO 2013/090836 | 6/2013 |
| WO | WO 2016/073897 | 5/2016 |

OTHER PUBLICATIONS

Amato et al., Investigation of fluorinated and bifunctionalized 3-phenylchroman-4-one (isoflavanone) aromatase inhibitors. Bioorg Med Chem. Jan. 1, 2014;22(1):126-34.

Andersen et al., Flavanoids: Chemistry, Biochemistry and Applications, (Boca Raton: CRC Press). 2006. 1212 pages.

Avram et al., The pharmacokinetics and bioavailability of prochlorperazine delivered as a thermally generated aerosol in a single breath to volunteers. Clin Pharmacol Ther. Jan. 2009;85(1):71-7.

Barrett et al., SAAM II: Simulation, Analysis, and Modeling Software for tracer and pharmacokinetic studies. Metabolism. Apr. 1998;47(4):484-92.

Bergan et al., Electroporation of synthetic oligodeoxynucleotides: a novel technique for ex vivo bone marrow purging.Blood. Jul. 15, 1996;88(2):731-41.

Binkowski et al., Inferring functional relationships of proteins from local sequence and spatial surface patterns. J Mol Biol. Sep. 12, 2003;332(2):505-26.

Binkowski et al., Protein functional surfaces: global shape matching and local spatial alignments of ligand binding sites. BMC Struct Biol. Oct. 27, 2008;8:45.

Binkowski et al., Protein surface analysis for function annotation in high-throughput structural genomics pipeline. Protein Sci. Dec. 2005;14(12):2972-81.

Breen et al., Endoglin-mediated suppression of prostate cancer invasion is regulated by activin and bone morphogenetic protein type II receptors. PLoS One. Aug. 13, 2013;8(8):e72407.

Catherino et al., Increasing the number of tandem estrogen response elements increases the estrogenic activity of a tamoxifen analogue. Cancer Lett. May 25, 1995;92(1):39-47.

(Continued)

*Primary Examiner* — Michael Barker
(74) *Attorney, Agent, or Firm* — Casimir Jones SC; David W. Staple

(57) ABSTRACT

Provided herein are compositions and methods for inhibiting cancer cell motility and/or metastasis. In particular embodiments, KBU2046 (or an analog thereof) and one or more additional therapies (e.g., cancer therapies (e.g., hormone therapies and chemotherapies) are provided to inhibit cancer cell motility, inhibit metastasis, and/or treat cancer (e.g., prostate cancer, lung cancer, breast cancer, colon cancer, etc.).

6 Claims, 57 Drawing Sheets

Specification includes a Sequence Listing.

(56) References Cited

OTHER PUBLICATIONS

Chavez et al., Protein interactions, post-translational modifications and topologies in human cells. Mol Cell Proteomics. May 2013;12(5):1451-67.
Cobelli et al., Compartmental models: theory and practice using the SAAM II software system. Adv Exp Med Biol. 1998;445:79-101.
Coussens et al., Matrix metalloproteinase inhibitors and cancer: trials and tribulations. Science. Mar. 29, 2002;295(5564):2387-92.
Craft et al., Endoglin inhibits prostate cancer motility via activation of the ALK2-Smad1 pathway. Oncogene. Nov. 8, 2007;26(51):7240-50.
Cuenda et al., SB 203580 is a specific inhibitor of a MAP kinase homologue which is stimulated by cellular stresses and interleukin-1. FEBS Lett. May 8, 1995;364(2):229-33.
Deng et al., Computation of binding free energy with molecular dynamics and grand canonical Monte Carlo simulations. J Chem Phys. Mar. 21, 2008;128(11):115103.
Desai et al., Fumonisins and fumonisin analogs as inhibitors of ceramide synthase and inducers of apoptosis. Biochim Biophys Acta. Dec. 30, 2002;1585(2-3):188-92.
Ding et al., The methodology used to measure differential gene expression affects the outcome.J Biomol Tech. Dec. 2007;18(5):321-30.
Ditchfield et al., Aurora B couples chromosome alignment with anaphase by targeting BubR1, Mad2, and Cenp-E to kinetochores. J Cell Biol. Apr. 28, 2003;161(2):267-80.
Du Manoir et al., Strategies for delaying or treating in vivo acquired resistance to trastuzumab in human breast cancer xenografts. Clin Cancer Res. Feb. 1, 2006;12(3 Pt 1):904-16.
Foster, Developing and testing integrated multicompartment models to describe a single-input multiple-output study using the SAAM II software system. Adv Exp Med Biol. 1998;445:59-78.
Friedl et al., Tumour-cell invasion and migration: diversity and escape mechanisms. Nat Rev Cancer. May 2003;3(5):362-74.
Goedert et al., Activation of the novel stress-activated protein kinase SAPK4 by cytokines and cellular stresses is mediated by SKK3 (MKK6); comparison of its substrate specificity with that of other SAP kinases. EMBO J. Jun. 16, 1997;16(12):3563-71.
Graves et al., Rescoring docking hit lists for model cavity sites: predictions and experimental testing. J Mol Biol. Mar. 28, 2008;377(3):914-34.
Guest et al., Drugs that induce neutropenia/agranulocytosis may target specific components of the stromal cell extracellular matrix. Med Hypotheses. Aug. 1999;53(2):145-51.
Hauf et al., The small molecule Hesperadin reveals a role for Aurora B in correcting kinetochore-microtubule attachment and in maintaining the spindle assembly checkpoint. J Cell Biol. Apr. 28, 2003;161(2):281-94.
Herberich et al., Discovery of highly selective and potent p38 inhibitors based on a phthalazine scaffold. J Med Chem. Oct. 23, 2008;51(20):6271-9.
Huang et al., Genistein inhibits p38 MAP kinase activation, MMP-2, and cell invasion in human prostate epithelial cells. Cancer Res. Apr. 15, 2005;65(8):3470-8.
Jackson et al., Pharmacological effects of SB 220025, a selective inhibitor of P38 mitogen-activated protein kinase, in angiogenesis and chronic inflammatory disease models. J Pharmacol Exp Ther. Feb. 1998;284(2):687-92.
Jiang et al., Computation of Absolute Hydration and Binding Free Energy with Free Energy Pe11urbation Distributed Replica-Exchange Molecular Dynamics (FEPIREMD). J Chem Theory Comput. Oct. 1, 2009;5(10):2583-2588.
Jiang et al., Free Energy Perturbation Hamiltonian Replica-Exchange Molecular Dynamics (FEPIH-REMD) for Absolute Ligand Binding Free Energy Calculations. J Chem Theory Comput. Jul. 1, 2010;6(9):2559-2565.
Kataria et al., The pharmacokinetics of propofol in children using three different data analysis approaches. Anesthesiology. Jan. 1994;80(1):104-22.

Knodell et al., Formulation and application of a numerical scoring system for assessing histological activity in asymptomatic chronic active hepatitis. Hepatology. Sep.-Oct. 1981;1(5):431-5.
Krishna et al., Therapeutic modulation of prostate cancer metastasis. Future Med Chem. Feb. 2014;6(2):223-39.
Krishna et al., A fluorescence-based thermal shift assay identifies inhibitors of mitogen activated protein kinase kinase 4. PLoS One. Dec. 5, 2013;8(12):e81504.
Lakshman et al., Dietary genistein inhibits metastasis of human prostate cancer in mice. Cancer Res. Mar. 15, 2008;68(6):2024-32.
Lang et al., DOCK 6: combining techniques to model RNA-small molecule complexes. RNA. Jun. 2009;15(6):1219-30.
Leaver-Fay et al., ROSETTA3: an object-oriented software suite for the simulation and design of macromolecules. Methods Enzymol. 2011;487:545-74.
Lipinski et al., Experimental and computational approaches to estimate solubility and permeability in drug discovery and development settings. Adv Drug Deliv Rev. Mar. 1, 2001;46(1-3):3-26.
Liu et al., Over expression of endoglin in human prostate cancer suppresses cell detachment, migration and invasion. Oncogene. Nov. 28, 2002;21(54):8272-81.
Lomenick et al., Target identification using drug affinity responsive target stability (DARTS). Proc Natl Acad Sci U S A. Dec. 22, 2009;106(51):21984-9.
Lundgren et al., Protein identification using Sorcerer 2 and SEQUEST. Curr Protoc Bioinformatics Chapter 13, Unit 13.3.1, 21 pages.
Manas et al., Understanding the selectivity of Genistein for human estrogen receptor-beta using X-ray crystallography and computational methods. Structure. Dec. 2004;12(12):2197-207.
Messina et al., Addressing the soy and breast cancer relationship: review, commentary, and workshop proceedings. J Natl Cancer Inst. Sep. 20, 2006;98(18):1275-84.
Modrak et al., Sphingolipid targets in cancer therapy. Mol Cancer Ther. Feb. 2006;5(2):200-8.
Morris et al., AutoDock4 and AutoDockTools4: Automated docking with selective receptor flexibility, J Comput Chem. Dec. 2009;30(16):2785-91.
Neckers et al., Hsp90 molecular chaperone inhibitors: are we there yet? Clin Cancer Res. Jan. 1, 2012;18(1):64-76.
Pavese et al., An orthotopic murine model of human prostate cancer metastasis, J Vis Exp. Sep. 18, 2013;(79):e50873.
Pavese et al., Inhibition of cancer cell invasion and metastasis by Genistein, Cancer Metastasis Rev. Sep. 2010;29(3):465-82.
Polier et al., ATP-competitive inhibitors block protein kinase recruitment to the Hsp90-Cdc37 system, Nat Chem Biol. May 2013;9(5):307-12.
Raclin, Killing tumours by ceramide-induced apoptosis: a critique of available drugs, Biochem J. Apr. 15, 2003;371(Pt 2):243-56.
Reynolds et al., Ceramide synthesis and metabolism as a target for cancer therapy. Cancer Lett. Apr. 8, 2004;206(2):169-80.
Roe et al., The Mechanism of Hsp90 regulation by the protein kinase-specific cochaperone p50(cdc37). Cell. Jan. 9, 2004;116(1):87-98.
Shoemaker, The NCI60 human tumour cell line anticancer drug screen. Nat Rev Cancer. Oct. 2006;6(10):813-23.
Steeg, Tumor metastasis: mechanistic insights and clinical challenges. Nat Med. Aug. 2006;12(8):895-904.
Taipale et al., Quantitative analysis of HSP90-client interactions reveals principles of substrate recognition.Cell. Aug. 31, 2012;150(5):987-1001.
Talmadge et al., AACR centennial series: the biology of cancer metastasis: historical perspective. Cancer Res. Jul. 15, 2010;70(14):5649-69.
Tang et al., Mass spectrometry identifiable cross-linking strategy for studying protein-protein interactions. Anal Chem. Jan. 1, 2005;77(1):311-8.
Vankayalapati et al., Targeting auroral kinase in oncogenesis: a structural bioinformatics approach to target validation and rational drug design. Mol Cancer Ther. Mar. 2003;2(3):283-94.
Vaughan et al., Structure of an Hsp90-Cdc37-Cdk4 complex. Mol Cell. Sep. 1, 2006;23(5):697-707.

(56) References Cited

OTHER PUBLICATIONS

Wang et al., Absolute binding free energy calculations using molecular dynamics simulations with restraining potentials. Biophys J. Oct. 15, 2006;91(8):2798-814.
Weisbrod et al., In vivo protein interaction network identified with a novel real-time cross-linked peptide identification strategy. J Proteome Res. Apr. 5, 2013;12(4):1569-79.
Wells et al., Targeting tumor cell motility as a strategy against invasion and metastasis. Trends Pharmacol Sci. May 2013;34(5):283-9.
Whitesell et al., Inhibiting HSP90 to treat cancer: a strategy in evolution. Curr Mol Med. Nov. 1, 2012;12(9):1108-24.
Wright et al., Structure-activity relationships in purine-based inhibitor binding to HSP90 isoforms. Chem Biol. Jun. 2004;11(6):775-85.
Xu et al., Multiple effects of acetaminophen and p38 inhibitors: towards pathway toxicology. FEBS Lett. Apr. 9, 2008;582(8):1276-82.
Xu et al., Genistein inhibits matrix metalloproteinase type 2 activation and prostate cancer cell invasion by blocking the transforming growth factor beta-mediated activation of mitogen-activated protein kinase-activated protein kinase 2-27-kDa heat shock protein pathway.Mol Pharmacol. Sep. 2006;70(3):869-77.
Xu et al., MEK4 Function, Genistein Treatment, and Invasion of Human Prostate Cancer Cells. J Natl Cancer Inst. Aug. 19, 2009;101(16):1141-55.
Young et al., Pyridinyl imidazole inhibitors of p38 mitogen-activated protein kinase bind in the ATP site. J Biol Chem. May 2, 1997;272(18):12116-21.
Zubriene et al., Thermodynamics of radicicol binding to human Hsp90 alpha and beta isoforms. Biophys Chem. Nov. 2010;152(1-3):153-63.
Zhu et al., Synergistic inhibitory effects by the combination of gefitinib and genistein on NSCLC with acquired drug-resistance in vitro and in vivo. Mol Biol Rep. Apr. 2012;39(4):4971-9.
International Search Report and Written Opinion for PCT/US2015/059543, dated Jan. 26, 2016, 7 pages.
Auyeung et al., Novel anti-angiogenic effects of formononetin in human colon cancer cells and tumor xenograft. Oncol Rep. Dec. 2012;28(6):2188-94.
Teo et al., Synthesis of 3-(p-fluorophenyl)-4-arylchrom-3enes as selective ligands for antiestrogen-binding sites. STN Database Accession No. 1990:440398, 8 pages.
Vantyghem et al., Dietary genistein reduces metastasis in a post-surgical orthotopic breast cancer model. Cancer Res. Apr. 2005 15;65(8):3396-403.
Extended European Search Report for EP15857178, dated May 28, 2018, 11 pages.

\* cited by examiner

FIG. 2C

Effect of KBU2046 and genistein on human prostate cell viability

| | | PC3M | | PC3 | | 1542NPTX | | 1542CPTX | | 1532NPTX | | 1532CPTX | |
|---|---|---|---|---|---|---|---|---|---|---|---|---|---|
| | | mean* | se | mean | se | mean | se | mean | se | mean | se | mean | se |
| IC20 | genistein | 17.5 | 4.2 | 18 | 4.9 | 18.7 | 5.7 | 24.7 | 4.6 | 23 | 9.7 | 30.8 | 12 |
| | KBU2046 | NR | - | NR | - | NR | - | NR | - | NR | - | NR | - |
| IC50 | genistein | 45.3 | 13.5 | 41.7 | 9.2 | NR | - | NR | - | NR | - | NR | - |
| | KBU2046 | NR | - | NR | - | NR | - | NR | - | NR | - | NR | - |
| cell viability at 50 uM | genistein | 46.2 | 6.3 | 39.3 | 9.3 | 80.5 | 4.4 | 77.4 | 1.2 | 66.9 | 5.3 | 71.7 | 5.8 |
| | KBU2046 | 100.2 | 6.1 | 88.1 | 1.4 | 107.4 | 3.8 | 103.5 | 1.3 | 95.3 | 6.2 | 99.4 | 4.8 |

*IC20 and IC50 values are uM, cell viability at 50 uM is percentage of control cells, NR = not reached at 50 uM

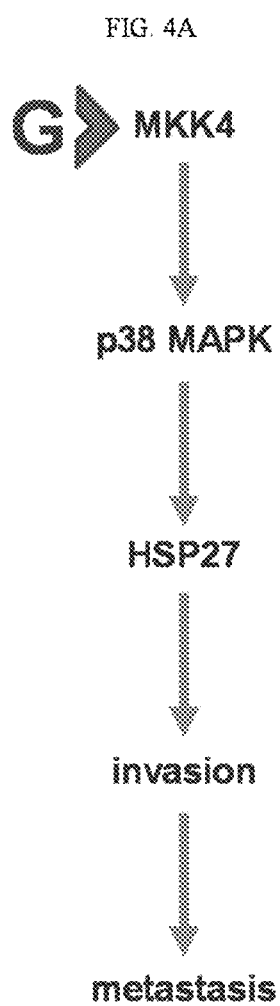
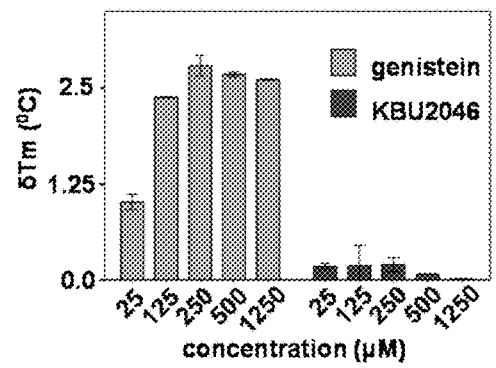
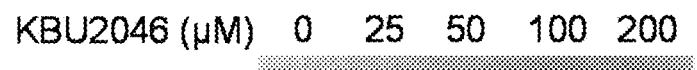
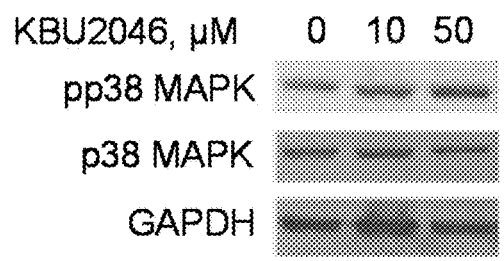
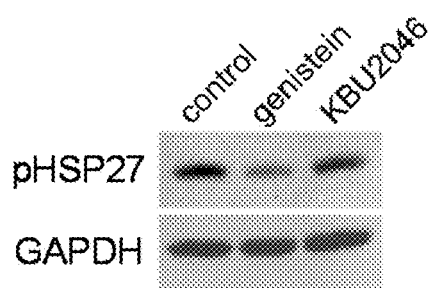
FIG. 4A
FIG. 4B
FIG. 4C
FIG. 4D
FIG. 4E

SEQ ID NO: 18

224EIS*DDEAEEEKGEKEEEDKDDEEKPK249

FIG. 7F
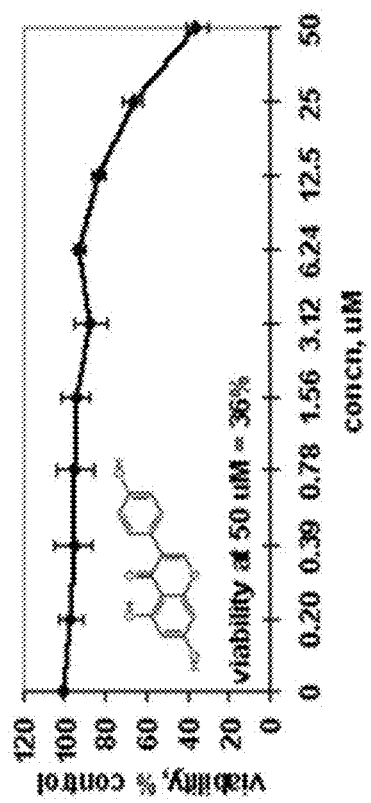
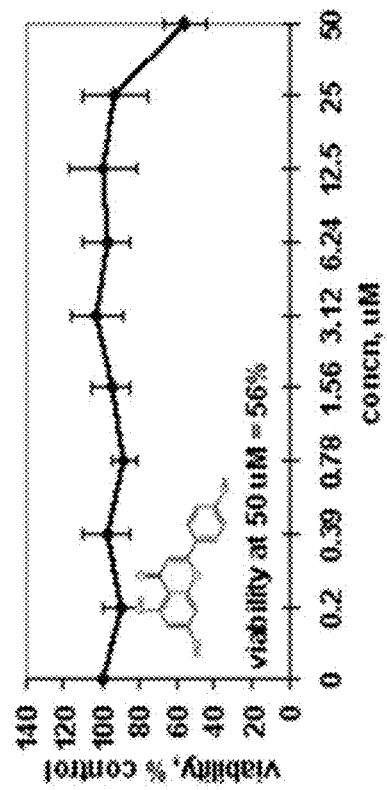

FIG. 7O
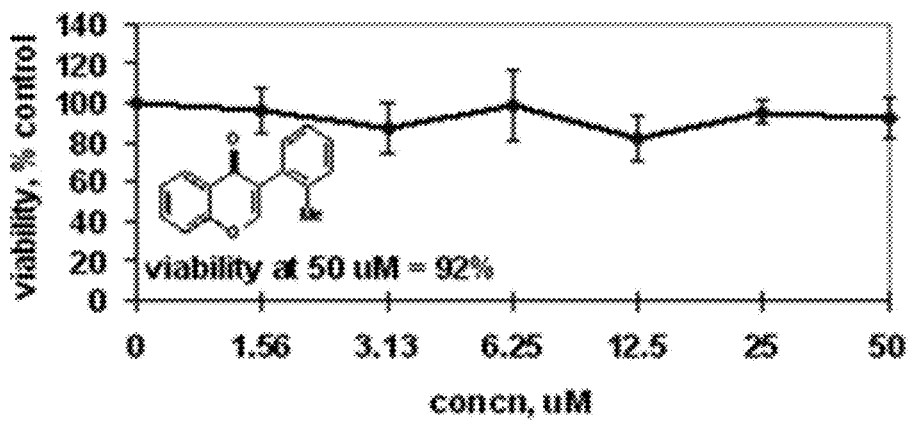
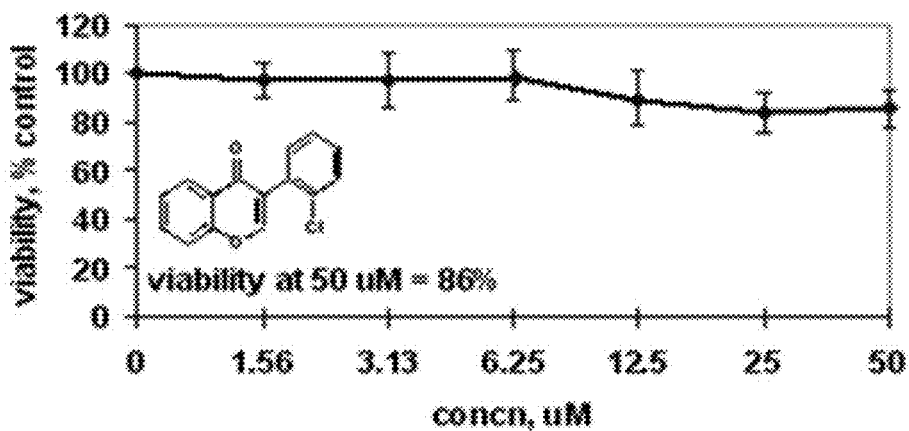
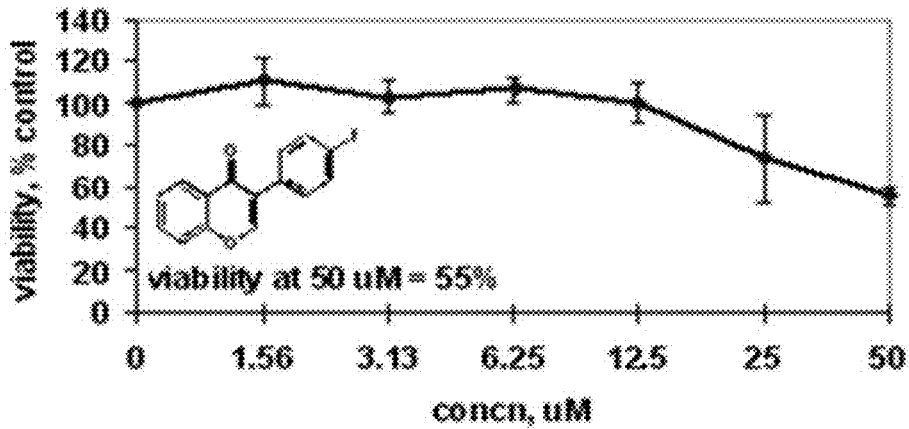

FIG. 7P
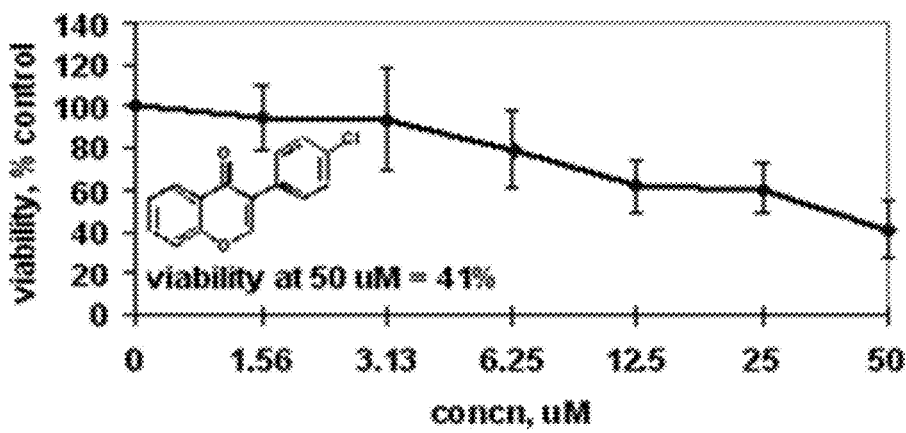
compound 32
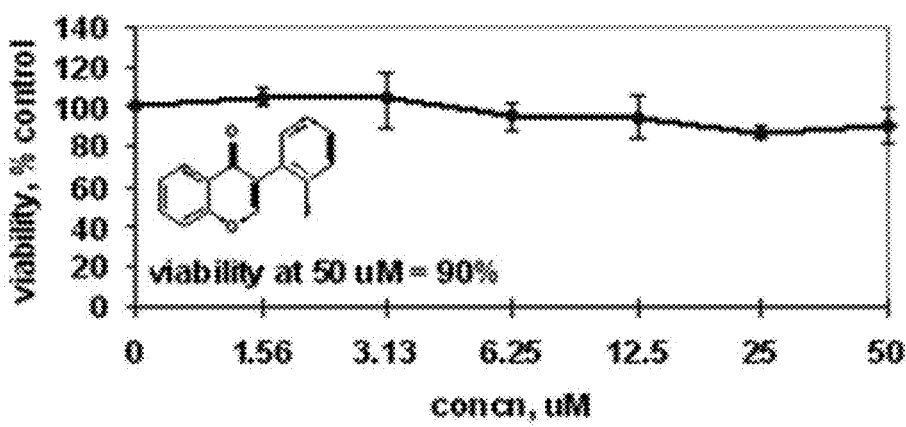
compound 35
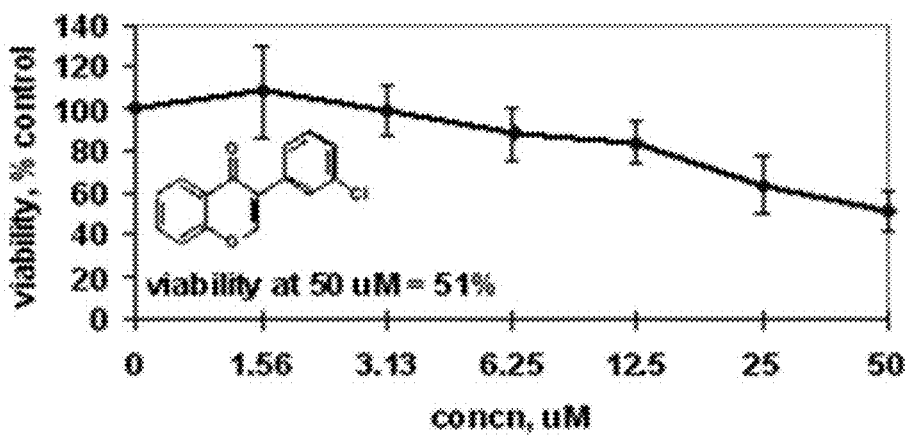
compound 38

FIG. 7S
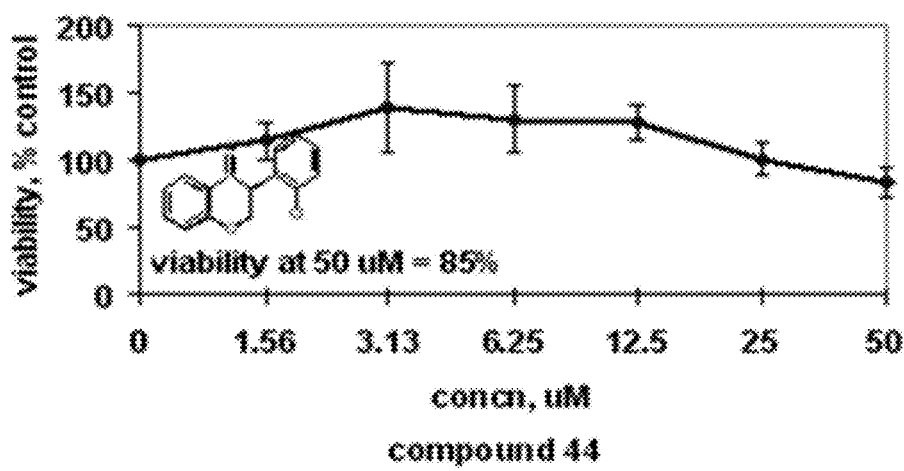
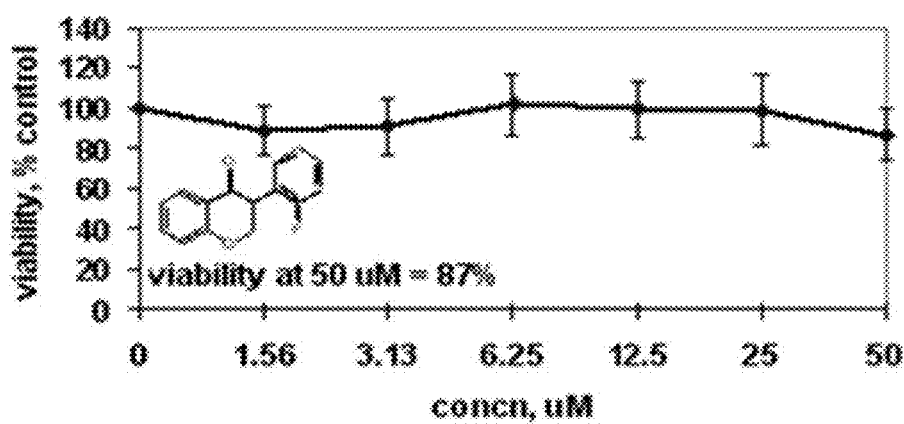
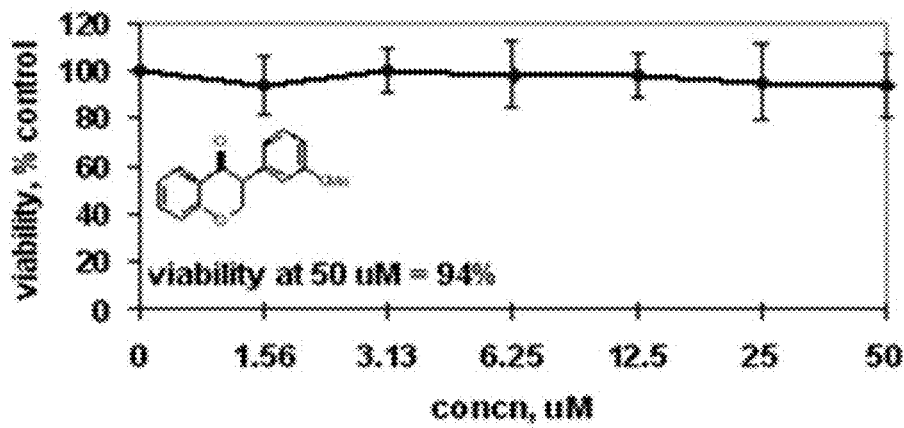

FIG. 7T
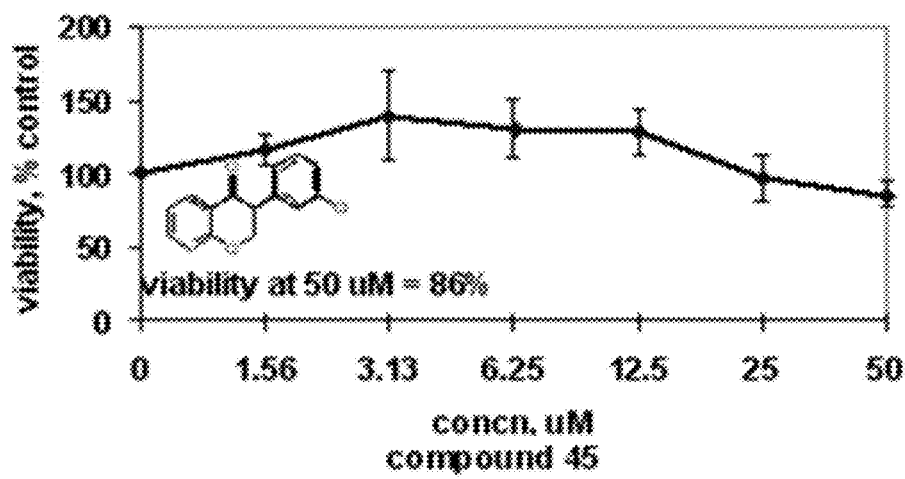
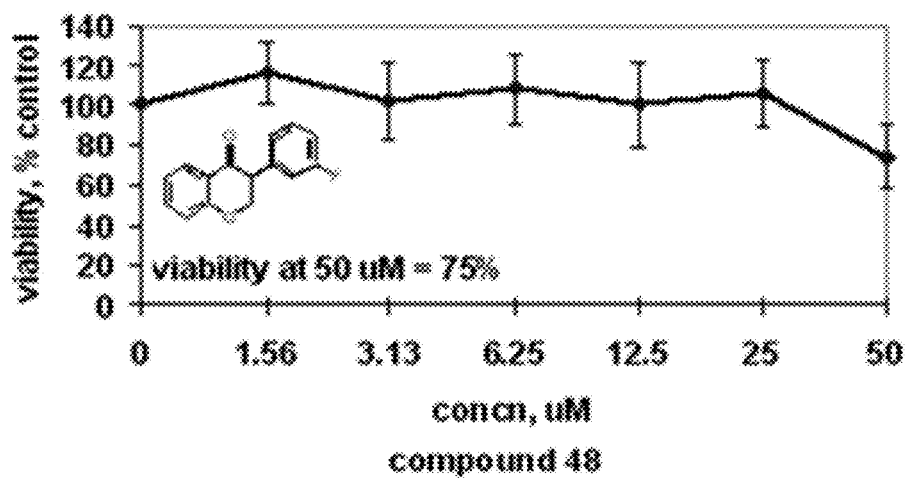
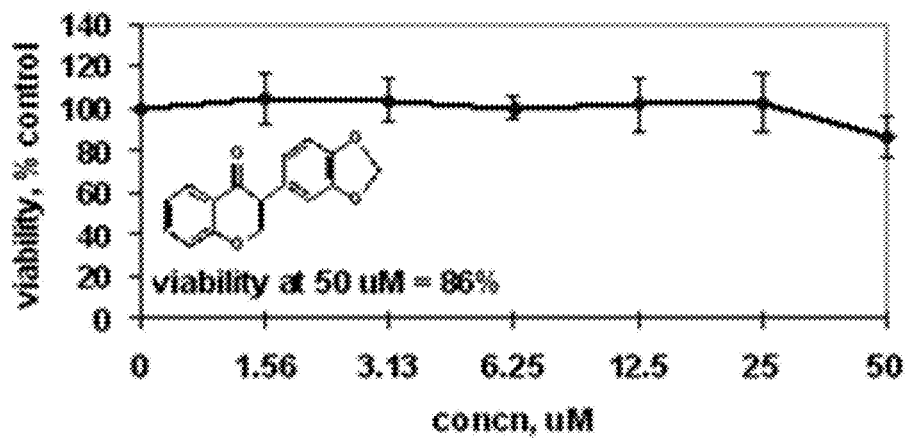

Chemical properties of KBU2046 that are associated with favorable pharmacokinetics

| chemical property | molecular weight | calculated LogP | H-bond donor* | H-bond acceptor |
|---|---|---|---|---|
| recognized as favorable | <500 | <5 | <|= 5 | <|= 10 |
| KBU2046 | 242 | 3.65 | 0 | 2 |

*H-bond: hydrogen bond

FIG. 16

Proteins exhibiting decreased expression with KBU2046

| SEQ ID NO. | Protein | Control | KBU2046 | fold change | MW, kd | Peptide | Protein Type |
|---|---|---|---|---|---|---|---|
| 1 | PGRMC2 | 515487 | 203250 | -2.5 | 24 | LLKPGEEPS*EYT*DEEDTKDHNK | Receptor, channel, transporter or cell surface protein |
| 2 | MrsC | 725332 | 291381 | -2.5 | 38 | NGSLDSPGKDT*EEDEEEDKDKGK | Cytoskeletal protein |
| 3 | CLASP2 | 1467931 | 606085 | -2.4 | 141 | SRS*DIDVNAAAGAK | Cytoskeletal protein |
| 4 | UBL5 | 229589 | 78757 | -2.9 | 9 | CNT*DGTIGDLKK | ubiquitin-like modifier |
| 5 | IWS1 | 221377 | 69168 | -3.2 | 92 | GHHVT*DSENDEPLHLNAS*DSEGEELHR | Transcriptional regulator |
| 6 | SEC62 | 2261192 | 870178 | -2.6 | 46 | VGPGNHGTEGSGGERHS*DT*DSDRR | Receptor, channel, transporter or cell surface protein |
| 7 | SEC62 | 586485 | 213228 | -2.8 | 46 | VGPGNHGTEGS*GGERHS*DTDS*DRR | Receptor, channel, transporter or cell surface protein |
| 8 | RBM5 | 1208222 | 449457 | -2.7 | 92 | SEDGYHS*DGDYGEHDYR | RNA processing |
| 9 | BAT2D1 | 2243885 | 846172 | -2.7 | 317 | S*ES*SDFEVVPK | Cell cycle regulation |
| 10 | PIMT | 568541 | 187146 | -3.0 | 97 | DRPHASGT*DGDES*EEDPPEHKPSK | Transcriptional regulator |
| 11 | FIP1L1 | 2756235 | 949676 | -2.9 | 67 | ERDHS*PTPSVFNS*DEER | RNA processing |
| 12 | RIN | 917304 | 293104 | -3.1 | 243 | HVLS*DLEDDEVR | Cytoskeletal protein |
| 13 | VAMP1 | 332827 | 93333 | -3.6 | 13 | DQKLS*ELDDR | Unknown function |
| 14 | PITSLRE | 2121720 | 647064 | -3.3 | 93 | DLLS*DLQDIS*DSER | Protein kinase, Ser/Thr (non-receptor) |
| 15 | LEO1 | 26743650 | 7928190 | -3.4 | 75 | MGNT*DEEERPQLS*DDER | Transcriptional regulator |
| 16 | PIMT | 330713 | 70551 | -4.7 | 97 | DRPHAS*GT*DGDES*EEDPPEHKPSK | Transcriptional regulator |
| 17 | SSB | 1591561 | 358289 | -4.5 | 47 | TKFAS*DDEHDEHDENGATGPVK | Transcriptional regulator |
| 18 | HSP90B | 1356930 | 204324 | -6.6 | 83 | EIS*DDEAEEEKGKEEEEDKDDEEKPK | Chaperone |
| 19 | MFAP1 | 1970280 | 90214 | -21.8 | 52 | AALDALNT*DDENDEEYEAWK | Unknown function |

Signal intensity of KBU2046-biotin binding to protein microarray

| | | free KBU2046 absent | | free KBU2046 present | | % inhibition by competitor | |
|---|---|---|---|---|---|---|---|
| uniprot ID | name | 0.5 uM | 10 uM | 0.5 uM | 10 uM | 0.5 uM | 10 uM |
| P26440 | Isovaleryl-CoA dehydrogenase | 24040 | 55209 | 4832 | 48376 | 80% | 12% |
| P78347 | General transcription factor II-I | 10702 | 62190 | 3878 | 35455 | 64% | 43% |
| P21291 | cysteine and glycine-rich protein 1 | 5643 | 21624 | 1158 | 14580 | 79% | 33% |

INHIBITION OF CANCER CELL MOTILITY

CROSS-REFERENCE TO RELATED APPLICATIONS

The present application is a divisional of U.S. patent application Ser. No. 14/935,040, filed Nov. 6, 2015, which claims priority to U.S. Provisional Patent Application 62/076,297, filed Nov. 6, 2014, which is incorporated by reference in its entirety.

STATEMENT REGARDING FEDERAL FUNDING

This invention was made with government support under CA122985 awarded by the National Institutes of Health. The government has certain rights in the invention.

FIELD

Provided herein are compositions and methods for inhibiting cancer cell motility and/or metastasis. In particular embodiments, KBU2046 (or an analog thereof) and one or more additional therapies (e.g., cancer therapies (e.g., hormone therapies, chemotherapies) are provided to inhibit cancer cell motility, inhibit metastasis, and/or treat cancer (e.g., prostate cancer, lung cancer, breast cancer, colon cancer, etc.).

BACKGROUND

The movement of cancer cells out of their primary organ of origin greatly reduces the chances of cure (Wells et al., 2013; herein incorporated by reference in its entirety). Increased cell motility is a quintessential characteristic of the metastatic phenotype, represents an initial step in the metastatic cascade, and is absolutely necessary for cancer cells to move from their primary organ of origin to a distant metastatic site (Talmadge and Fidler, 2010; herein incorporated by reference in its entirety). The development of distant metastases is a primary cause of the majority of cancer-associated morbidity and mortality (Minn and Massague, 2008; herein incorporated by reference in its entirety). Processes that drive the development of increased cell motility and metastasis have high potential value as therapeutic targets. However, comprehensive endeavors aimed at selectively inhibiting cancer cell motility and resultant metastasis have met with failure (Coussens et al., 2002; Krishna and Bergan, 2014; Steeg, 2006; herein incorporated by reference in their entireties). While many pathways have been shown to regulate cell motility and metastasis, they constitute pathways whose regulatory effects are pleiotropic (Krishna and Bergan, 2014; herein incorporated by reference in its entirety). It has therefore not been possible to identify regulators of cell motility and metastasis that possess enough selectivity to support their targeted manipulation.

SUMMARY

Provided herein are compositions and methods for inhibiting cancer cell motility and/or metastasis. In particular embodiments, KBU2046 (or an analog thereof) and one or more additional therapies (e.g., cancer therapies (e.g., hormone therapies, chemotherapies) are provided to inhibit cancer cell motility, inhibit metastasis, and/or treat cancer (e.g., prostate cancer, lung cancer, breast cancer, colon cancer, etc.).

Increased cancer cell motility leading to metastasis causes the majority of cancer-related mortality. Using small molecules as biological probes, we demonstrated that KBU2046, bound within a cleft created by HSP90β/CDC37 heterocomplex formation, stabilized that complex, inhibited HSP90β-Ser226 phosphorylation, which in turn was shown to inhibit cancer cell motility. These molecular perturbations led to inhibition of human cancer cell motility in vitro and of metastasis in murine orthotopic models of human prostate and breast cancer metastasis, with effects observed at nanomolar concentrations of KBU2046 after oral administration. Comprehensive molecular, cellular and systemic-based assays demonstrate that probe action is highly selective for inhibition of Ser226 phosphorylation, and resultant effects on cell motility and metastasis.

Experiments conducted during development of embodiments of the present invention demonstrated the inhibition of the movement of human breast, prostate, colon and lung cancer cells. Further, proteins that regulate cancer cell movement were identified, and experiments demonstrate that they are important pharmacologic targets. Further, specific modifications to those proteins have been identified that can be pharmacologically inhibited, and thereby inhibit cell movement. Further, experiments demonstrate that therapeutically inhibiting cancer cell movement can be effectively combined with chemotherapy and hormone therapy, and that this approach improves the effectiveness of hormone therapy for human prostate cancer and can be applied to overcome hormone resistance.

In particular, experiments conducted during development of embodiments described herein demonstrate that the compound KBU2046: inhibits human prostate, breast, colon and breast cancer cell motility, inhibits human prostate and breast cancer metastasis, decreases phosphorylation of serine 226 on HSP90 β, inhibits cell invasion, and increases binding of HSP90 to CDC37. Together, these findings demonstrate the HSP90 function can be altered through these manipulations. This approach to altering HSP90 function enhances the efficacy of hormone therapy for treatment of cancer (e.g., prostate cancer, etc.). This approach to altering HSP90 function does not inhibit the efficacy of cytotoxic cancer therapy; rather, data indicates that additive action and their separate acting mechanisms provide systemic synergy of therapies.

Experiments were conducted during development of embodiments described herein that demonstrate that small molecules can effectively probe the complex biology of cancer cell motility and metastasis. Through this approach, phosphorylation of $Ser^{226}$ on HSP90β has been identified as a regulator of cancer cell motility. Its importance as a pharmacologically modifiable regulator of that process has also been demonstrated. In addition, a small molecule probe that selectively inhibits $Ser^{226}$ phosphorylation has been developed, which in turn selectively inhibits cell motility and metastasis. Further, stabilization of the CDC37/HSP90β heterocomplex using a small molecule has been demonstrated. Together, the experiments conducted during development of embodiments described herein have elucidated a selective and chemically modifiable regulatory mechanism of a critical biological process directly linked to cancer metastasis and its associated high morality.

A significant body of evidence directly supports our proposed model of KBU2046 binding within a cleft formed by the binding of CDC37 to HSP90β, as depicted in FIGS.

6B, 6C, 6D and FIG. 20. This includes the facts that KBU2046 does not bind to either CDC37 or HSP90β separately, and only provides physical stabilization when both CDC37 and HSP90β are present. Further, a comprehensive analysis of structural and biophysical information, described in FIGS. 6B, 6C, 6D and FIG. 20, indicates the formation of a cleft in between the two proteins into which KBU2046 can bind without destabilizing stenc interactions. Finally, the function of KBU2046 is completely distinct from that of classic HSP90 inhibitors (Neckers and Workman, 2012; Whitesell et al., 2012; herein incorporated by reference in their entireties), consistent with it binding to a distinct site and thereby exerting distinct function. Specifically, classical HSP90 inhibitors induce cellular cytotoxicity (Neckers and Workman, 2012; Whitesell et al., 2012; herein incorporated by reference in their entireties), whereas this is completely lacking with KBU2046.

The experiments conducted during development of embodiments described herein demonstrate that phosphorylation of HSP90β Ser226 is an important regulator of cell invasion, and that compounds or strategies which modulate the CDC37-HSP90β interface have important biological and potential translational relevance. In some embodiments, KBU2046 or analogues thereof (See, e.g., U.S. Pat. No. 8,481,760 and U.S. Pat. No. 8,481,760 8,742,141; herein incorporated by reference in their entireties) is provided as a cancer treatment, to inhibit cancer cell motility, to inhibit invasion of pre-cancerous lesions, to inhibit metastasis, to decrease phosphorylation of HSP90β Ser226, etc. In some embodiments, KBU2046 or analogues thereof are administered to a subject suffering from one or more cancers (e.g., solid tumor cancers (e.g., prostate, lung, breast, colon, etc.)) alone or with one or more additional therapies (e.g., hormone therapy, chemotherapy, etc.).

Provided herein are methods for inhibiting cancer cell motility, comprising administering to a subject having cancer a compound having formula of:

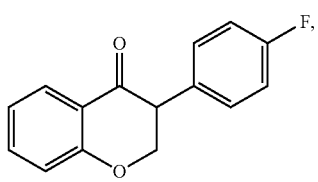 [SMILES: O=C1c2ccccc2OCC1c1ccc(F)cc1]

or analogs thereof. In some embodiments, the subject is a human. In some embodiments, the cancer is a solid tumor cancer. In some embodiments, the cancer is selected from the list consisting of prostate, lung, colon, and breast. In some embodiments, the compound is administered prior to surgical removal of a tumor. In some embodiments, the compound is administered after surgical removal of a tumor. In some embodiments, the compound is co-administered with a second cancer therapeutic agent. In some embodiments, the second cancer therapeutic agent is a hormone therapy agent. In some embodiments, the second cancer therapeutic agent is a chemotherapeutic agent. In some embodiments, the administration inhibits metastasis.

In some embodiments, provided herein are methods for treating a subject suffering from cancer and/or inhibiting cancer cell motility, comprising administering to a subject having cancer a compound having formula of:

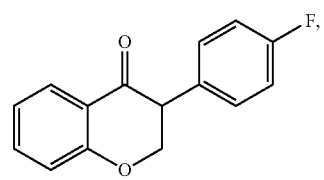 [SMILES: O=C1c2ccccc2OCC1c1ccc(F)cc1]

or analogs thereof, to a subject suffering from colon, lung, or breast cancer. In some embodiments, the compound is administered prior to surgical removal of a tumor. In some embodiments, the compound is administered after surgical removal of a tumor. In some embodiments, the compound is co-administered with a second cancer therapeutic agent. In some embodiments, the second cancer therapeutic agent is a hormone therapy agent. In some embodiments, the second cancer therapeutic agent is a chemotherapeutic agent. In some embodiments, the administration inhibits metastasis.

In some embodiments, provided herein are methods of treating a subject suffering from cancer and/or inhibiting cancer cell motility, comprising co-administering: (a) a compound having formula of:

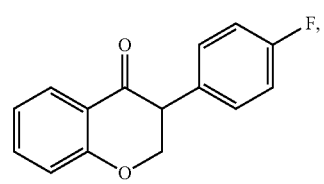 [SMILES: O=C1c2ccccc2OCC1c1ccc(F)cc1]

or analogs thereof, and (b) a hormone therapy agent. In some embodiments, the subject suffers from prostate cancer, colon cancer, lung cancer, or breast cancer. In some embodiments, the hormone therapy agent is selected from the list consisting of flutamide, bicalutamide, nilutamide, enzaluatmide, lupron, zoladex, orchiectomy, abiraterone, tamoxifen, raloxifene, anastrozole, fulvestrant, exemestane, letrozole. In some embodiments, (a) and (b) are administered sequentially. In some embodiments, (a) and (b) are administered simultaneously. In some embodiments, (a) and (b) are co-formulated.

In some embodiments, provided herein are compositions comprising a co-formulation of: (a) a compound having formula of:

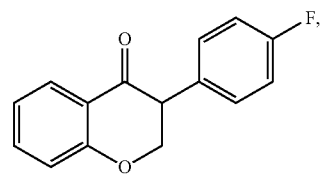 [SMILES: O=C1c2ccccc2OCC1c1ccc(F)cc1]

or analogs thereof, and (b) a hormone therapy agent. In some embodiments, the hormone therapy agent is selected from the list consisting of flutamide, bicalutamide, nilutamide, enzaluatmide, lupron, zoladex, orchiectomy, abiraterone, tamoxifen, raloxifene, anastrozole, fulvestrant, exemestane, letrozole.

In some embodiments, provided herein are compositions comprising a compound having formula of:

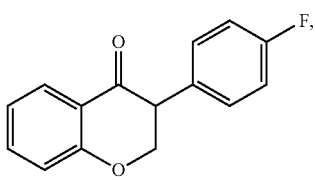 [SMILES: O=C1c2ccccc2OCC1c1ccc(F)cc1]

or analogs thereof, linked to a functional moiety via a linker moiety. In some embodiments, compositions comprise a compound having formula of:

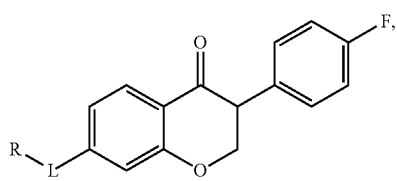

wherein L is a linker moiety and R is a functional moiety. In some embodiments, the functional moiety is selected from the list consisting of: an antibody or a fragment thereof, an affinity tag, a peptide or protein, an oligonucleotide, a solid support, a drug, a metal coordinating group, a contrast agent, a nanoparticle, a cross-linking group, biotin, a fluorophore, and an immunogenic molecule. Other exemplary functional moieties for use in the embodiments herein include, but are not limited to: amino acids (e.g., a naturally occurring amino acid or a non-natural amino acid), a peptide or polypeptide (protein) including an antibody or a fragment thereof, a His-tag, a FLAG tag, a Strep-tag, an enzyme, a cofactor, a coenzyme, a peptide or protein substrate for an enzyme (e.g., branched peptide substrate (e.g., Z-aminobenzoyl (Abz)-Gly-Pro-Ala-Leu-Ala-4-nitrobenzyl amide (NBA), etc.), a suicide substrate, a receptor, one or more nucleotides (e.g., ATP, ADP, AMP, GTP or GDP) including analogs thereof, an oligonucleotide (e.g., a double stranded or single stranded DNA), a glycoprotein, a polysaccharide, a peptide-nucleic acid (PNA), a solid support (e.g., a sedimental particle such as a magnetic particle, a sepharose or cellulose bead, a membrane, glass (e.g., glass slides), cellulose, alginate, plastic or other synthetically prepared polymer (e.g., an eppendorf tube or a well of a multi-well plate), self-assembled monolayers, a surface plasmon resonance chip, or a solid support with an electron conducting surface), a drug (e.g., a chemotherapeutic such as doxorubicin, 5-fluorouracil, or camptosar (CPT-11; Irinotecan), etc.), a pH sensitive agent, a radionuclide, a molecule which is electron opaque, a contrast agent (e.g., barium, iodine or other MM or X-ray contrast agent), a molecule which is sensitive to a reactive oxygen, a nanoparticle (e.g., an immunogold particle, paramagnetic nanoparticle, upconverting nanoparticle, or a quantum dot), a nonprotein substrate for an enzyme, an inhibitor of an enzyme, a chelating agent, a cross-linking group (e.g., a succinimidyl ester or aldehyde, glutathione, etc.), biotin or other avidin binding molecule, avidin, streptavidin, cAMP, phosphatidylinositol, heme, a ligand for cAMP, a metal, one or more dyes (e.g., a xanthene dye, a calcium sensitive dye, a sodium sensitive dye, a NO sensitive dye, or other fluorophore), a hapten or an immunogenic molecule (e.g., one which is bound by antibodies specific for that molecule), a radionuclide (e.g., 0.3H, 14C, 35S, 125I, 131I, etc). In some embodiments, the linker moiety comprises a straight or branched chain of 1-30 carbon atoms, optionally comprising one or more heteroatoms and branched or main-chain substituents. In some embodiments, the linker moiety comprises a multiatom straight or branched chain of atoms selected from C, H, N, O, P, and S. functional groups comprising the linker moiety include, but are not limited to —$CH_2$—, =CH—, =C=, CO, CONH, —$NH_2$, —OH, —SH, —O—, —S—, etc. In some embodiments, the linker moiety comprises one or more $(CH_2)_2O$ groups. In some embodiments, the linker moiety comprises one or more CONH groups. In some embodiments, the linker moiety comprises $(CH_2)_2CONH[(CH_2)_2O]_2$ or $(CH_2)_4CONH[(CH_2)_2O]_4$. In some embodiments, compositions comprise a compound having formula of:

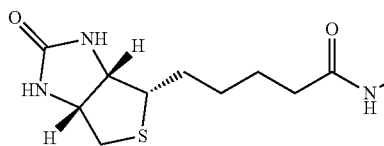

BRIEF DESCRIPTION OF THE DRAWINGS

FIGS. 2A-E. KBU2046 selectively inhibits cell motility. (FIG. 2A) Cell invasion. Human prostate metastatic cells (PC3, PC3-M), and HPV transformed normal (1532NPTX, I542NPTX) and primary cancer (1532CPTX, 1542CPTX) cells, were treated with 10 μM genistein (G), KBU2046 (46) or vehicle (CO), and after 3 days, cell invasion was measured. Values are mean±SEM. (FIG. 2B) Single cell migration. Cell migration was measured after treatment for 3 days with 10 μM KBU2046 or vehicle (control). Values are mean±SEM. *Denotes Student's t test P value </=0.05, compared to controls. (FIG. 2C) Cell growth inhibition. The concentrations at which KBU2046 or genistein inhibited cell growth after 3 days by 20% (IC20) and 50% (IC50) are depicted, as is the percentage of growth inhibition at 50 μM. Values are mean±SEM. (FIG. 2D) Human cord blood hematopoietic stem cell colony formation assay. Values are the mean±SD number of total, CFU-GM, CFU-GEMM or BFU-E colonies at 14 days after treatment with KBU2046, (FIG. 2E) Induction of estrogen responsive genes. Values are the mean±SD.

FIGS. 4A-E. KBU2046 does not inhibit the MKK4 pathway. (A) Depiction of established MKK4 pathway regulating human PCa cell metastasis. (B) KBU2046 does not bind to MKK4, as measured by fluorescence-based thermal shift assay. Values are the mean±SD increase in melting temperature (ΔTm) of purified recombinant MKK4 induced by the indicated concentrations of KBU2046 or genistein. (C) KBU2046 does not inhibit MKK4 in an in vitro kinase assay. The indicated concentrations of KBU2046 were added to recombinant activated MKK4, and its ability to phosphorylate kinase dead p38a MAPK (K53A) was measured by Western blot for total (p38 MAPK) and phosphorylated (pp38 MAPK) forms of p38 MAPK. (D, E) KBU2046 does not inhibit downstream phosphorylation of p38 MAPK or of HSP27 in cells. PC3-M cells were pre-treated for 24 hours with 50 μM KBU2046 or genistein, as indicated, then with TGFβ, and Western blot performed.

FIGS. 7A-H. Synthetic round #1. As this scaffold had anti-invasion efficacy, it was first evaluated which of its chemical fragments were necessary for activity by synthesizing a set of compounds lacking individual functional groups, and assessing their effects upon cell invasion and cell growth inhibition. Informative findings include: the ring C4'-hydroxyl group is necessary for activity (compare compounds 1 and 2) and removal of the C7•hydroxyl group (which mediates binding to the ER) does not affect activity (compare compounds 2 and 8). Other relevant findings: movement of the C4'-hydroxyl is associated with retention of activity (compare compounds 2 and 5), and it is possible to achieve growth inhibition while having minimal impact upon invasion; consider compounds 1, 3, 4, and 6. Demethylation within the cell cannot be predicted. Therefore, loss of function was only considered to be informative for methylated compounds. For example, compound 7, where methylation of the C4'•hydroxyl group leads to loss of invasion (e.g., compared to compound 8). This further evidences the importance of the C4'-hydroxyl for activity. In contrast, while the C7- and C4'-hydroxyl groups of compound 16 are methylated, it retains anti-invasion activity, indicating that demethylation within the cell could possibly influence the results. For cell invasion, PC3-M cells were treated with 10 compound for a total of 3 days, and cell invasion assays were run at the end of the 3 day period, in the presence of compound. Values are the mean±SEM. Three day MTT cell growth inhibition assays were performed with PC3-M cells. Values are the mean±SEM.

FIGS. 7N-Q. Synthetic round #3. Substitution of the C4'-hydroxyl group with a halide is associated with maintenance of activity (compounds 37 and 38). A chemical entity is with potent anti-invasive effects, but which still retains growth inhibitory effects is identified (compound 38).

FIGS. 7R-U. Synthetic round #4KBU2046 (compound 46), has been identified with anti-invasive efficacy at least equal to that of the starting compound, 4',5,7-trihydroxyisoflavone, but that has no growth inhibitory effects. Compared to 4',5,7-trihydroxyisoflavone, KBU2046 is non-planar, lacks hydroxyl groups, and particularly those that mediate ER binding, is halogen-substituted, and has a distinctly different biological profile. These characteristics place KBU2046 in a chemically distinct class, compared to the starting compound.

FIG. 16. Identification of the 83 kDa band using a proteomic approach. PC3 cells were pre-treated with 10 μM KBU2046 or vehicle (control) for 3 days, then treated with TGFβ for 1 hr, and the resultant cell lysates were subjected to immunoprecipitation with BL4176 (Kinoview® phospho-motif antibody). Proteins bound in this manner were analyzed using PhosphoScan™ technology. This identified 483 unique phosphopeptide assignments from 306 parent proteins, with a mean false discovery rate of 0.30% (estimated via Sorcerer search of composite human database of forward and reverse protein entries). Only proteins where the average values for treatment and control were each 3 times that of background were considered. Further, it was required that each of the replicate values (used to calculate the average) to be >/=2.5 fold above background. According to these parameters, there were 19 phospho-proteins whose expression decreased in cells treated with KBU2046, compared to control.

DEFINITIONS

Figure 1:
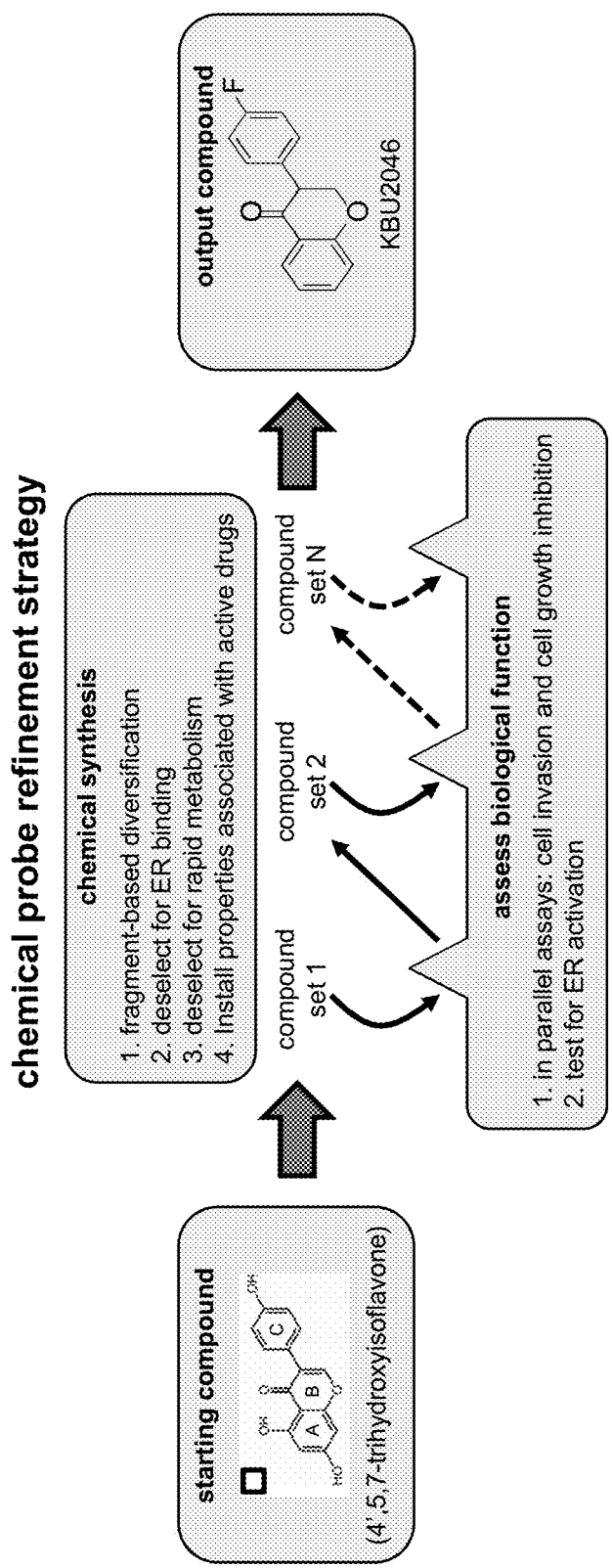
FIG. 1. Schematic flow of exemplary probe development strategy. Beginning with 4',5,7-trihydroxyisoflavone (genistein) as a chemical scaffold, a fragment-based chemical diversification synthesis approach was followed, and coupled in an iterative fashion to biological assays of cell invasion and cell growth inhibition. Compounds that inhibited cell invasion but did not inhibit cell growth were selected for further modification and evaluation. The initial round of synthesis was designed to examine the removal of individual chemical fragments. In this manner, the importance of these functional groups in mediating efficacy (inhibition of cell invasion) was determined. Subsequent rounds built upon refined structure activity relationship (SAR) knowledge, and sought to improve efficacy, while deselecting for toxicity (cell growth inhibition). Initial assays were performed with PC3 and PC3-M cells. However, as these studies yielded similar findings, subsequent screening assays utilized only PC3-M cells. In designing chemical synthetic routes, priority was given to efficacy and toxicity parameters. Additional design features were also included in our chemical synthetic routes, but they were only incorporated if they did not compromise efficacy and toxicity parameters. These additional design features included removal of fragments that mediated genistein binding to the estrogen receptor (ER), as determined by ER-genistein 3D x-ray crystal structures (protein Data Base IDs: 1X7R and IX7J, for crystal structures of ERα and ERβ with bound genistein, respectively). These features also included removal of chemical fragments that are considered to increase susceptibility to rapid metabolism, especially that by the cytochrome P450 (CYF) pathway. The final feature involved incorporation of chemical characteristics previously shown to be associated with effective drugs and which together generally impart more favorable pharmacologic properties, including those described by Lipinski et al. (Lipinski et al., 2001; herein incorporated by reference in its entirety).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and/or molecular screening tests.

As used herein, the term "initial diagnosis" refers to a test result of initial cancer diagnosis that reveals the presence or absence of cancerous cells (e.g., using a biopsy and histology).

As used herein, the term "tumor tissue" refers to a cancerous tissue within a subject and may be further designated as "prostate tumor tissue," "lung tumor tissue," "breast tumor tissue," etc., according to the location of origin of the cells within the tumor. In some embodiments, the tumor tissue is "post-surgical tumor tissue," which refers to cancerous tissue that has been removed from a subject (e.g., during surgery).

As used herein, the term "identifying the risk of said tumor metastasizing" refers to the relative risk (e.g., the percent chance or a relative score) of a tumor metastasizing.

As used herein, the term "identifying the risk of said tumor recurring" refers to the relative risk (e.g., the percent chance or a relative score) of a tumor recurring in the same organ as the original tumor.

As used herein, the term "subject at risk for cancer" refers to a subject with one or more risk factors for developing a specific cancer. Risk factors include, but are not limited to, gender, age, genetic predisposition, environmental exposure, and previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue and the stage of the cancer.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ). Several staging methods are commonly used.

As used herein, the term "characterizing tissue in a subject" refers to the identification of one or more properties of a tissue sample (e.g., including but not limited to, the presence of cancerous tissue, the presence of pre-cancerous tissue that is likely to become cancerous (such as prostatic intraepithelial neoplasia, or PIN), and the presence of cancerous tissue that is likely to metastasize).

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present invention.

DETAILED DESCRIPTION

Provided herein are compositions and methods for inhibiting cancer cell motility and/or metastasis. In particular embodiments, KBU2046 (or an analog thereof) and one or more additional therapies (e.g., cancer therapies (e.g., hormone therapies) are provided to inhibit cancer cell motility, inhibit metastasis, and/or treat cancer (e.g., prostate cancer, lung cancer, breast cancer, colon cancer, etc.).

In some embodiments, provided herein are therapeutic compositions comprising one or more agents for inhibiting cell motility and/or metastasis (e.g., KBU2046). In some embodiments, methods are provided of treating cancer, inhibiting cancer cell motility, inhibiting metastasis, prolonging human life etc. through the administration of such compounds (or co-administration).

In addition, agents described herein (e.g., KBU2046, and analogs thereof) may be used together with other therapeutic agents, including, but not limited to, salicylates, steroids, immunosuppressants, chemotherapeutics, hormone therapy, antibodies or antibiotics. Particular therapeutic agents which may be used include, but are not limited to, the following agents: azobenzene compounds (U.S. Pat. No. 4,312,806, incorporated herein by reference), benzyl-substituted rhodamine derivatives (U.S. Pat. No. 5,216,002, incorporated herein by reference), zinc L-carnosine salts (U.S. Pat. No. 5,238,931, incorporated herein by reference), 3-phenyl-5-carboxypyrazoles and isothiazoles (U.S. Pat. No. 5,294,630, incorporated herein by reference), IL-10 (U.S. Pat. No. 5,368,854, incorporated herein by reference), quinoline leukotriene synthesis inhibitors (U.S. Pat. No. 5,391,555, incorporated herein by reference), 2'-halo-2'deoxy adenosine (U.S. Pat. No. 5,506,213, incorporated herein by reference), phenol and benzamide compounds (U.S. Pat. No. 5,552,439, incorporated herein by reference), tributyrin (U.S. Pat. No. 5,569,680, incorporated herein by reference), certain peptides (U.S. Pat. No. 5,756,449, incorporated herein by reference), omega-3 polyunsaturated acids (U.S. Pat. No. 5,792,795, incorporated herein by reference), VLA-4 blockers (U.S. Pat. No. 5,932,214, incorporated herein by reference), prednisolone metasulphobenzoate (U.S. Pat. No. 5,834,021, incorporated herein by reference), cytokine restraining agents (U.S. Pat. No. 5,888,969, incorporated herein by reference), p38 inhibitors (Herberich et al (2008) J. Med. Chem 10.1021/jm8005417; Cuenda et al (1995) FEBS Lett. 364:229-33; Jackson et al (1998) J. Pharmacol. Exper. Therapeutics 284:687-92; Young et at (1997) J Biol Chem 272:12116-21; Goedert et al (1997) EMBO J 16:3563-71; Buo et al (2005) Bioorg. Medicinal Chem. Lett. 16:64-8; WO/2007/126871; Xu et al (2008) FEBS Lett 8:1276-82; each incorporated herein by reference) and nicotine (U.S. Pat. No. 5,889,028, incorporated herein by reference).

Therapeutic agents (e.g., KBU2046) may be used together with agents which reduce the viability or proliferative potential of a cell. Agents which reduce the viability or proliferative potential of a cell can function in a variety of ways including, for example, inhibiting DNA synthesis, inhibiting cell division, inducing apoptosis, or inducing non-apoptotic cell killing. Specific examples of cytotoxic and cytostatic agents include but are not limited to, pokeweed antiviral protein, abrin, ricin, and each of their A chains, doxorubicin, cisplastin, iodine-131, yttrium-90, rhenium-188, bismuth-212, taxol, 5-fluorouracil VP-16, bleomycin, methotrexate, vindesine, adriamycin, vincristine, vinblastine, BCNU, mitomycin, paclitaxel, docetaxel, cabazitaxel, mitoxantrone and cyclophosphamide and certain cytokines such as TNF-α and TNF-β. Thus, cytotoxic or cytostatic agents can include, for example, radionuclides, chemotherapeutic drugs, proteins, and lectins.

Agents which reduce the viability or proliferative potential of cells which are responsive to hormones, such as prostate and breast cancer, can function in a variety of ways including, for example, inhibiting the production of hormones, including androgens and estrogens, increasing the metabolism of hormones, by antagonizing the action of hormones, and by removing or altering the function of the targets of hormones, especially the hormone receptors and their associated co-regulators. Specific examples of hormonal agents include but are not limited to, flutamide, bicalutamide, nilutamide, enzaluatmide, lupron, zoladex, orchiectomy, abiraterone, tamoxifen, raloxifene, anastrozole, fulvestrant, exemestane, letrozole and ovariectomy.

"Treating" within the context of the instant invention, means an alleviation, in whole or in part, of symptoms associated with a disorder or disease, or slowing, inhibiting or halting of further progression or worsening of those symptoms, or prevention or prophylaxis of the disease or disorder in a subject at risk for developing the disease or disorder. Thus, e.g., treating metastatic cancer may include inhibiting or preventing the metastasis of the cancer, a reduction in the speed and/or number of the metastasis, a reduction in tumor volume of the metastasized prostate cancer, a complete or partial remission of the metastasized prostate cancer or any other therapeutic benefit. As used herein, a "therapeutically effective amount" of a compound of the invention refers to an amount of the compound that alleviates, in whole or in part, symptoms associated with a disorder or disease, or slows, inhibits or halts further progression or worsening of those symptoms, or prevents or provides prophylaxis for the disease or disorder in a subject at risk for developing the disease or disorder.

A therapeutically effective amount of a compound as described herein used in the present invention may vary depending upon the route of administration and dosage form. Effective amounts of invention compounds typically fall in the range of about 0.001 up to 100 mg/kg/day, and more typically in the range of about 0.05 up to 10 mg/kg/day. Typically, the compound or compounds used in the instant invention are selected to provide a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

Treatment may also include administering the compounds or pharmaceutical formulations of the present invention in combination with other therapies. Combinations of the invention may be administered simultaneously, separately or sequentially. For example, the compounds and pharmaceutical formulations of the present invention may be administered before, during, or after surgical procedure and/or radiation therapy. Alternatively, the compounds of the invention can also be administered in conjunction with other anticancer agents described herein. The specific amount of the additional active agent will depend on the specific agent used, the type of condition being treated or managed, the severity and stage of the condition, and the amount(s) of compounds and any optional additional active agents concurrently administered to the subject.

In some embodiments of the invention, one or more compounds (e.g., KBU2046) and an additional active agent (e.g., hormone therapeutic, chemotherapeutic, etc.) are administered to a subject, more typically a human, in a sequence and within a time interval such that the compound can act together with the other agent to provide an enhanced benefit relative to the benefits obtained if they were administered otherwise. For example, the additional active agents can be co-administered by co-formulation, administered at the same time or administered sequentially in any order at different points in time; however, if not administered at the same time, they should be administered sufficiently close in time so as to provide the desired therapeutic or prophylactic effect. In some embodiments, the compound and the additional active agents exert their effects at times which overlap. Each additional active agent can be administered separately, in any appropriate form and by any suitable route. In other embodiments, the compound is administered before, concurrently or after administration of the additional active agents.

In various examples, the compound (e.g., KBU2046) and the additional active agent(s) (e.g., hormone therapeutic, chemotherapeutic, etc.) are administered less than about 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In some embodiments, therapies are administered sequentially, where the separation between administrations is one week or greater (e.g., 1 week, 2 weeks, 1 month, 2 months, 3 months, four months, and ranges therein). For example, five cycles of monthly chemotherapy are administered, followed by treatment with KBU2046 the next month. In other examples, the compound and the additional active agents are administered concurrently. In yet other examples, the compound and the additional active agents are administered concurrently by co-formulation.

In other examples, the compound (e.g., KBU2046) and the additional active agents (e.g., hormone therapeutic, chemotherapeutic, etc.) are administered at about 2 to 4 days apart, at about 4 to 6 days apart, at about 1 week part, at about 1 to 2 weeks apart, or more than 2 weeks apart.

In certain examples, the compound (e.g., KBU2046) and optionally the additional active agents (e.g., hormone therapeutic, chemotherapeutic, etc.) are cyclically administered to a subject. Cycling therapy involves the administration of a first agent for a period of time, followed by the administration of a second agent and/or third agent for a period of time and repeating this sequential administration. Cycling therapy can provide a variety of benefits, e.g., reduce the development of resistance to one or more of the therapies, avoid or reduce the side effects of one or more of the therapies, and/or improve the efficacy of the treatment.

In other examples, the compound (e.g., KBU2046) and optionally the additional active agent (e.g., hormone therapeutic, chemotherapeutic, etc.) are administered in a cycle of less than about 3 weeks, about once every two weeks, about once every 10 days or about once every week. One cycle can comprise the administration of an inventive compound and optionally the second active agent by infusion over about 90 minutes every cycle, about 1 hour every cycle, about 45 minutes every cycle, about 30 minutes every cycle or about 15 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles. In some embodiments, the compound (e.g., KBU2046) is administered daily for an extended period of time (e.g., 6 months, 1 year, 2 years, 3, years, 4 year, 5 years, ranges therein).

Courses of treatment can be administered concurrently to a subject, for example, individual doses of the additional active agents are administered separately yet within a time interval such that the agent (e.g., KBU2046) can work together with the additional active agents (e.g., hormone therapeutic, chemotherapeutic, etc.). For example, one component can be administered once per week in combination with the other components that can be administered once every two weeks or once every three weeks. In other words, the dosing regimens are carried out concurrently even if the therapeutics are not administered simultaneously or during the same day.

The active agent(s) (e.g., KBU2046, hormone therapeutic, chemotherapeutic, etc.) can act additively or, more typically, synergistically. In one example, a first agent (e.g. KBU2046) is administered concurrently with one or more second active agents in the same pharmaceutical composition. In another example, a first agent (e.g. KBU2046) is administered concurrently with one or more second active agents in separate pharmaceutical compositions. In still another example, the inventive compound is administered prior to or subsequent to administration of a second active agent. The invention contemplates administration of an inventive compound and a second active agent by the same or different routes of administration, e.g., oral and parenteral. In certain embodiments, a first agent (e.g. KBU2046) is administered concurrently with a second active agent that potentially produces adverse side effects including, but not limited to, toxicity, the second active agent can advantageously be administered at a dose that falls below the threshold that the adverse side effect is elicited.

In some embodiments, compositions (e.g., comprising KBU2046) are effective at inhibiting or reversing resistance to certain agents, particularly hormonal agents. This relates to the facts that KBU2046 inhibits the function of HSP90β, that HSP90β maintains hormone receptors, particularly the androgen receptor, in an active state, and that several resistance mechanisms involve increasing the expression of the androgen receptor, or the expression of mutated androgen receptor. In both instances, KBU2046 removes active androgen receptor.

In some embodiments, compositions described herein (e.g., KBU2046) are useful for preventing the initial development of cancer, and particularly so in subjects "at risk" for cancer. Its pharmacologic actions would also make it suitable as a cancer prevention agent (e.g., because it inhibits cell invasion). The invasion of cancer cells through the basement membrane of organs they arise from is a requirement for the definition of cancer. Thus, KBU2046 inhibits the initial development of cancer. For example, men with prostatic intraepithelial neoplasia (PIN), have cancer cells present in their prostate glands. Those cells have not yet invaded the basement membrane. Subjects with PIN are at high risk for developing prostate cancer. Once cells invade the basement membrane, the diagnosis changes from PIN to prostate cancer. Another term used for cancer that has not invaded the basement membrane is in situ cancer, or carcinoma in situ (CIS) In situ cancer is seen with prostate, breast (ductal or lobular; DCIS, LCIS), lung, and colon. For each organ, the presence of CIS puts people at high risk for developing invasive cancer.

Provided herein are pharmaceutical compositions and medicaments which may be prepared by combining one or more compounds described herein, pharmaceutically acceptable salts thereof, stereoisomers thereof, tautomers thereof, or solvates thereof, with pharmaceutically acceptable carriers, excipients, binders, diluents or the like to inhibit or treat primary and/or metastatic prostate cancers. Such compositions can be in the form of, for example, granules, powders, tablets, capsules, syrup, suppositories, injections, emulsions, elixirs, suspensions or solutions. Compositions can be formulated for various routes of administration, for example, by oral, parenteral, topical, rectal, nasal, or via implanted reservoir. Parenteral or systemic administration includes, but is not limited to, subcutaneous, intravenous, intraperitoneal, and intramuscular injections. The following dosage forms are given by way of example and should not be construed as limiting.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or antioxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

For rectal administration, the pharmaceutical formulations and medicaments may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Compounds of the invention may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. Formulations for inhalation administration contain as excipients, for example, lactose, polyoxyethylene-9-lauryl ether, glycocholate and deoxycholate. Aqueous and nonaqueous aerosols are typically used for delivery of inventive compounds by inhalation.

Ordinarily, an aqueous aerosol is made by formulating an aqueous solution or suspension of the compound together with conventional pharmaceutically acceptable carriers and stabilizers. The carriers and stabilizers vary with the requirements of the particular compound, but typically include nonionic surfactants (TWEENs, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions. A nonaqueous suspension (e.g., in a fluorocarbon propellant) can also be used to deliver compounds of the invention.

Aerosols containing compounds for use according to the present invention are conveniently delivered using an inhaler, atomizer, pressurized pack or a nebulizer and a suitable propellant, e.g., without limitation, pressurized dichlorodifluoromethane, trichlorofluoromethane, dichlorotetrafluoroethane, nitrogen, air, or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch. Delivery of aerosols of the present invention using sonic nebulizers is advantageous because nebulizers minimize exposure of the agent to shear, which can result in degradation of the compound.

For nasal administration, the pharmaceutical formulations and medicaments may be a spray, nasal drops or aerosol containing an appropriate solvent(s) and optionally other compounds such as, but not limited to, stabilizers, antimicrobial agents, antioxidants, pH modifiers, surfactants, bioavailability modifiers and combinations of these. For administration in the form of nasal drops, the compounds may be formulated in oily solutions or as a gel. For administration of nasal aerosol, any suitable propellant may be used including compressed air, nitrogen, carbon dioxide, or a hydrocarbon based low boiling solvent.

Dosage forms for the topical (including buccal and sublingual) or transdermal administration of compounds of the invention include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Transdermal patches have the added advantage of providing controlled delivery of a compound of the invention to the body. Such dosage forms can be made by dissolving or dispersing the agent in the proper medium. Absorption enhancers can also be used to increase the flux of the inventive compound across the skin. The rate of such flux can be controlled by either providing a rate controlling membrane or dispersing the compound in a polymer matrix or gel.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The formulations of the invention may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, nanoformulation, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

In some embodiments, one or more agents (e.g., KBU2046) are administered (e.g., for inhibiting cell motility, for inhibiting invasion of pre-cancerous lesions, for inhibiting metastasis, etc.) in conjunction with one or more additional treatments, therapies, therapeutics, and/or procedures (e.g., for treatment of cancer, etc.). Although embodiments described herein are not limited by the scope of these additional treatments, therapies, therapeutics, and/or procedures, they may include, hormone therapy, chemotherapy, radiation, surgery, etc., suitable agents for use with the agents described herein (e.g. KBU2046 and analogues thereof) include the following.

Alkylating agents are chemotherapy agents that attack the negatively charged sites on the DNA (e.g., the oxygen, nitrogen, phosphorous and sulfur atoms) and bind to the DNA thus altering replication, transcription and even base pairing. It is also believed that alkylation of the DNA also leads to DNA strand breaks and DNA strand cross-linking. By altering DNA in this manner, cellular activity is effectively stopped and the cancer cell will die. Common alkylating agents include, without limitation, procarbazine, ifosphamide, cyclophosphamide, melphalan, chlorambucil, decarbazine, busulfan, thiotepa, and the like. Alkylating agents such as those mentioned above can be used in combination with one or more other alkylating agents and/or with one or more chemotherapy agents of a different class(es).

Platinum chemotherapy agents are believed to inhibit DNA synthesis, transcription and function by cross-linking DNA subunits. (The cross-linking can happen either between two strands or within one strand of DNA.) Common platinum chemotherapy agents include, without limitation, cisplatin, carboplatin, oxaliplatin, Eloxatin, and the like. Platinum chemotherapy agents such as those mentioned above can be used in combination with one or more other platinums and/or with one or more chemotherapy agents of a different class(es).

Anti-metabolite chemotherapy agents are believed to interfere with normal metabolic pathways, including those necessary for making new DNA. Common anti-metabolites include, without limitation, Methotrexate, 5-fluorouracil (e.g., capecitabine), gemcitabine (2'-deoxy-2',2'-difluorocytidine monohydrochloride (β-isomer), Eli Lilly), 6-mercaptopurine, 6-thioguanine, fludarabine, cladribine, cytarabine, tegafur, raltitrexed, cytosine arabinoside, and the like. Gallium nitrate is another anti-metabolite that inhibits ribonucleotides reductase. Anti-metabolites such as those mentioned above can be used in combination with one or more other anti-metabolites and/or with one or more chemotherapy agents of a different class(es).

Anthracyclines promote the formation of free oxygen radicals. These radicals result in DNA strand breaks and subsequent inhibition of DNA synthesis and function. Anthracyclines are also inhibit the enzyme topoisomerase by forming a complex with the enzyme and DNA. Common anthracyclines include, without limitation, daunorubicin, doxorubicin, idarubicin, epirubicin, mitoxantrone, adriamycin, bleomycin, mitomycin-C, dactinomycin, mithramycin and the like. Anthracyclines such as those mentioned above can be used in combination with one or more other anthracyclines and/or with one or more chemotherapy agents of a different class(es).

Taxanes bind with high affinity to the microtubules during the M phase of the cell cycle and inhibit their normal function. Common taxanes include, without limitation, paclitaxel, docetaxel, Taxotere, Taxol, taxasm, 7-epipaclitaxel, t-acetyl paclitaxel, 10-desacetyl-paclitaxel, 10-desacetyl-7-epipaclitaxel, 7-xylosylpaclitaxel, 10-desacetyl-7-epipaclitaxel, 7-N—N-dimethylglycylpaclitaxel, 7-L-alanylpaclitaxel and the like. Taxanes such as those mentioned above can be used in combination with one or more other taxanes and/or with one or more chemotherapy agents of a different class(es).

Camptothecins complex with topoisomerase and DNA resulting in the inhibition and function of this enzyme. Common camptothecins include, without limitation, irinotecan, topotecan, etoposide, *vinca* alkaloids (e.g., vincristine, vinblastine or vinorelbine), amsacrine, teniposide and the like. Camptothecins such as those mentioned above can be used in combination with one or more other camptothecins and/or with one or more chemotherapy agents of a different class(es).

Nitrosoureas inhibit changes necessary for DNA repair. Common nitrosoureas include, without limitation, carmustine (BCNU), lomustine (CCNU), semustine and the like. Nitrosoureas such as those mentioned above can be used in combination with one or more other nitrosoureas and/or with one or more chemotherapy agents of a different class(es).

EGFR (i.e., epidermal growth factor receptor) inhibitors inhibit EGFR and interfere with cellular responses including cell proliferation and differentiation. EGFR inhibitors include molecules that inhibit the function or production of one or more EGFRs. They include small molecule inhibitors of EGFRs, antibodies to EGFRs, antisense oligomers, RNAi inhibitors and other oligomers that reduce the expression of EGFRs. Common EGFR inhibitors include, without limitation, gefitinib, erlotinib (Tarceva), cetuximab (Erbitux), panitumumab (Vectibix, Amgen) lapatinib (GlaxoSmithKline), CI1033 or PD183805 or canternib (6-acrylamide-N-(3-chloro-4-fluororphenyl)-7-(3-morpholinopropo-xy)quinazolin-4-amine, Pfizer), and the like. Other inhibitors include PKI-166 (4-[(1R)-1-phenylethylamino]-6-(4-hydroxyphenyl)-7H-pyrrolo[2,3-d-]pyrimidine, Novartis), CL-387785 (N-[4-(3-bromoanilino)quinazolin-6-yl]but-2-ynamide), EKB-569 (4-(3-chloro-4-fluororanilino)-3-cyano-6-(4-dimethylaminobut2(E)-enamido)-7-ethoxyquinoline, Wyeth), lapatinib (GW2016, GlaxoSmithKline), EKB509 (Wyeth), panitumumab (ABX-EGF, Abgenix), matuzumab (EMD 72000, Merck), and the monoclonal antibody RH3 (New York Medical). EGFR inhibitors such as those mentioned above can be used in combination with one or more other EGFR inhibitors and/or with one or more chemotherapy agents of a different class(es).

Antibiotics promote the formation of free oxygen radicals that result in DNA breaks leading to cancer cell death. Common antibiotics include, without limitation, bleomycin and rapamycin and the like. The macrolide fungicide rapamycin (also called RAP, rapamune and sirolimus) binds intracellularly to the to the immunophilin FK506 binding protein 12 (FKBP12) and the resultant complex inhibits the serine protein kinase activity of mammalian target of rapamycin (mTOR). Rapamycin macrolides include naturally occurring forms of rapamycin as well as rapamycin analogs and derivatives that target and inhibit mTOR. Other rapamycin macrolides include, without limitation, temsirolimus (CCI-779, Wyeth)), everolimus and ABT-578. Antibiotics such as those mentioned above can be used in combination with one or more other antibiotics and/or with one or more chemotherapy agents of a different class(es).

HER2/neu Inhibitors block the HER2 receptor and prevent the cascade of reactions necessary for tumor survival. Her2 inhibitors include molecules that inhibit the function or production of Her2. They include small molecule inhibitors of Her2, antibodies to Her2, antisense oligomers, RNAi inhibitors and other oligomers that reduce the expression of tyrosine kinases. Common HER2/neu inhibitors include, without limitation, trastuzumab (Herceptin, Genentech) and the like. Other Her2/neu inhibitors include bispecific antibodies MDX-210 (FC.gamma.R1-Her2/neu) and MDX-447 (Medarex), pertuzumab (rhuMAb 2C4, Genentech), HER2/neu inhibitors such as those mentioned above can be used in combination with one or more other HER2/neu inhibitors and/or with one or more chemotherapy agents of a different class(es).

Angiogenesis inhibitors inhibit vascular endothelial growth factor, i.e. VEGF, thereby inhibiting the formation of new blood vessels necessary for tumor life. VEGF inhibitors include molecules that inhibit the function or production of one or more VEGFs. They include small molecule inhibitors of VEGF, antibodies to VEGF, antisense oligomers, RNAi inhibitors and other oligomers that reduce the expression of tyrosine kinases. Common angiogenesis inhibitors include, without limitation, bevacizumab (Avastin, Genentech). Other angiogenesis inhibitors include, without limitation, ZD6474 (AstraZeneca), BAY-43-9006, sorafenib (Nexavar, Bayer), semaxanib (SU5416, Pharmacia), SU6668 (Pharmacia), ZD4190 (N-(4-bromo-2-fluorophenyl)-6-methoxy-7-[2-(1H-1,2,3-triazol-1-yl)ethoxy]-quinazolin-4-amine, Astra Zeneca), Zactima (ZD6474, N-(4-bromo-2-fluorophenyl)-6-methoxy-7-[2-(1H-1,2,3-triazol-1-yl)ethoxy]quinazolin-4-amine, Astra Zeneca), vatalanib, (PTK787, Novartis), the monoclonal antibody IMC-1C11 (Imclone) and the like. Angiogenesis inhibitors such as those mentioned above can be used in combination with one or more other angiogenesis inhibitors and/or with one or more chemotherapy agents of a different class(es).

In addition to EGFR, HER2 and VEGF inhibitors, other kinase inhibitors are used as chemotherapeutic agents. Aurora kinase inhibitors include, without limitation, compounds such as 4-(4-N benzoylamino)aniline)-6-methyoxy-7-(3-(1-morpholino)propoxy)quinazoline (ZM447439, Ditchfield et al., J. Cell. Biol., 161:267-80 (2003)) and hesperadin (Haaf et al., J. Cell Biol., 161: 281-94 (2003)). Other compounds suitable for use as Aurora kinase inhibitors are described in Vankayalapati H, et al., Mol. Cancer. Ther. 2:283-9 (2003). SRC/Abl kinase inhibitors include without limitation, AZD0530 (4-(6-chloro-2,3-methylenedioxyanilino)-7-[2-(4-methylpiperazin-1-ypethox-y]-5-tetrahycropyran-4-yloxyquinazoline). Tyrosine kinase inhibitors include molecules that inhibit the function or production of one or more tyrosine kinases. They include small molecule inhibitors of tyrosine kinases, antibodies to tyrosine kinases and antisense oligomers, RNAi inhibitors and other oligomers that reduce the expression of tyrosine kinases. CEP-701 and CEP-751 (Cephalon) act as tyrosine kinase inhibitors. Imatinib mesylate is a tyrosine kinase inhibitor that inhibits bcr-abl by binding to the ATP binding site of bcr-abl and competitively inhibiting the enzyme activity of the protein. Although imatinib is quite selective for bcr-abl, it does also inhibit other targets such as c-kit and PDGF-R. FLT-3 inhibitors include, without limitation, tandutinib (MLN518, Millenium), sutent (SU11248, 5-[5-fluoro-2-oxo-1,2-dihydroindol-(3Z)-ylidenemethyl]-2,4-dimethyl-1H-py-rrole-3-carboxylic acid [2-diethylaminoethyl]amide, Pfizer), midostaurin (4'-N-benzoyl staurosporine, Novartis), lefunomide (SU101) and the like. MEK inhibitors include, without limitation, 2-(2-Chloro-4-iodo-phenylamino)-N-cyclopropylmethoxy-3,4-difluoro-benzami-de) (PD184352/CI-1044, Pfizer), PD198306 (Pfizer), PD98059 (2'-amino-3'-methoxyflavone), U0126 (Promega), Ro092-210 from fermented microbial extracts (Roche), the resorcyclic acid lactone, L783277, also isolated from microbial extracts (Merck) and the like. Tyrosine kinase inhibitors such as those mentioned above can be used in combination with one or more other tyrosine kinase inhibitors and/or with one or more chemotherapy agents of a different class(es).

Proteaosome inhibitors inhibit the breakdown of some of these proteins that have been marked for destruction. This results in growth arrest or death of the cell. Common proteaosome inhibitors include, without limitation, bortezomib, ortezomib and the like. Proteaosome inhibitors such as those mentioned above can be used in combination with one or more other proteaosome inhibitors and/or with one or more chemotherapy agents of a different class(es).

Immunotherapies are thought to bind to and block specific targets, thereby disrupting the chain of events needed for tumor cell proliferation. Common immunotherapies include, without limitation, rituximab and other antibodies directed against CD20, Campath-1H and other antibodies directed against CD-50, epratuzmab and other antibodies directed against CD-22, galiximab and other antibodies directed against CD-80, apolizumab HU1D10 and other antibodies directed against HLA-DR, and the like. Radioisotopes can be conjugated to the antibody, resulting in radioimmunotherapy. Two such anti-CD20 products are tositumomab (Bexxar) and ibritumomab (Zevalin) Immunotherapies such as those mentioned above can be used in combination with one or more other immunotherapies and/or with one or more chemotherapy agents of a different class(es).

Hormone therapies block cellular receptors, inhibit the in vivo production of hormones, and/or eliminate or modify hormone receptors on cells, all with the end result of slowing or stopping tumor proliferation. Common hormone therapies include, without limitation, antiestrogens (e.g., tamoxifen, toremifene, fulvestrant, raloxifene, droloxifene, idoxifene and the like), progestogens) e.g., megestrol acetate and the like) aromatase inhibitors (e.g., anastrozole, letrozole, exemestane, vorozole, exemestane, fadrozole, aminoglutethimide, exemestane, 1-methyl-1,4-androstadiene-3,17-dione and the like), anti-androgens (e.g., bicalutimide, nilutamide, flutamide, cyproterone acetate, and the like), luteinizing hormone releasing hormone agonist (LHRH Agonist) (e.g., goserelin, leuprolide, buserelin and the like); 5-.alpha.-reductase inhibitors such as finasteride, and the like. Hormone therapies such as those mentioned above can be used in combination with one or more other hormone therapies and/or with one or more chemotherapy agents of a different class(es).

Photodynamic therapies expose a photosensitizing drug to specific wavelengths of light to kill cancer cells. Common photodynamic therapies include, for example, porfimer sodium (e.g., Photofrine) and the like. Photodynamic therapies such as those mentioned above can be used in combination with one or more other photodynamic therapies and/or with one or more chemotherapy agents of a different class(es).

Cancer vaccines are thought to utilize whole, inactivated tumor cells, whole proteins, peptide fragments, viral vectors and the like to generate an immune response that targets cancer cells. Common cancer vaccines include, without limitation, modified tumor cells, peptide vaccine, dendritic vaccines, viral vector vaccines, heat shock protein vaccines and the like.

Histone deacetylase inhibitors are able to modulate transcriptional activity and consequently, can block angiogenesis and cell cycling, and promote apoptosis and differentiation. Histone deacetylase inhibitors include, without limitation, SAHA (suberoylanilide hydroxamic acid), depsipeptide (FK288) and analogs, Pivanex (Titan), CI994 (Pfizer), MS275 PXD101 (CuraGen, TopoTarget) MGCD0103 (MethylGene), LBH589, NVP-LAQ824 (Novartis) and the like and have been used as chemotherapy agents. Histone deacetylase inhibitors such as those mentioned above can be used in combination with one or more other histone deacetylase inhibitors and/or with one or more chemotherapy agents of a different class(es).

Modulators of Sphingolipid metabolism have been shown to induce apoptosis. For reviews see N. S. Raclin, Biochem J, 371:243-56 (2003); D. E. Modrak, et al., Mol. Cancer. Ther, 5:200-208 (2006), K. Desai, et al., Biochim Biophys Acta, 1585:188-92 (2002) and C. P. Reynolds, et al. and Cancer Lett, 206, 169-80 (2004), all of which are incorporated herein by reference. Modulators and inhibitors of various enzymes involved in sphingolipid metabolism can be used as chemotherapeutic agents. Ceramide has been shown to induce apoptosis. Other analogs include, without limitation, Cer 1-glucuronide, poly(ethylene glycol)-derivatized ceramides and pegylated ceramides. Modulators that stimulate ceramide synthesis have been used to increase ceramide levels. Compounds that stimulate serine palmitoyltransferase, an enzyme involved in ceramide synthesis, include, without limitation, tetrahydrocannabinol (THC) and synthetic analogs and anandamide, a naturally occurring mammalian cannabinoid. Gemcitabine, retinoic acid and a derivative, fenretinide [N-(4-hydroxyphenyl)retinamide, (4-HPR)], camptothecin, homocamptothecin, etoposide, paclitaxel, daunorubicin and fludarabine have also been shown to increase ceramide levels. In addition, valspodar (PSC833, Novartis), a non-immunosuppressive non-ephrotoxic analog of cyclosporin and an inhibitor of p-glycoprotein, increases ceramide levels. Modulators of sphingomyelinases can increase ceramide levels. They include compounds that lower GSH levels, as GSH inhibits sphingomyelinases. For example, betathine (β-alanyl cysteamine disulphide), oxidizes GSH, and has produced good effects in patients with myeloma, melanoma and breast cancer. COX-2 inhibitors, such as celecoxib, ketoconazole, an antifungal agent, doxorubicin, mitoxantrone, D609 (tricyclodecan-9-yl-xanthogenate), dexamethasone, and Ara-C (1-β-D-arabinofuranosylcytosine) also stimulate sphingomyelinases. Molecules that stimulate the hydrolysis of glucosylceramide also raise ceramide levels. The enzyme, GlcCer glucosidase, which is available for use in Gaucher's disease, particularly with retinol or pentanol as glucose acceptors and/or an activator of the enzyme can be used as therapeutic agents. Saposin C and analogs thereof, as well as analogs of the anti-psychotic drug, chloropromazine, may also be useful. Inhibitors of glucosylceramide synthesis include, without limitation, PDMP (N-[2-hydroxy-1-(4-morpholinylmethyl)-2-phenylethyldecanamide]), PMPP (D,L-threo-(1-phenyl-2-hexadecanoylamino-3-morpholino-1-propanol), P4 or PPPP (D-threo-1-phenyl-2-palmitoylamino-3-pyrrolidino-1-propanol), ethylenedioxy-P4,2-decanoylamine-3-morpholinoprophenone, tamixofen, raloxifene, mifepristone (RU486), N-butyl deoxynojirimycin and anti-androgen chemotherapy (bicalutamide+leuprolide acetate). Zavesca, (1,5-(butylimino)-1,5-dideoxy-D-glucitol) usually used to treat Gaucher's disease, is another inhibitor of glucosylceramide synthesis. Inhibitors of ceramidase include, without limitation, N-oleoylethanolamine, a truncated form of ceramide, D-MAPP (D-erythro-2-tetradecanoylamino-1-phenyl-1-propanol) and the related inhibitor B13 (p-nitro-D-MAPP). Inhibitors of sphingosine kinase also result in increased levels of ceramide. Inhibitors include, without limitation, safingol (L-threo-dihydrosphingosine), N,N-dimethyl sphingosine, trimethyl sphingosine and analogs and derivatives of sphingosine such as dihydrosphingosine, and myriocin. Fumonisins and fumonisin analogs, although they inhibit ceramide synthase, also increase levels of sphinganine due to the inhibition of de novo sphingolipid biosynthesis, resulting in apoptosis. Other molecules that increase ceramide levels include, without limitation, miltefosine (hexadecylphosphocholine). Sphingolipid modulators, such as those mentioned above, can be used in combination with one or more other sphingolipid modulators and/or with one or more chemotherapy agents of a different class(es).

In some embodiments, oligonucleotides are provided as cancer therapies. They include Genasense (oblimersen, G3139, from Genta), an antisense oligonucleotide that targets bcl-2 and G4460 (LR3001, from Genta) another antisense oligonucleotide that targets c-myb. Other oligomers include, without limitation, siRNAs, decoys, RNAi oligonucleotides and the like. Oligonucleotides, such as those mentioned above, can be used in combination with one or more other oligonucleotide inhibitors and/or with one or more chemotherapy agents of a different class(es).

Chemotherapy agents can include cocktails of two or more agents (e.g., KBU2046 and a chemotherapeutic and/or hormone therapeutic). In several embodiments, a chemotherapy agent is a cocktail that includes two or more alkylating agents, platinums, anti-metabolites, anthracyclines, taxanes, camptothecins, nitrosoureas, EGFR inhibitors, antibiotics, HER2/neu inhibitors, angiogenesis inhibitors, kinase inhibitors, proteaosome inhibitors, immunotherapies, hormone therapies, photodynamic therapies, cancer vaccines, sphingolipid modulators, oligomers or combinations thereof.

In several embodiments of the present invention, radiation therapy is administered in addition to the administration of an oligonucleotide compound. Radiation therapy includes both external and internal radiation therapies.

In some embodiments, of the present invention, surgery is used to remove cancerous tissue from a patient. Cancerous tissue can be excised from a patient using any suitable surgical procedure including, for example, laparoscopy, scalpel, laser, scissors and the like. In several embodiments, surgery is combined with chemotherapy. In other embodiments, surgery is combined with radiation therapy. In still other embodiments, surgery is combined with both chemotherapy and radiation therapy.

Embodiments are described herein for inhibiting the movement of human breast, lung and colon cancer cells. Compositions and methods to such an end find use, for example, in: (1) inhibiting invasion of precancerous lesions (e.g., non-invasive lesions; also known as in situ lesions or in situ cancer), and inhibiting the formation of true, e.g., invasive cancer; (2) inhibiting organ confined cancer from invading outside of the local organ and invading into adjacent organs (e.g., inhibiting lung cancer from invading into the center of the chest where it can penetrate the aorta and cause death through resultant blood loss); and (3) inhibiting movement of cancer cells throughout the body (e.g., inhibit metastasis). Compositions and methods find use in, for example, colon, breast and lung cancers, all of which commonly invade local organs, thereby inducing morbidity and mortality, and all of which metastasize throughout the body, inducing morbidity and mortality. Experiments conducted during development of embodiments described herein demonstrate inhibition of the function of heat shock protein 90 (HSP90) by inhibiting phosphorylation of its serine 226. The function of HSP90 is inhibited by increasing its ability to bind CDC37. A series of compounds have been designed to increase HSP90/CDC37 interaction, and experiments have demonstrated that they inhibit cancer cell motility. It has been demonstrated that therapeutically inhibiting cancer cell motility can be combined with cytotoxic chemotherapy and that it increases it effectiveness. It was been demonstrated that therapeutically inhibiting cancer cell motility can be combined with hormone therapy for prostate cancer, and that it increases it effectiveness. Further, the approaches described herein can be applied to overcome resistance to hormone therapy, and in a wide variety of cancers.

EXPERIMENTAL

Example 1

Materials and Methods

Selection and Synthesis of Optimized Small Chemical Probes

Functional screens consisted of a Boyden chamber cell invasion assay (Craft et al., 2007; herein incorporated by reference in its entirety) for efficacy, and a three day cell growth inhibition assay (Liu et al., 2002; herein incorporated by reference in its entirety) for toxicity. Additional functional measures of toxicity included a NCI-based screen of the NCI 60-cell line panel (Shoemaker, 2006; herein incorporated by reference in its entirety), expression of estrogen-responsive genes by qRT/PCR (Ding et al., 2007; herein incorporated by reference in its entirety), induction of an estrogen-responsive promoter by luciferase assay (Breen et al., 2013; Catherino and Jordan, 1995; herein incorporated by reference in their entireties), and a hematopoietic stem cell 14-day colony formation assay (Bergan et al., 1996; herein incorporated by reference in its entirety). Protein Data Base (PDB) X-ray crystallographic structural data (PDB IDs: IX7R, IX7J) was used to determine what chemical groups of genistein bound to the ER. The migration of individual cells was assessed by time-lapse video microscopy.

Evaluation of KBU2046 Efficacy and Pharmacokinetics in Murine Models

Orthotopic implantation of human PCa cells and quantification of distant metastasis was performed as described (Pavese et al., 2013; herein incorporated by reference in its entirety). Orthotopic implantation of human breast cancer cells, followed by surgical removal of resultant primary tumor, was performed as described (du Manoir et al., 2006; herein incorporated by reference in its entirety). Quantification of KBU2046 plasma concentrations was performed by LCMS. Resultant pharmacokinetic parameters were calculated with a three-compartment model using a naive pooled data approach (Kataria et al., 1994; herein incorporated by reference in its entirety), oral bioavailability was calculated as described in Avram et al., 2009 (herein incorporated by reference in its entirety), model fitting used the extended least-squares maximum likelihood function with data weighted with the inverse of the model-based variance of the data at the observation times (Barrett et al., 1998; herein incorporated by reference in its entirety), and model misspecification sought by inspection of the measured and predicted findings (Cobelli and Foster, 1998; Foster, 1998; herein incorporated by reference in their entireties). Critical organs were examined for structural damage using a semi-quantitative histological scoring system (Knodell et al., 1981; herein incorporated by reference in its entirety), while their function was assessed by comprehensive clinical laboratory testing of blood samples. All animal experiments were conducted under protocols approved by the Institutional Animal Care and Use Committee of Northwestern University.

Evaluating KBU2046's Ability to Inhibit the MKK4 Pathway

The ability of small chemicals to bind MKK4 was assessed by Fluorescence thermal shift assay (Krishna et al., 2013; herein incorporated by reference in its entirety) and by isothermal titration calorimetry (Polier et al., 2013; Zubriene et al., 2010; herein incorporated by reference in their entireties), their ability to inhibit MKK4 kinase activity was assessed by in vitro kinase assay (Krishna et al., 2013; herein incorporated by reference in its entirety), and their ability to inhibit cell signaling in cells was assessed by phosphoprotein Western blot (Huang et al., 2005; Xu and Bergan, 2006; herein incorporated by reference in their entireties).

Using Proteomics to Identify the Pharmacologic Site of Action of KBU2046

Screening for changes in the kinome induced by KBU2046 were evaluated with the Kinoview™ assay system. Proteins pulled down by motif-directed Kinoview™ antibody were identified through PhosphoScan™ technology, using LTQ-Orbitrap LC-MS/MS analysis coupled to a SEQUEST/Sorcerer data analysis suite (Lundgren et al., 2009; herein incorporated by reference in its entirety).

Defining the Protein Cleft where KBU2046 Binds

Stabilization of HSP90β/CDC37 heterocomplexes was evaluated by a drug affinity responsive target stability (DARTS) assay (Lomenick et al., 2009; herein incorporated by reference in its entirety). Construction of an in silico model used experimental data resulting from KBU2046 compound structure, DARTS assays, crystal structures of human HSP90β (pDBs luym, 3nmq and 3pry) and of HSP82-CDC37 complex from yeast (PDB lus7), which were determined by X-ray diffraction-based crystallographic analysis, and experimental probing of HSP90β structure using varied length chemical cross-linkers (Chavez et al., 2013; herein incorporated by reference in its entirety) coupled to MS3 analysis using ReACT (Weisbrod et al., 2013; herein incorporated by reference in its entirety) in a manner that satisfies expected Protein Interaction Reporter mass relationships (Tang et al., 2005; herein incorporated by reference in its entirety). Experimentally determined structural information was then integrated and analyzed on the APPLIED Pipeline (Analysis Pipeline for Protein Ligand Interactions and Experimental Determination) at the Argonne Leadership Computing Facility, Argonne National Laboratory. Building upon experimental findings, the analysis followed a multi-stage algorithm that took into consideration protein-protein and protein-ligand interactions by combining evolutionary protein surface analysis (Binkowski et al., 2003; Binkowski and Joachimiak, 2008; Binkowski et al., 2005; herein incorporated by reference in their entireties), robust homology modeling (Leaver-Fay et al., 2011; herein incorporated by reference in its entirety), massively parallel docking simulations using mixed strategies (Deng and Roux, 2008; Graves et al., 2008; Lang et al., 2009; Moni.s et al., 2009; Wang et al., 2006; herein incorporated by reference in their entireties), and advanced, physics-based rescoring methodologies (Jiang et al., 2009; Jiang and Roux, 2010; Wang et al., 2006; herein incorporated by reference in their entireties).

Example 2

Chemical Synthesis

Exemplary Procedure for Large-Scale Production of 4'-Fluoroisoflavanone (KBU2046).

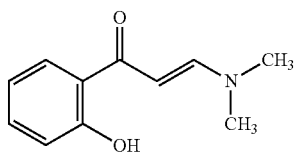

3-(dimethylamino)-1-(2-hydroxyphenyl)prop-2-en-1-one. The starting materials 2'-hydroxyacetophenone (50 mmol, 6.02 mL) and N,Ndimethylformamide dimethyl acetal (50 mmol, 6.64 mL) were added to a 10-20 mL microwave vial. The vial was capped and heated in a Biotage Initiator microwave synthesizer at 150° C. and 11 bar for 10 minutes. The resulting dark orange liquid was allowed to cool to 23° C., at which time yellow-orange crystals crashed out of solution. The crystals were collected and washed with hexanes (50 mL), then dried and weighed to give 3-(dim-ethylamino)-I-(2-hydroxyphenyl)prop-2-en-I-one (9.09 g, 95%) as orange-yellow needles. Product was confirmed by NMR and ultra-performance liquid chromatography/mass spectrometry (UPLCMS).

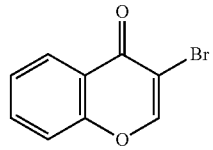 [SMILES: O=c1c(Br)coc2ccccc12]

3-bromochromone. 3-bromochromone was prepared by a procedure taken from Gammill (Gammill, 1979; herein incorporated by reference in its entirety). To a flame-dried 250 mL round bottom flask, was added 3-(dimethylamino)-1-(2-hydroxyphenyl)prop-2-en-1-one (36.6 mmol, 7.0 g), which was dissolved in $CHCl_3$ (70 mL). The reaction flask was cooled to 0° C. in an ice bath, then $Br_2$ (36.6 mmol, 1.87 mL) was added dropwise through an addition funnel. After all of the $Br_2$ was added, water (70 mL) was added slowly to the reaction and it was stirred at 23° C. for 10 minutes. The dark orange/yellow organic layer was then separated from the aqueous layer, which was back extracted with 3×50 mL $CHCl_3$. The combined organic layers were then dried over $Na_2SO_4$ and concentrated to give a dark orange oil. This was purified by flash column chromatography ($SiO_2$ 10% EtOAc/hexanes) to afford 3-bromochromone (5.26 g, 64%) as an off-white solid. Product was confirmed by NMR and ultra-performance liquid chromatography/mass spectrometry (UPLCMS).

Palladium Tetrakis(Triphenylphosphine) ($Pd(PPh_3)_4$).

The catalyst for the Suzuki-Miyaura cross-coupling reaction to synthesize 4'-fluoroisoflavone was made using a procedure by Coulson (Coulson et al., 1990; herein incorporated by reference in its entirety). To a flame-dried 100 mL Schlenk flask was added $PdCl_2$ (5 mmol, 890 mg) and triphenylphosphine (25 mmol, 6.56 g). The solids were dissolved in DMSO (60 mL), then the mixture was purged with $N_2$ and heated to 145° C., at which time it turned a bright yellow-orange color. The reaction was removed from heat and allowed to stir at room temperature for 15 minutes, then hydrazine hydrate (20 mmol, 0.972 mL) was added via syringe, with a vent needle in place to account for the formation of $N_2$ gas. After the hydrazine hydrate had been added, the reaction was cooled to 23° C., during which time a yellow solid crashed out of solution. The solid was washed under Schlenk filtration conditions with 2×50 mL EtOH, then 2×50 mL ether to yield $Pd(PPh_3)_4$ (5.31 g, 94%) as a canary yellow solid that was stored under $N_2$.

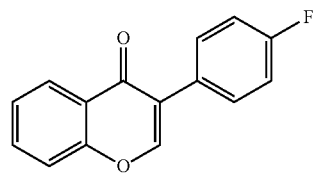 [SMILES: O=c1c(-c2ccc(F)cc2)coc2ccccc12]

4'-fluoroisoflavone. 4'-fluoroisoflavone was prepared on large scale according to a procedure from Suzuki and Miyaura (Hoshino et al., 1988; herein incorporated by reference in its entirety). To a flame-dried 500 mL round bottom flask was added 3-bromochromone (50 mmol, 11.25 g), 4-fluorophenylboronic acid (55 mmol, 7.69 g) and $NazC03$ (100 mmol, 10.6 g). The solids were dissolved in a mixture of benzene (100 mL) and water (50 mL), and the system was purged with $N_2$ for 10-15 minutes. The $Pd(PPh_3)_4$ catalyst (2.5 mmol, 2.89 g) was then added, at which time the reaction turned a bright orange. The flask was equipped with a reflux condenser and the reaction was heated to reflux (80° C.) overnight. After approximately 16 h, the reaction was cooled to 23° C. and was diluted with EtOAc (250 mL), then the crude material was passed through a plug of silica with EtOAc as the eluent. The organic material was dried over Na$_2$SO$_4$ and concentrated to give a dark brown solid that was adsorbed onto silica gel using DCM. Material purified by flash column chromatography (SiO$_2$, 20% EtOAc/hexanes) to afford 4'-fluoroisoflavone (8.14 g, 67% yield) as a yellow-orange solid that showed minor impurities by $^1$H NMR spectroscopy. Slightly impure material was taken onto the next step of the synthesis without further purification. Product was confirmed by NMR and ultra-performance liquid chromatography/mass spectrometry (UPLCMS).

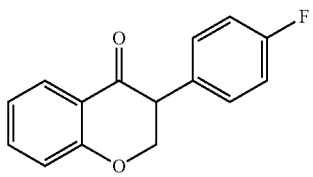

4'-fluoroisoflavanone (KBU2046). To a flame-dried 500 mL round bottom flask was added 4'-fluoroisoflavone (25 mmol, 6.01 g), and the solid was dissolved in dry THF (100 mL). The solution was cooled to −78° C. (dry ice/acetone bath), monitored by a thermocouple. Once the solution had cooled to the desired temperature, L-selectride (55 mmol, 55 mL, 1 M solution in THF) was added dropwise over a period of 30-45 minutes. The reaction was then allowed to stir at −78° C. for 2 h, after which time it was quenched with MeOH (55 mL) at −78° C. The mixture was then poured into 300 mL of water, and the aqueous layer was adjusted to pH 7 with 2 M HCl. The aqueous layer was extracted 2×200 mL with EtOAc, then the combined organic layers were dried over Na$_2$SO$_4$ and concentrated to give a dark brown oily solid. This was purified by flash column chromatography (SiO$_2$, 1:1 hexanes:DCM) to give 4.5 g of crude material that was recrystallized in hexanes to afford 4'-fluoroisoflavanone (3.4 g, 56%) as a fluffy white solid. It was checked for purity by both $^1$H NMR and HPLC analysis, with material that was >98% pure taken onto animal studies.

Related analog compounds were synthesized in addition to the parent 4'-fluoroisoflavanone (KBU2046). These compounds were prepared in the same general manner of KBU2046. The structure and purity of the additional analogs were confirmed by NMR spectroscopy ($^1$H and $^{13}$C) as well as by UPLCMS (minimal ion fragmentation). All compounds were isolated and stored in powdered form (in the absence of light) and were formulated into DSMO stock solutions just prior to use.

Example 3

KBU2046 Inhibition of Cell Motility and Metastasis

Identification of a Selective Inhibitor of Cell Motility and Metastasis

Flavonoids were selected as a platform to advance the synthesis of probes, for at least the reasons that they exert a wide range of biological effects, and because changes in their structure by a single atom can significantly impact their spectrum of biological activity (Andersen and Markham, 2006; herein incorporated by reference in its entirety). Consequently, they constitute biological probes with atom-level resolving capacity, and their chemical scaffold supports a high level of tailored, selective, medicinal chemistry refinement. 4',5,7-trihydroxyisoflavone (genistein) was selected as a starting point. It has been demonstrated that genistein inhibits human prostate cancer (PCa) cell invasion in vitro (Huang et al., 2005; herein incorporated by reference in its entirety), and in the context of a prospective human trial that it down regulates matrix metalloproteinase 2 (MJ\P-2) expression in prostate tissue (Xu et al., 2009; herein incorporated by reference in its entirety). However, its known wide spectrum of biological effects render it unusable as a selective and potent biological probe (Pavese et al., 2010; herein incorporated by reference in its entirety). But, these very same properties optimize its potential to selectively probe a wide spectrum of bioactive sites upon chemical diversification.

From genistein, chemical probes were developed by systematic medicinal chemistry diversification with iterative selection for inhibition of human PCa cell invasion (FIG. 1). Along with this selectivity profiling, a major goal was deselection for inhibition of cell growth (an indicator of off-target effects). Importantly, genistein is known to exert estrogenic effects (Messina et al., 2006; herein incorporated by reference in its entirety), and they were considered off-target with respect to the goal of selectively modulating cell motility. Guided by the crystal structure of the estrogen receptor (ER) with bound genistein (Manas et al., 2004; herein incorporated by reference in its entirety), ER-binding was deselected for. Using this strategy, (±)-3(4-fluorophenyl)chroman-4-one (KBU2046), a halogen-substituted isoflavanone, was discovered (FIG. 1).

Figure 2A:
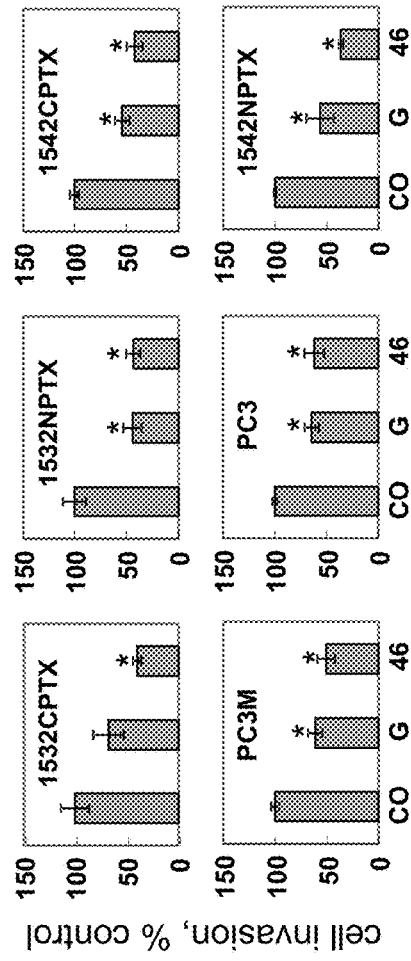
Figure 2B:
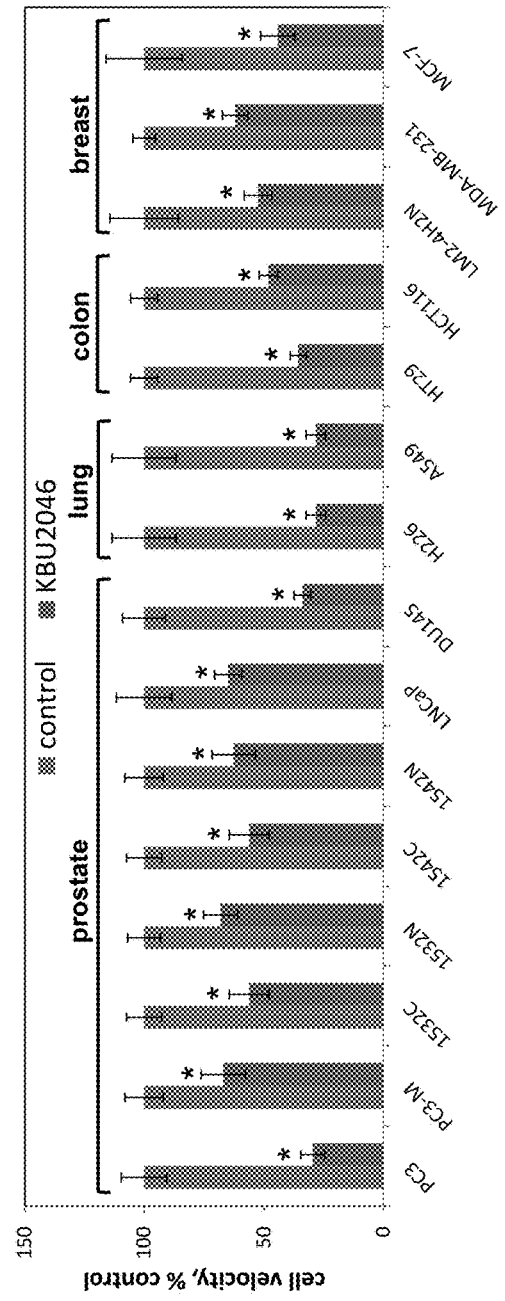
Figure 2D:
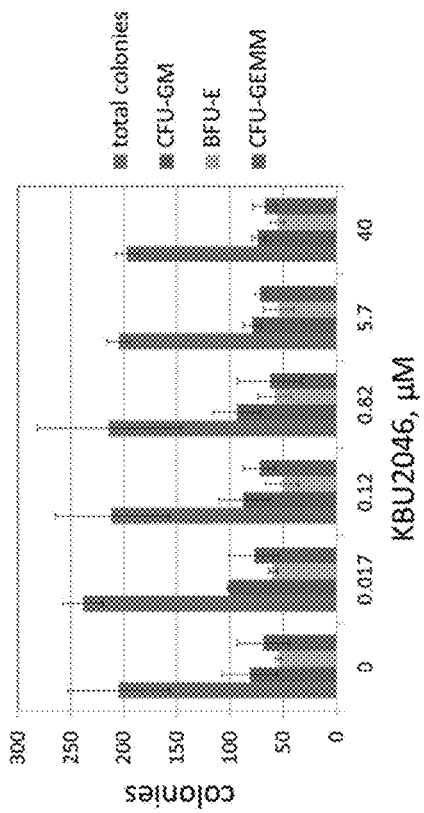
Figure 2E:
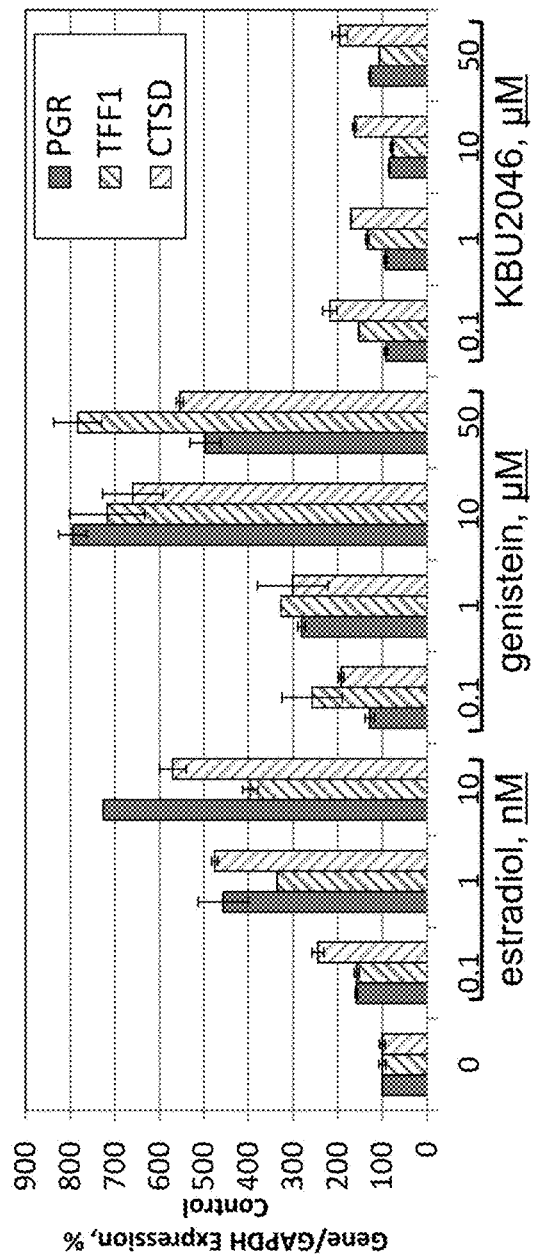
Figures 9, 10:
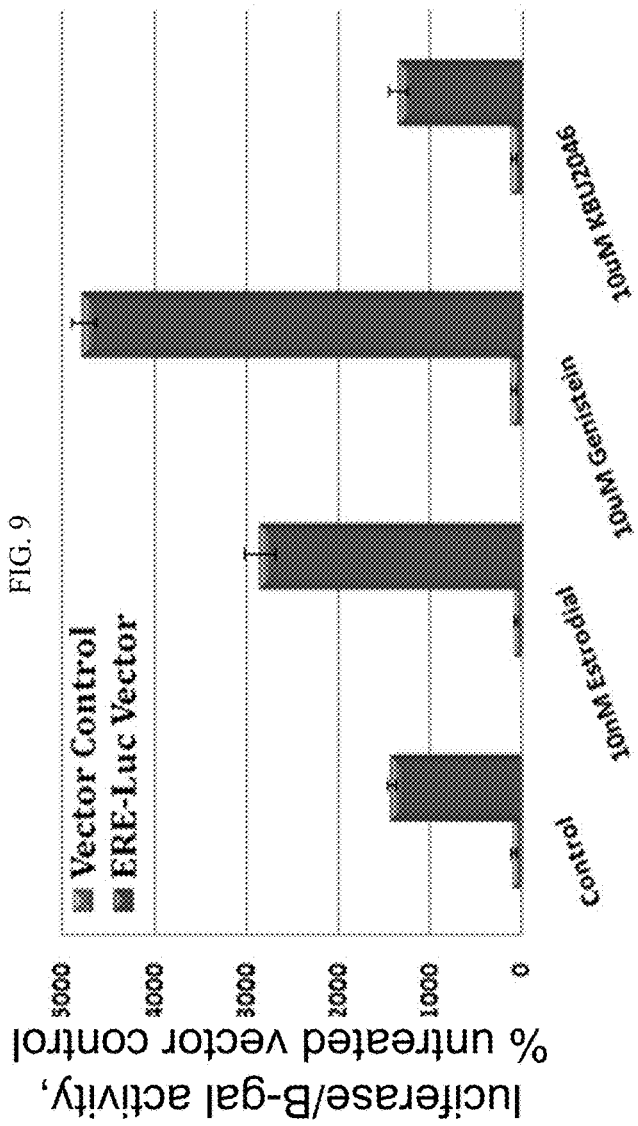
FIG. 9. KBU2046 does not activate the estrogen receptor (ER). Estrogen receptor positive MCF-7 cells were transfected pERE-Luc or empty control vector, along with constitutive active β-gal, grown under estrogen-free conditions, and pre-treated for 24 hours with nanomolar concentrations of estradiol, or with micromolar concentrations of genistein or KBU2046, as indicated. Luciferase activity was measured, normalized to that of β-gal, and values expressed as the percent of untreated vector control cells. Values are the mean±SD.
FIG. 10. Chemical properties of KBU2046 that favor its ability to reach the cellular target when delivered systemically. In order for small compound probes to exert biological efficacy at the systemic level, they must be able to reach their protein target inside the body, and thus they must possess a favorable pharmacologic profile. Recognized chemical properties associated with favorable pharmacologic attributes (Lipinski et al., 2001; herein incorporated by reference in its entirety) are provided in the table, as are the associated chemical properties of KBU2046.

KBU2046 inhibits cell invasion equal-to-or-greater-than that of genistein for human prostate cells, including normal prostate epithelial cells, as well as primary and metastatic PCa cells (FIG. 2A). Cell migration is a major determinant of cell invasion (Friedl and Wolf, 2003; herein incorporated by reference in its entirety), and KBU2046 inhibited the migration of human prostate, breast, colon and lung cancer cells (FIG. 2B). Importantly, KBU2046 had high selectivity in cellular assays. It was not toxic to human prostate cells (FIG. 2C), to human bone marrow stem cells (FIG. 2D), nor to cells in the NCI60 cell line panel (FIG. 9). Toxicity to bone marrow is induced by a wide array of different therapeutic agents, and is a frequent and dose-limiting toxicity of anti-cancer agents (Guest and Uetrecht, 1999; herein incorporated by reference in its entirety). Furthermore, in estrogen-responsive human breast cancer MCF-7 cells, KBU2046 did not activate estrogen-responsive genes (FIG. 2E; FIG. 9).

KBU2046 Selectively Inhibits Metastasis and Prolongs Survival

Figure 3A:
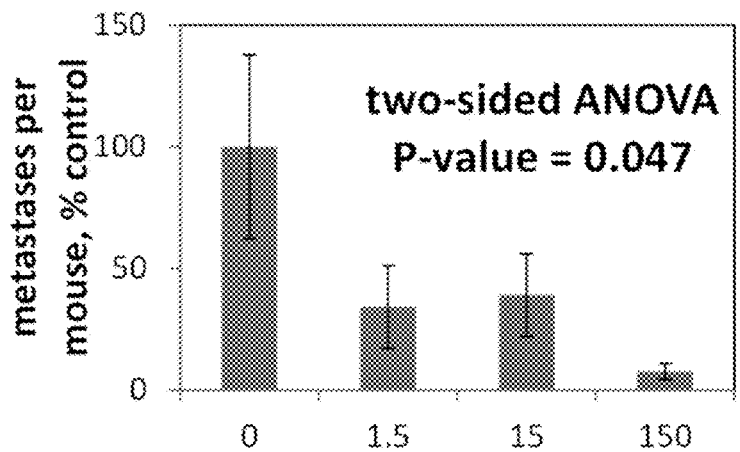
FIGS. 3A-D. KBU2046 inhibits cancer metastasis and prolongs life. (A, B) Inhibition of PCa metastasis. Cohorts of athymic mice bearing human PCa PC3-M cell orthotopic implants (A), or of non-tumor bearing athymic mice (B), were treated with KBU2046 incorporated into chow, and resultant lung metastasis (A) or plasma KBU2046 concentration (B) measured. Values are the mean±SEM. The relationship between dose and metastasis was evaluated by two-sided ANOVA (A). (C) Comprehensive characterization of KBU2046 pharmacokinetics. CD1 mice were dosed with 100 mg KBU2046/kg via oral gavage or intravenous injection (iv), and blood collected at the indicated time points. The dotted horizontal line denotes a concentration of 24 nM, which was the concentration of KBU2046 measured in the blood of mice whose metastasis were suppressed by 92% (A, B). (D) Prolongation of survival in BCa bearing mice. Mice were orthotopically implanted with human breast cancer LM2-4H2N cells, the resultant primary tumors resected, and adjuvant treatment begun with KBU2046 by daily oral gavage five times/week.
Figure 3B:
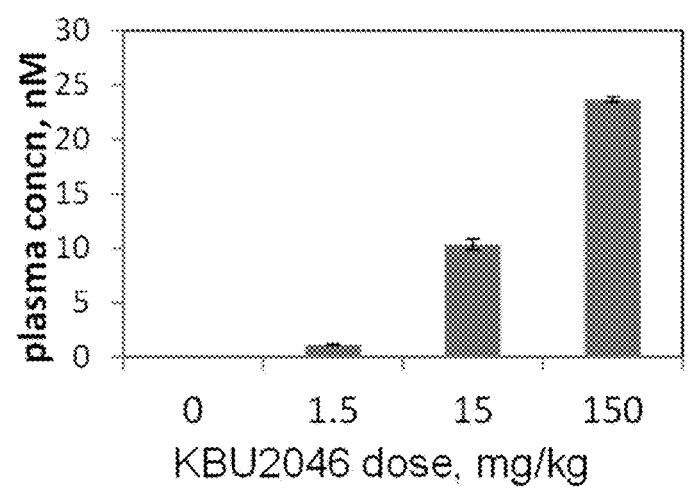
Figure 11:
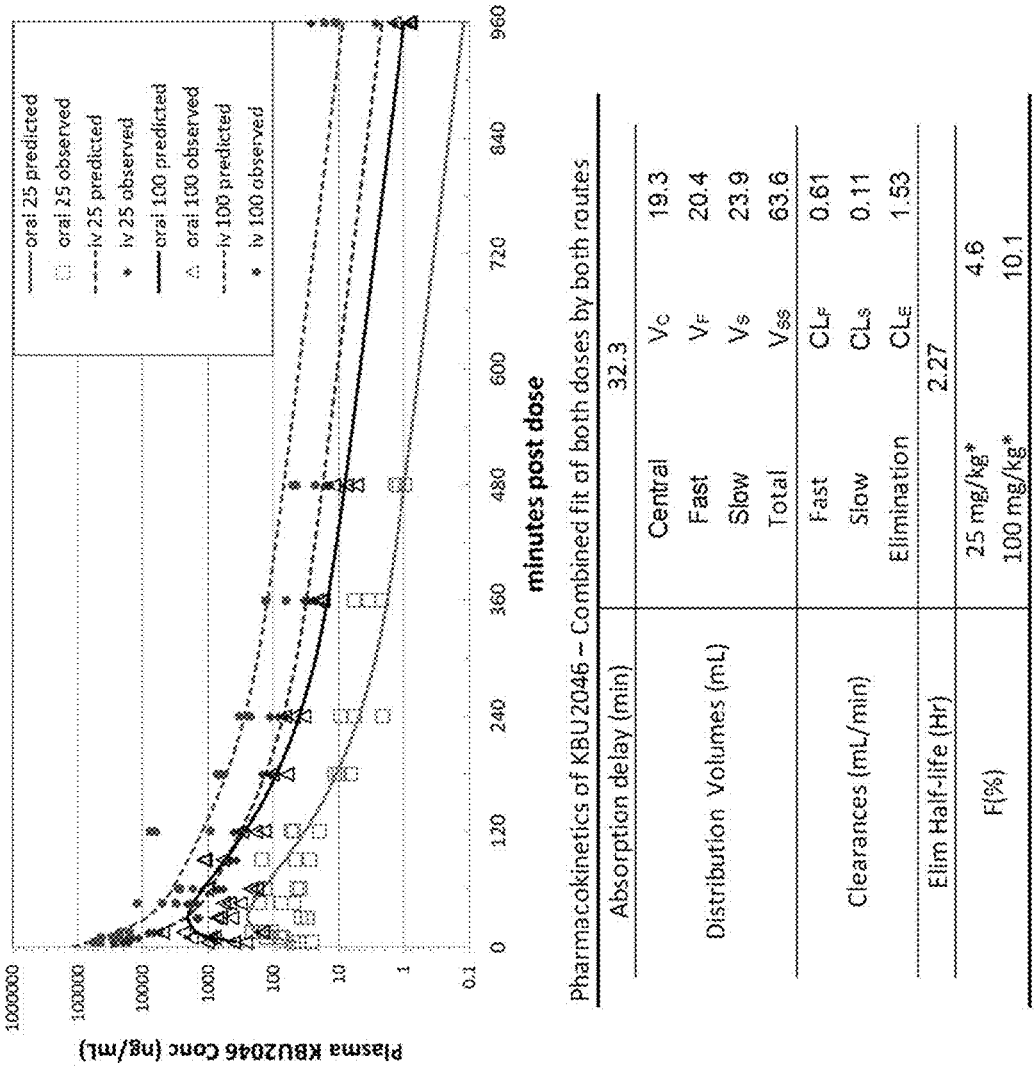
FIG. 11. Extensive pharmacokinetic (PK) analysis of KBU2046. CD1 mice were dosed with 25 or 100 mg/kg KBU2046 via oral gavage or intravenous injection (iv), and blood collected at 0 (pre-dose), 5, 10, 15, 30, 45, 60, 90, 120, 180, 240, 360, 480 and 960 minutes post dose. (top graph) Concentration versus time plot, expressed as ng/ml. The 100 mg dosing data was re-plotted and expressed as nM. (bottom table) The resultant pharmacokinetic parameters. Values are parameter estimates from a naive pooled data approach in which single plasma concentrations measured for individual animals were pooled for both routes of administration of both doses and modeled simultaneously.
Figure 12:
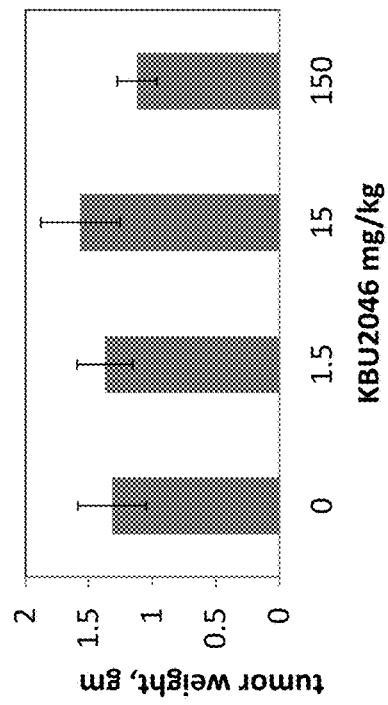
FIG. 12. Graph demonstrating that KBU2046 does not inhibit primary tumor cell growth.
Figure 13:
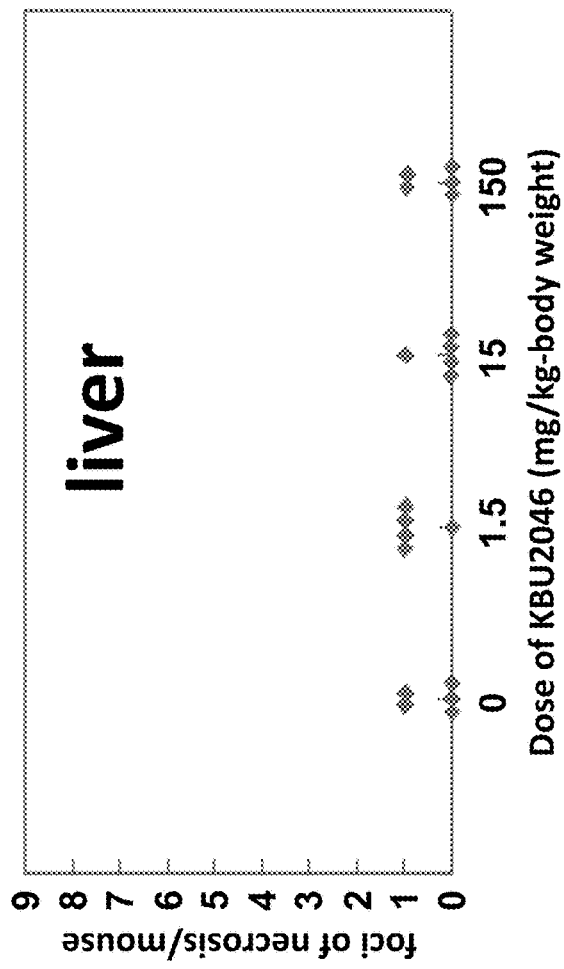
FIG. 13. KBU2046 treatment is not associated with systemic off-target effects. For histologic examination of tissue, cohorts male 6-8 week old Balb/c athymic mice (Charles River Laboratories), which did not receive orthotopic implants, were treated with. After 35 days of treatment, the following organs were harvested at necropsy, and stained with H&E (alternative staining methods as indicated): heart, lungs, esophagus, stomach, colon, small intestine, liver (Trichrome staining), kidneys (Trichrome staining), adrenals, bladder, prostate, spleen, pancreas, brain, testes, and bone marrow and peripheral blood (Giemsa staining). Organs were examined for damage using a semi-quantitative histological scoring system (Knodell et al., 1981; herein incorporated by reference in its entirety). No organ damage was observed, except in the livers of both control and treatment mice. Changes in the liver observed in control mice were not increased by KBU2046 treatment. Mice were immunocompromised, and changes in the liver reflected episodic and minor foci of necrosis, consistent with a prior resolved infection; clinically, mice were all healthy. For examination of organ function, studies used cohorts of 22-24 gm CD1 (ICR) mice (Charles River). Note that for 22-24 gm/mouse, this translated to 5-7 week old females and 4.5-5.5 week old males. Mice were dosed once intravenously with KBU2046 at 0 (vehicle), 15, 75 or 125 mg/kg-body weight. On day 8 and 14, all critical organs were weighed, and the following parameters measured in blood: cholesterol, triglycerides, alanine aminotransferase (ALT), aspartate aminotransferase (AST), total bilirubin, glucose, phosphorus, total protein, calcium, blood urea nitrogen (BUN), creatinine, albumin, Na, K, Cl, white blood cells (with differential), red blood cells, hemoglobin, platelets. No abnormal alterations in any of these parameters were observed, and there were no significant differences between treatment and control mice.
Figure 14A:
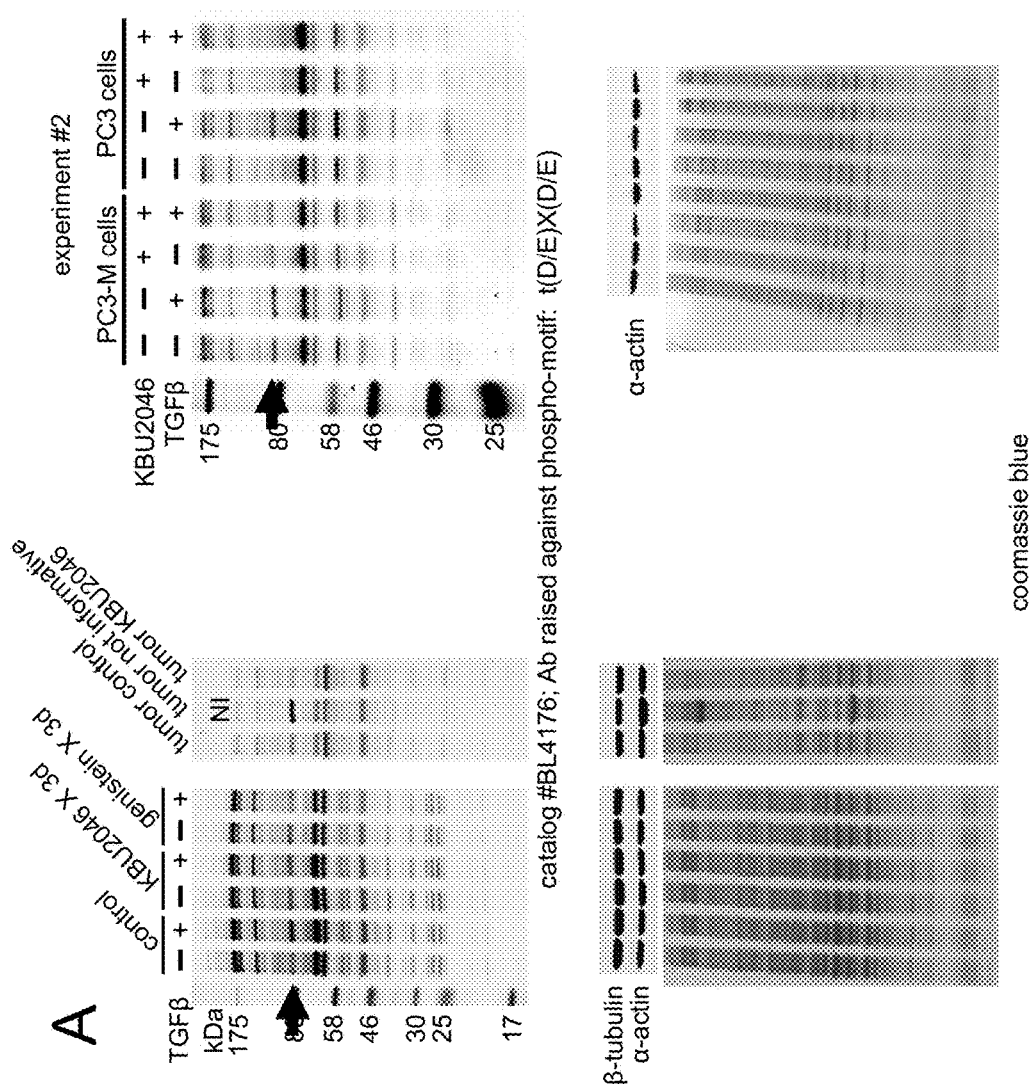
FIG. 14A-D. Proteomic analysis of the effects of KBU2046 on the kinome. Screening for effects on the kinome. PC3-M cells were pre-treated with 10 μM KBU2046, genistein or vehicle control for 3 days, then with ±TGFB, as indicated. Resultant cell lysate, as well as lysate from tumors from mice treated with 150 mg/kg KBU2046 or control mice (from manuscript FIG. 3A), were then probed with the KinomeView® panel of antibodies by Western blot. In instances where KBU2046 was inhibiting protein phosphorylation in cells and in tumors, a repeat experiment of PC3-M cells was conducted. In addition to including PC3-M cells, experiments were expanded to examine effects on PC3 cells. (A) The identification of an 83 kDa band of interest constitutes the only change that was repeatable across multiple experiments, and it was observed in PC3 and PC3-M cells, as well as in tumor tissue. (B) Bands of initial interest that did not repeat. (C,D) All other Western blots of phospho-motif antibodies that were evaluated on initial screen. NI=tumor not informative; this denotes a tumor sample that yielded an abnormal coomassie blue staining pattern.
Figure 14B:
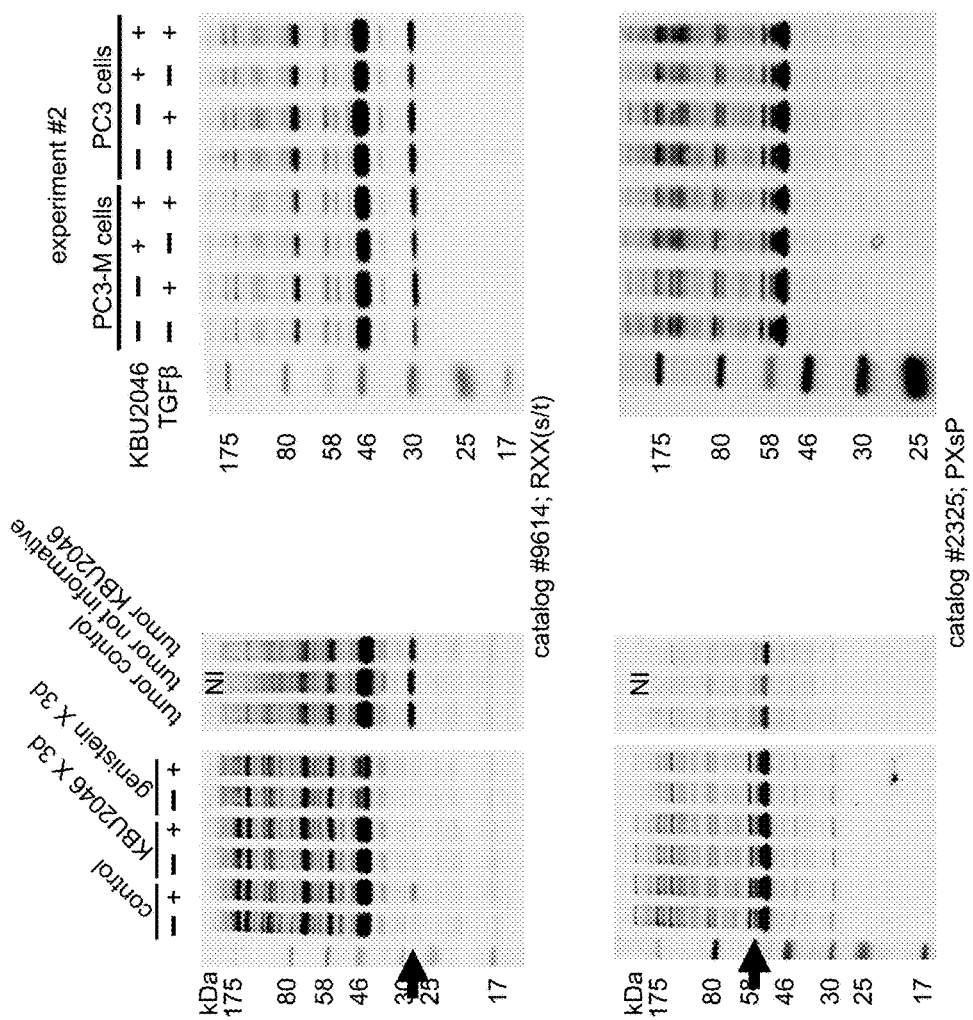
Figure 14C:
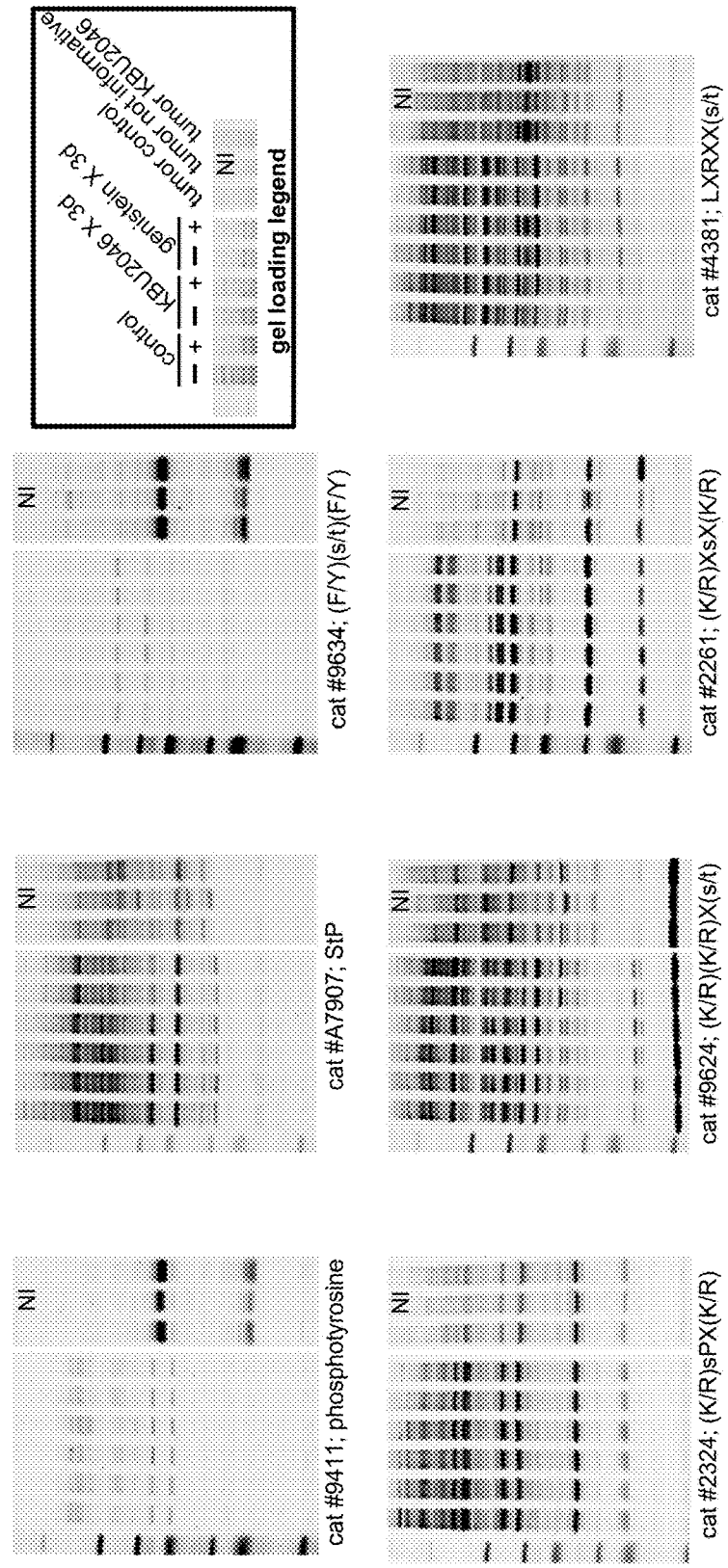
Figure 14D:
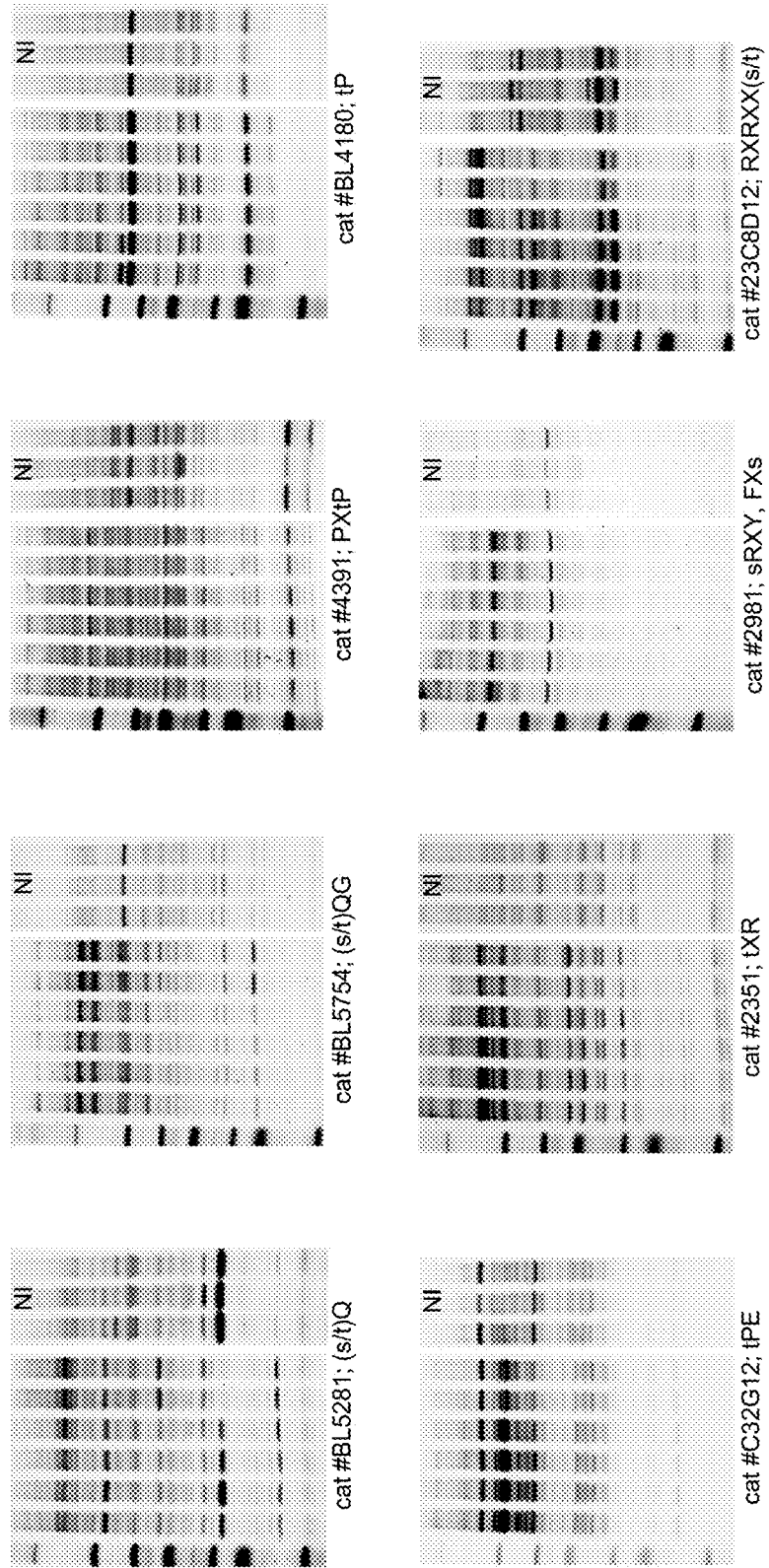

Probes were designed to contain chemical properties known to be associated with systemically active small molecules (FIG. 10) (Lipinski et al., 2001; herein incorporated by reference in its entirety). Employing an established orthotopic implantation murine model of human PCa metastasis (Lakshman et al., 2008; herein incorporated by reference in its entirety), the ability of KBU2046 to inhibit the formation of distant metastasis was quantified. KBU2046 significantly decreased metastasis in a dose-dependent manner by up to 92%, at plasma concentrations of 1.1-24 nM (FIGS. 3A, 3B). Comprehensive characterization of KBU2046 pharmacokinetics in mice demonstrated maintenance of plasma concentrations >24 nM for 9.3 hours after a single oral dose, and allowed characterization of pharmacokinetic parameters (FIG. 3C; FIG. 11). At the systemic level, KBU2046 was a highly selective inhibitor of metastasis. Comprehensive analysis of primary tumor growth, animal behavior, weight, histologic examination of multiple organs and serum chemistry profiling, failed to identify KBU2046-associated of f-target effects (FIG. 12, FIG. 13).

Figure 3D:
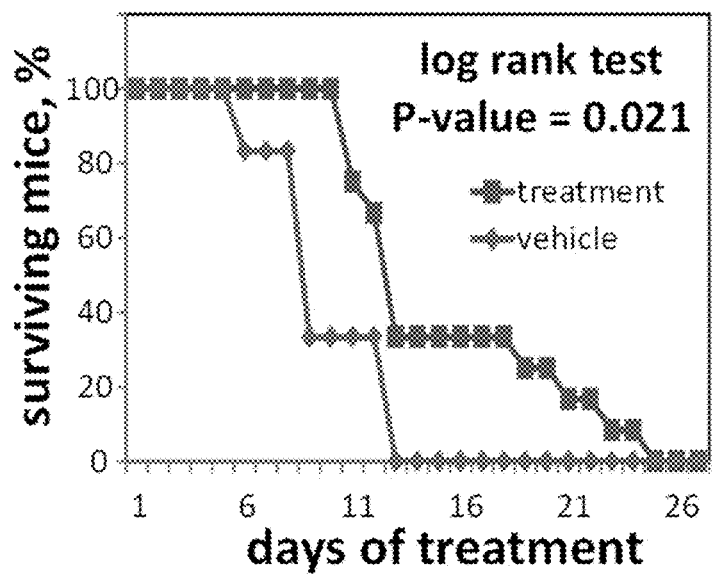
Figure 3C:
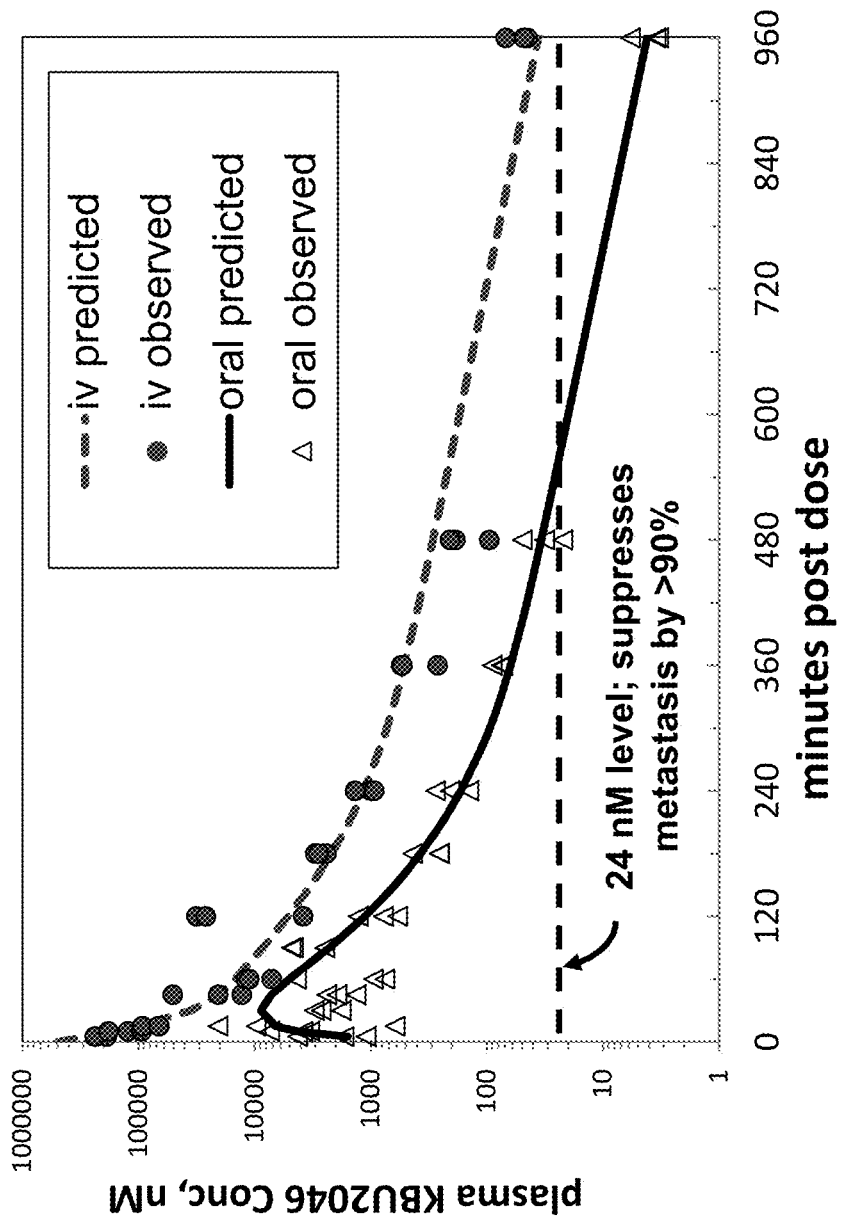

Recognizing the established link between metastasis and decreased survival in humans, the impact of KBU2046 on survival was assessed. The orthotopic PCa model exhibits rapid tumor growth around the urogenital tract, precluding assessment of the impact of metastatic burden on survival. However, orthotopic implantation of human breast cancer cells, followed by surgical removal of the resultant primary tumor, provides a murine model wherein survival is dictated by metastatic burden (du Manoir et al, 2006; herein incorporated by reference in its entirety). KBU2046 significantly prolonged the survival of mice treated in a post-surgery adjuvant setting (FIG. 3D).

KBU2046 Inhibits Invasion by Decreasing Phosphorylation of Ser226 on HSP90β

Low nanomolar concentrations of genistein inhibited the kinase activity of mitogen-activated protein kinase kinase 4 CMXK.41MAP2K4/MEK4) (Xu et al., 2009; herein incorporated by reference in its entirety), in turn inhibiting downstream phosphorylation of p38 MAPK (Huang et al., 2005; herein incorporated by reference in its entirety) and of heat shock protein 27 (HSP27) (Xu and Bergan, 2006; herein incorporated by reference in its entirety), which in turn inhibits MMP-2 expression and cell invasion in vitro, with systemic effects translating into inhibition of human PCa metastasis in mice (Lakshman et al., 2008; herein incorporated by reference in its entirety) and inhibition of MMP-2 expression in human prostate tissue (Xu et al., 2009; herein incorporated by reference in its entirety). In contrast to genistein, KBU2046 did not bind to MKK4 or inhibit its kinase activity in vitro, and it did not inhibit phosphorylation of p38 MAPK or of HSP27 in cells (FIG. 4). This finding, while surprising, demonstrates that the probe strategy de-selected for inhibition of the MKK4 signaling axis. This provides a measure of the unbiased nature of the small chemical probe strategy.

Figure 15:
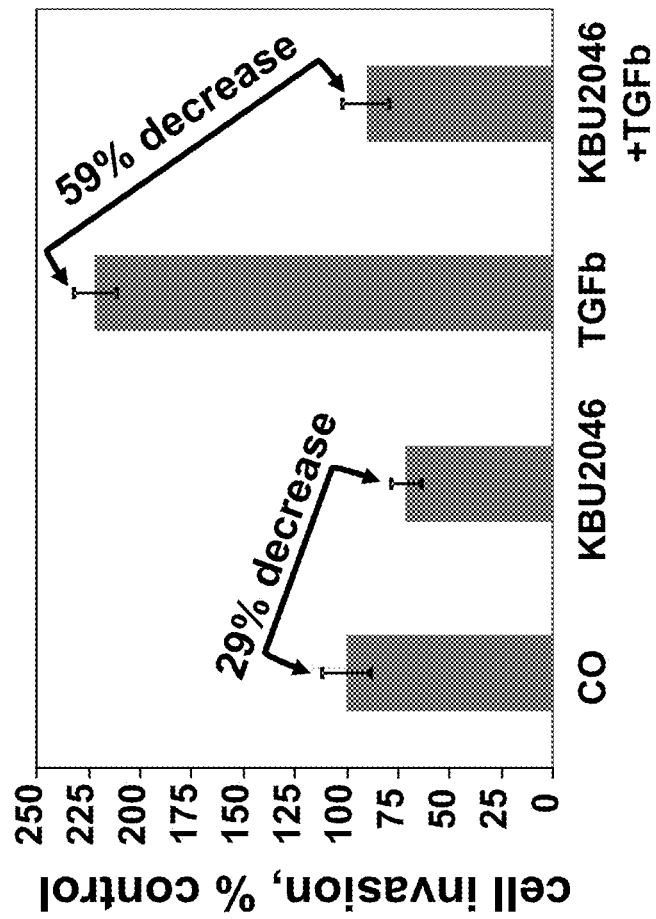
FIG. 15. KBU2046 exhibits greater efficacy under conditions of TGFβ treatment. The invasion of PC3-M cells pretreated with KBU2046 or vehicle control (CO) and then with ±TGFβ was measured.
Figure 17:
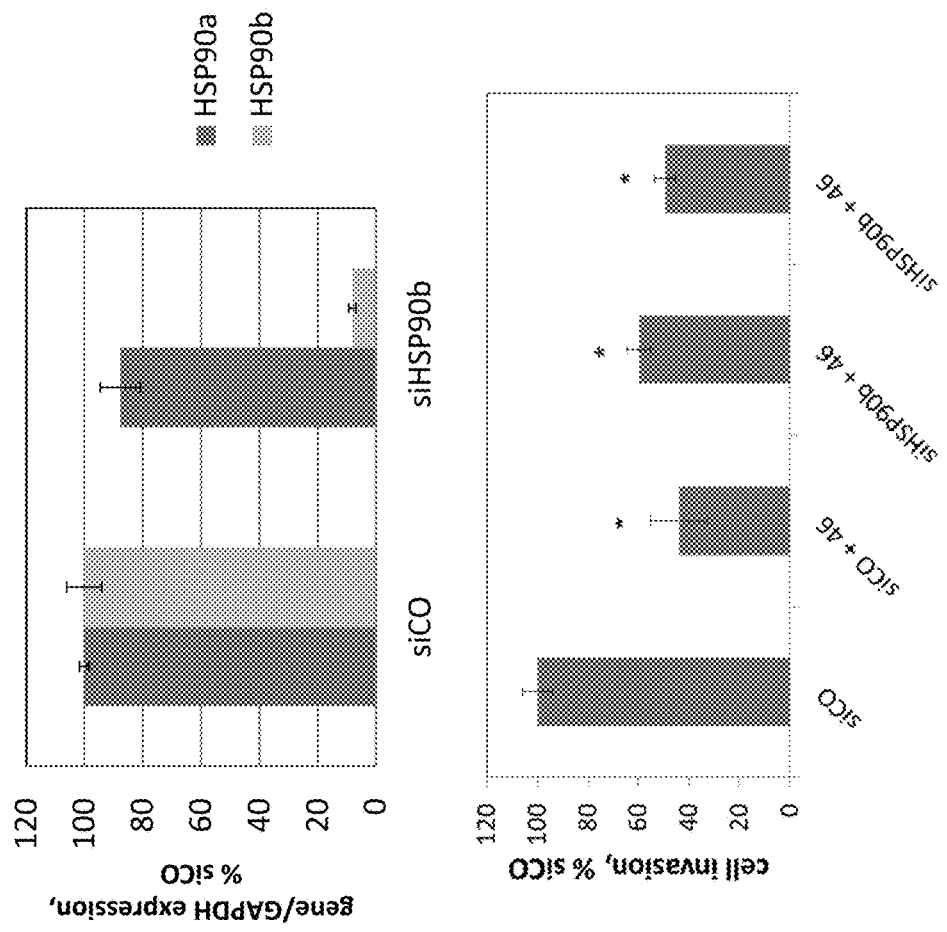
FIG. 17. Knockdown of HSP90β decreases cell invasion and abrogates KBU2046 efficacy. PC3-M cells were transfected with siRNA to HSP90β (siHSP90β) or non-targeting siRNA (siCO). (Top) The level of HSP90β and HSP90α (HSP90α) transcript levels were measured by qRTlPCR, and expressed relative to that of GAPDH. (Bottom) Cells were treated with KBU2046 (46) or vehicle control, and cell invasion measured. Values are the mean±SEM.

Because KBU2046 does not target MKK4, alternative methods for identifying its biological target(s) were pursued. The KinomeView® panel of antibodies (Cell Signaling Technology, Inc.) detects established protein phosphorylation motifs, and were was to probe for KBU2046-induced changes in protein phosphorylation (FIG. 5A; FIGS. 14A-D). Phosphoprotein changes that met the following criteria were prioritized: (1) changes were observed in cells and in tumors of treated mice (from FIG. 3A), (2) changes counteracted transforming growth factor β (TGFβ)-induced effects, and that were reproducible. TGFβ is ubiquitous in vivo, is known to increase PCa cell invasion (Huang et al., 2005; herein incorporated by reference in its entirety), and KBU2046's anti-invasion efficacy is greater in the presence of TGFβ (FIG. 15). Genistein was evaluated under identical treatment conditions for comparison. Its many pharmacologic effects induced widespread changes in protein phosphorylation (FIG. 14A-D). In contrast, with KBU2046, only a decrease in intensity of an 83 kDa protein band met the pre-specified criteria (arrow in FIG. 5A). The high molecular selectivity of KBU2046 was further supported by its failure to inhibit over 400 different protein kinases and 20 phosphatases examined, in three different in vitro assay systems.

Figure 5A:
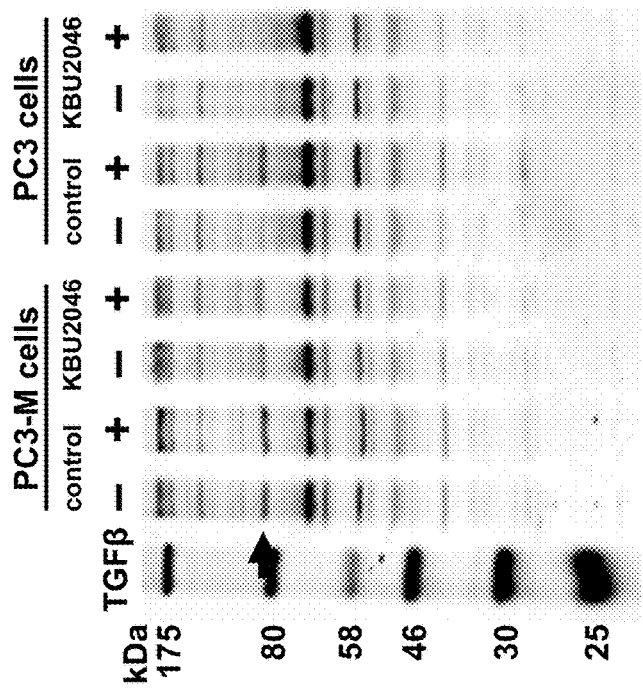
FIGS. 5A-D. HSP90 β $Ser^{226}$ phosphorylation is identified as a regulator of cell invasion and a mediator of KBU2046 efficacy. (A) Probing for KBU2046-induced changes in protein phosphorylation. PC3-M or PC3 cells were pre-treated with KBU2046, then with ±TGFβ and the resultant cell lysate probed for changes in protein phosphorylation with the KinomeView® assay. The depicted Western blot utilizes KinomeView® phospho-motif antibody, BL4176; the arrow denotes an 83 kDa band whose phosphorylation is inhibited by KBU2046. (B) Proteomic analysis. PC3 cells were pre-treated with KBU2046 or vehicle, then with TGFβ, proteins from the resultant cell lysate were immunoprecipitated with BL4176, and HSP90β was identified by LC-MS/MS analysis. The phospho-motif recognized by the antibody is underlined; S*—denotes Ser226, phosphorylation of which is decreased by KBU2046. (C, D) The phosphorylation status of HSP90β $Ser_{226}$ regulates human PCa cell invasion and is necessary for KBU2046 action. PC3-M cells were transfected with S226A-, S226D-, or WT-HSP90β, or empty vector (VC), treated with KBU2046 or vehicle, and cell invasion measured. Values are the mean±SEM of a representative experiment of multiple experiments.
Figure 5B:
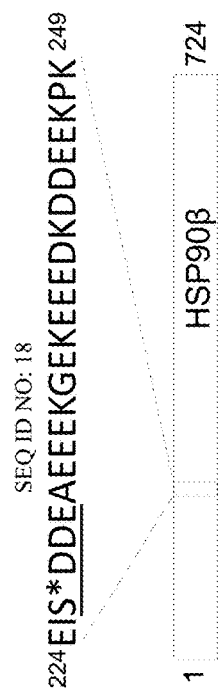

The 83 kDa protein was identified by pretreating PC3 cells with KBU2046 or vehicle control, treating with TGFB and performing LC-MSIMS analysis on proteins pulled down by the KinomeView® antibody used in FIG. 5A. Resultant data were analyzed with a SEQUEST/Sorcerer data analysis suite (Lundgren et al., 2009; herein incorporated by reference in its entirety), and proteins further selected based upon predetermined parameters, including expression at >1=3× background levels, exhibiting a >1=2.5 fold decrease with KBU2046 and within ±5 kDa of the 83 kDa index band. This approach yielded a single protein, HSP90β, and indicated that KBU2046 decreased the abundance of phosphorylated Ser226 on HSP90β by 6.6 fold (FIG. 5B; FIG. 16).

Figure 5C:
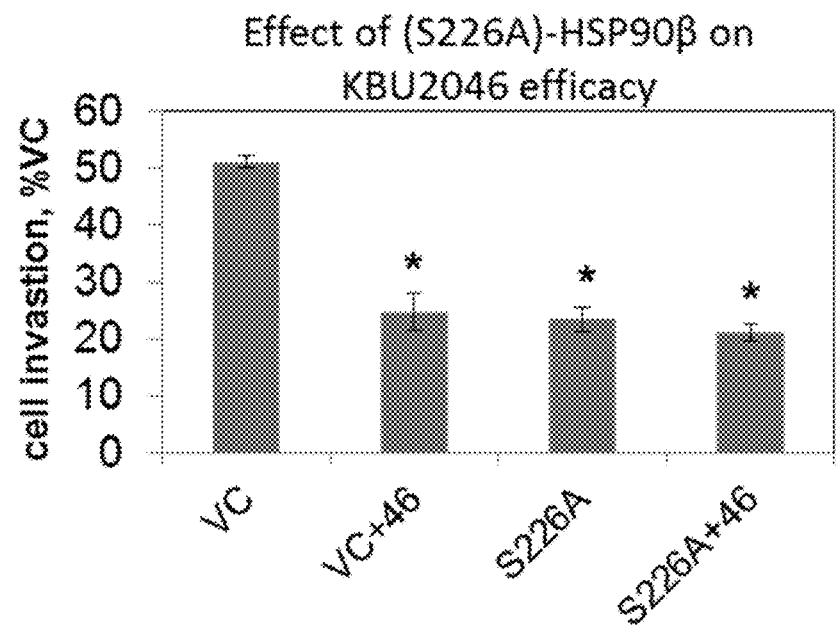
Figure 5D:
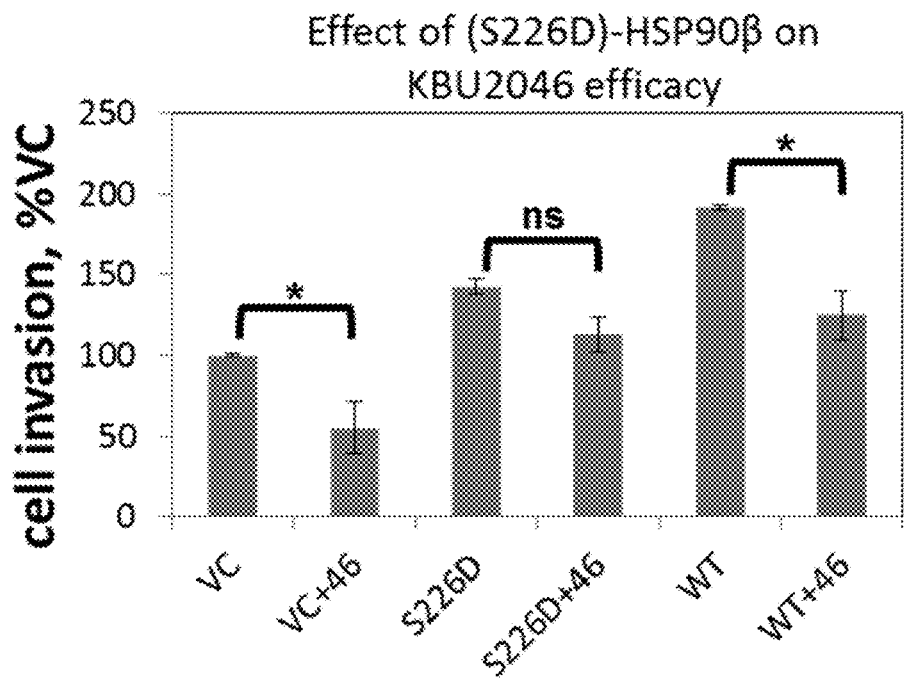

Using a (S226A)-HSP90β construct, we demonstrated that loss of Ser226 inhibited cell invasion compared to wild type (WT)-HSP90 β, and that its loss abrogated KBU2046 efficacy (FIG. 5C). The selectivity of HSP90B in mediating KBU2046 efficacy was further supported by demonstrating that siRNA-mediated HSP90 β knockdown inhibited cell invasion and abrogated KBU2046 efficacy (FIG. 12). Importantly, HSP90 β-specific siRNA did not knockdown HSP90α. We next demonstrated that cells transfected with (S226D)-HSP90β, which provides a biological mimic of phosphorylated Ser226, exhibited increased invasion and were not sensitive to the effects of KBU2046 (FIG. 5D). These findings identify phosphorylation of HSP90β Ser226 as a regulator of cell invasion, and demonstrate that it is necessary and sufficient for mediating KBU2046 efficacy.

KBU2046 Binds to the CDC37/HSP90β Heterocomplex

With phosphorylation of HSP90β $Ser^{226}$ identified as the regulator of KBU2046 action, we sought to gain further insight into the interaction between KBU2046 and its protein target(s). Along with HSP90β, we considered CDC37 as a possible target. CDC37 is a co-chaperone that mediates the binding of over 350 client proteins to HSP90β, including over 190 kinases (Taipale et al., 2012; herein incorporated by reference in its entirety). The flexible arm-like structure of CDC37 (protein data bank (PDB) ID: 2WOG) enables dynamic binding of large numbers of kinases, and defines their positioning relative to $Ser^{226}$. Another measure of CDC37's mobile nature is that its conformational changes are coupled to that of the highly dynamic HSP90 chaperone cycle (Vaughan et al., 2006; herein incorporated by reference in its entirety). The coordinated and dynamic movements of CDC37 and HSP90β dictate the spectrum of kinases that are juxtaposed to, and able to modulate, $Ser^{226}$ phosphorylation status. It was reasoned that if KBU2046 bound to either CDC37 or HSP90β, the new chemical interactions that resulted could alter the dynamics and functions of these two proteins, thus regulating kinase accessibility to $Ser^{226}$ and its phosphorylation.

Figure 6A:
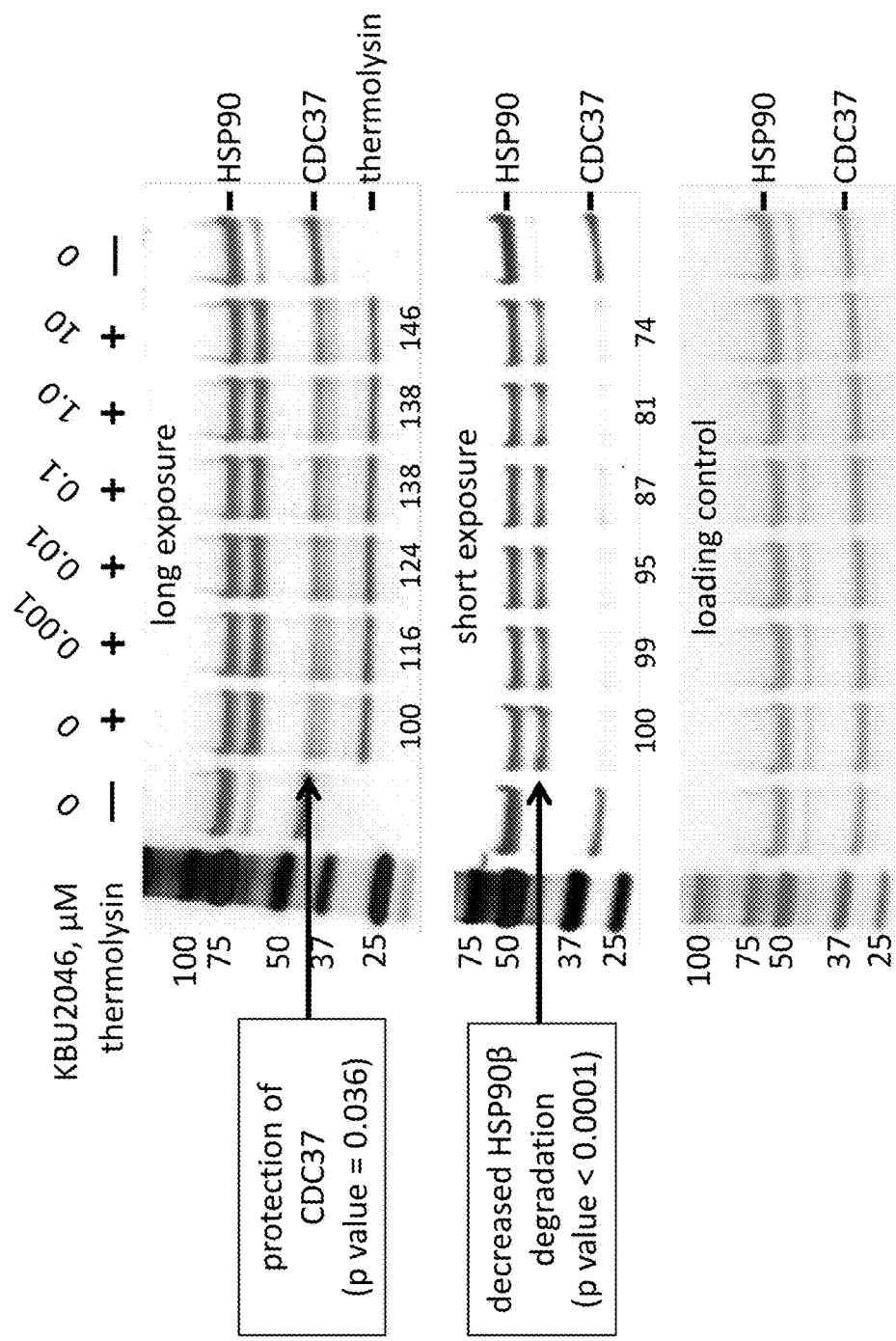
FIGS. 6A-D. KBU2046 stabilizes CDC37/HSP90β heterocomplexes. (A) KBU2046 stabilizes HSP90β/CDC37 heterocomplexes in a DARTS assay. Equimolar amounts of HSP90B and CDC37 protein were pre-incubated with KBU2046, and resultant themlolysin reaction products were detected by silver stain following SDS-PAGE. The mean value of protein bands indicated by arrows is displayed below each lane, and are expressed as the percentage of untreated controL ANOYA P values for changes in band intensity with concentration are displayed. (B) In-silico model of CDC37 and HSP90β depicting KBU2046 hydrogen bonding with Gln119 of HSP90β. (C) Lipophilic potential surface of the computed ligand binding pocket of the CDC37/HSP90β model with KBU2046 bound. (D) Potential surface of the whole CDC37/HSP90β dimer.
Figure 18:
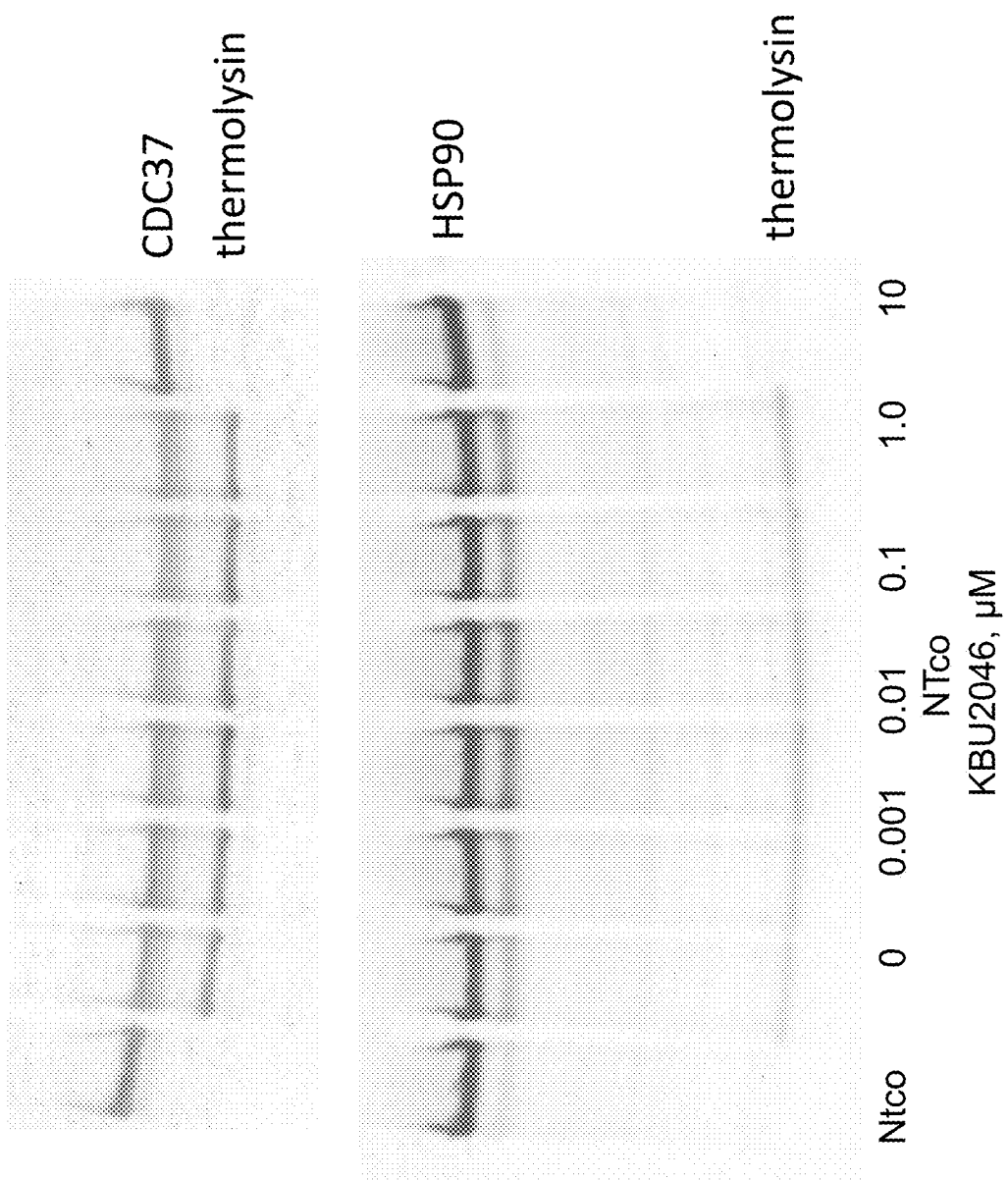
FIG. 18. KBU2046 does bind HSP90β or CDC37. Studies used purified recombinant HSP90B or CDC37. There was no evidence of KBU2046 binding to either HSP90β or CDC37 as measured by isothermal titration calorimetry or by fluorescence-based thermal shift assay. For DARTS assay, HSP90β or CDC37 were individually pre-incubated with KBU2046, thennolysin added, and reaction products were separated by SDS PAGE and visualized by silver stain (depicted above). NTco=no thennolysin control.
Figure 19A:
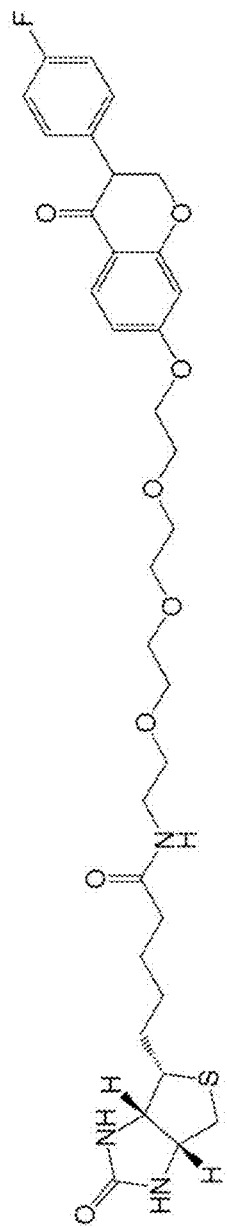
FIGS. 19A-D. KBU2046 binds to intact cells, but not to isolated proteins. (A) Chemical structure of KBU2046 linked to biotin (KBU2046-biotin). (B) KBU2046-biotin is biologically active. PC3-M cells were pre-treated with 10 μM KBU2046 or with KBU2046-biotin for three days, and single cell motility assays conducted. Data are the mean±SEM. (C) KBU2046-biotin labels cells in a manner that can be competed off. PC3-M cells were labeled with 1 KBU2046-biotin+/−10 μM free KBU2046, followed by detection with FITC-streptavidin, and visualization by fluorescent microscopy (with equal exposure times). (D) Protein array hybridization. KBU2046-biotin was hybridized to ProtoArray® Human Protein Microarray's at 0.5 and 10 μM with and without 10-fold excess free KBU2046. Proteins were first sought that met the following criteria, and did so at both 0.5 and 10 μM concentrations of KBU2046-biotin (in the absence of free KBU2046): Z-Score greater than 2.5, Z-Factor greater than 0.5, CI P-value less than 0.05, negative control value <2,000 (relative fluorescence units; RFUs), and a signal/negative control signal of >10 and >5 for 10 μM and 0.5 μM conditions, respectively. This yielded 3 proteins, shown in table, for an initial hit rate of 0.03%. It was then required that free KBU2046 inhibit binding by >75% of the two remaining candidates, eliminating isovaleryl-CoA dehydrogenase (ICD). Its binding signal doubled on going from 0.5 to 10, while percent competition by free KBU2046 markedly decreased; non-specific binding was suspected by the biotin-linker moiety. The positive control used in protein arrays was staurosporine. Staurosporine is similar to genistein in that both are small compound natural products that are broad spectrum kinase inhibitors. In contrast to the lack of binding by KBU2046-biotin, staurosporine bound to 214 proteins at levels that were >/=10 fold above that of background. The vast majority of these proteins were kinases. Both HSP90 β and CDC37 were present on the protein arrays, and were not bound by KBU2046-biotin.
Figure 19B:
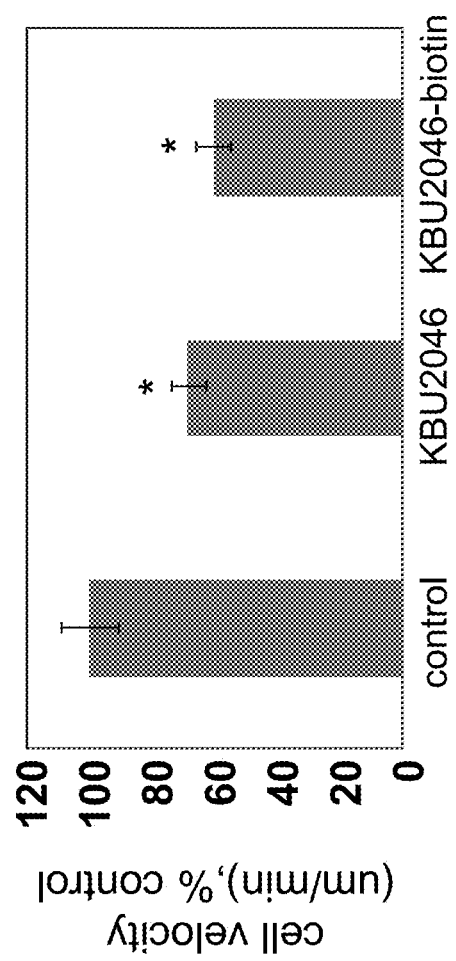
Figures 19C, 19D:

There was no evidence of KBU2046 binding to either CDC37 or HSP90β by isothennal titration calorimetry, by fluorescence-based thermal shift assay, or by drug affinity responsive target stability (DARTS) assay (FIG. 18) (Lomenick et al., 2009; herein incorporated by reference in its entirety). DARTS provides a sensitive measure of ligand-induced changes in protein structure and dynamics by measuring the ability of a ligand to protect its target from protease digestion (Lomenick et al., 2009; herein incorporated by reference in its entirety). Although KBU2046 did not bind CDC37 or HSP90β individually, CDC37 and HSP90β associate to form a tetrameric hetero-complex (Vaughan et al., 2006; herein incorporated by reference in its entirety). In a DARTS assay combining CDC37 and HSP90β, KBU2046 protected both proteins from digestion (FIG. 6A). The intensity of CDC37 increased, that of the HSP90β degradation product decreased, and both effects were statistically significant, concentration-dependent and were evident at 100M. The high selectivity of KBU2046 for protein binding was further supported by synthesizing a biotin chemical linker to KBU2046, demonstrating that it retained biological activity, demonstrating that it bound to intact cells (e.g., under physiological conditions of CDC37/HSP90β heterocomplex formation), and demonstrating that it failed to bind to an array of over 9,000 human proteins (FIG. 19A-D).

Together, these findings demonstrate that KBU2046 is operating in a distinct fashion from that of classical HSP90 inhibitors (Neckers and Workman, 2012; Whitesell et al., 2012; herein incorporated by reference in its entirety). Instead of binding directly to HSP90α and inhibiting the chaperone cycle, which in turn induces cytotoxicity, KBU2046 inhibits phosphorylation of HSP90βSer$^{226}$. This residue is not present on HSP90α. Further, KBU2046 does not bind to isolated HSP90β, nor does it induce cytotoxicity. Finally, and importantly, KBU2046 binds to and stabilizes the CDC37/HSP90β heterocomplex.

Figure 6B:
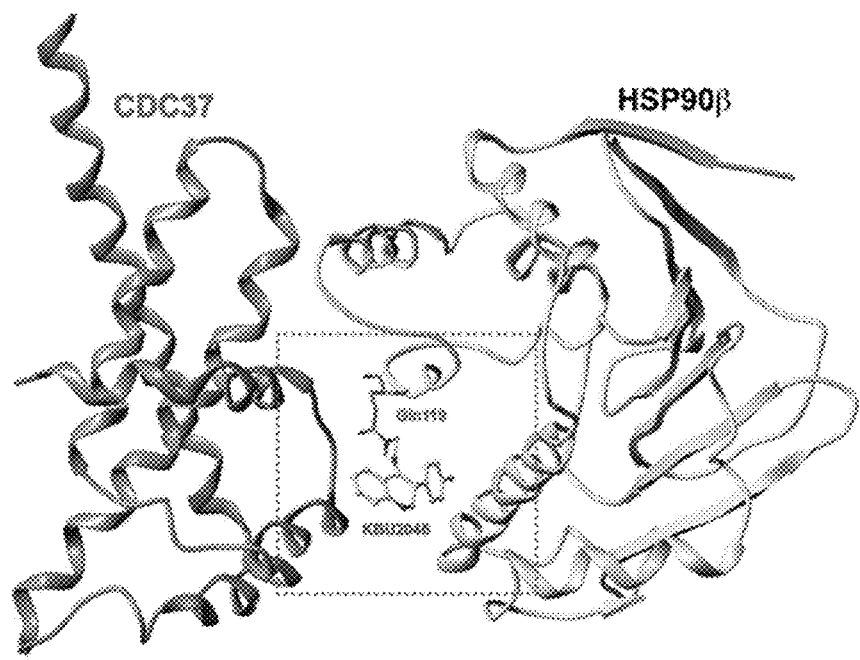
Figure 6C:
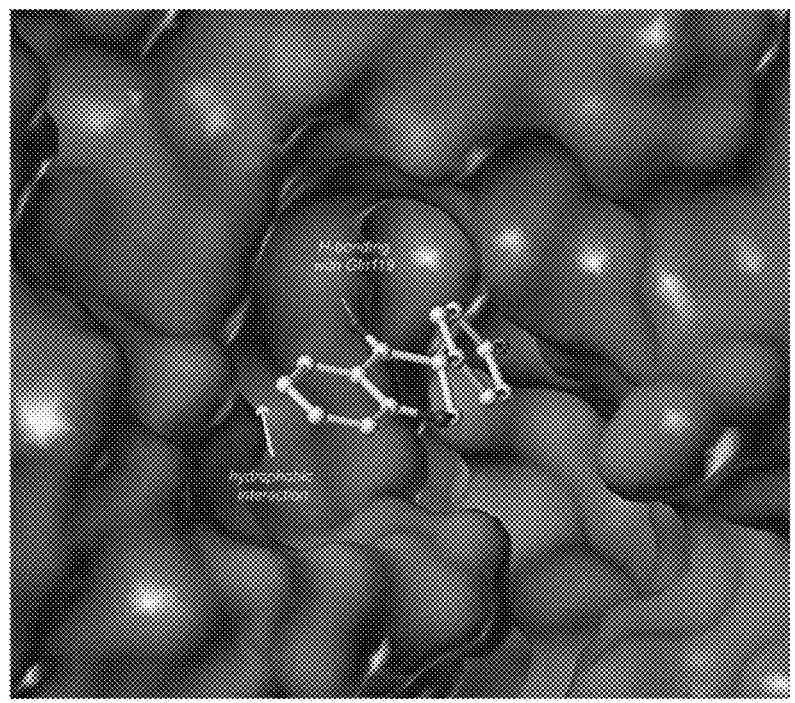
Figure 6D:
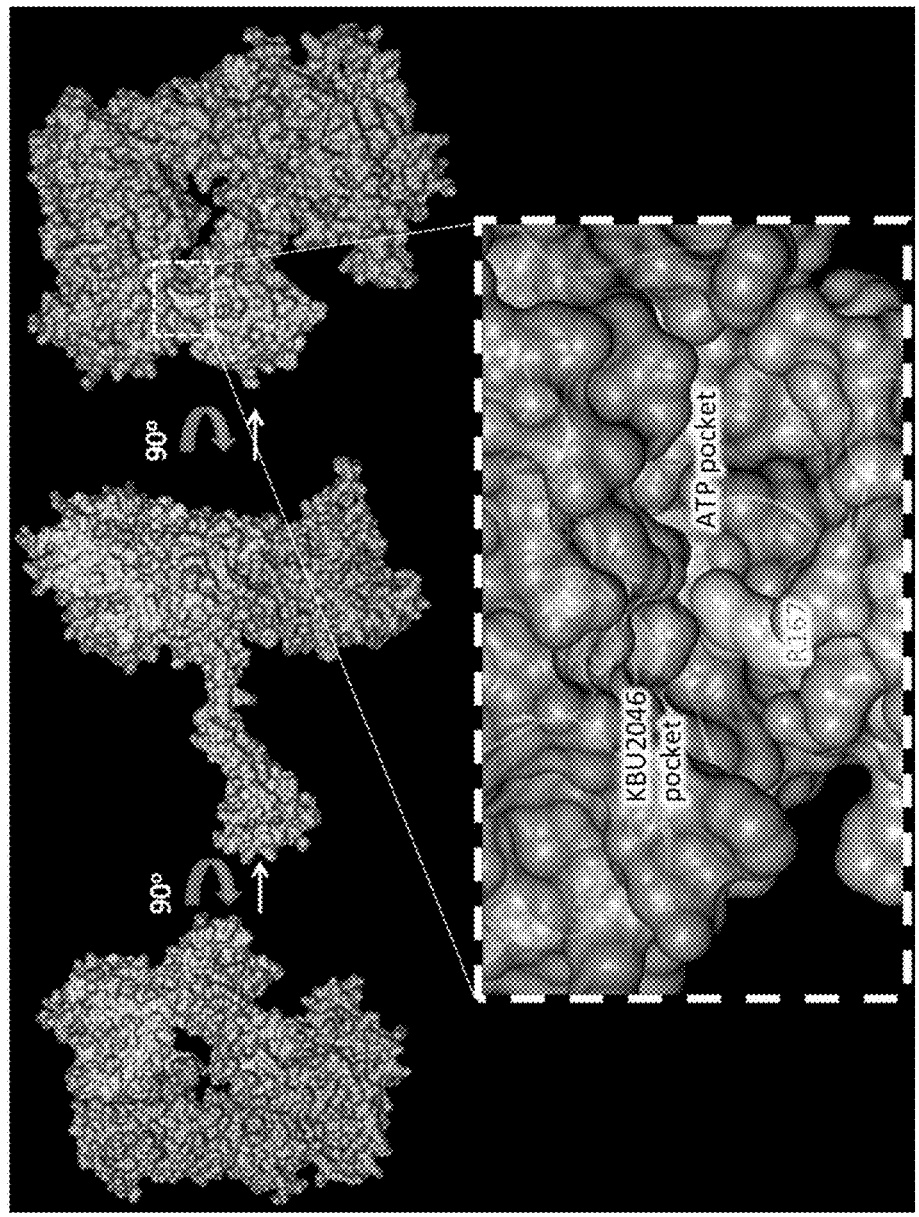
Figure 7A:
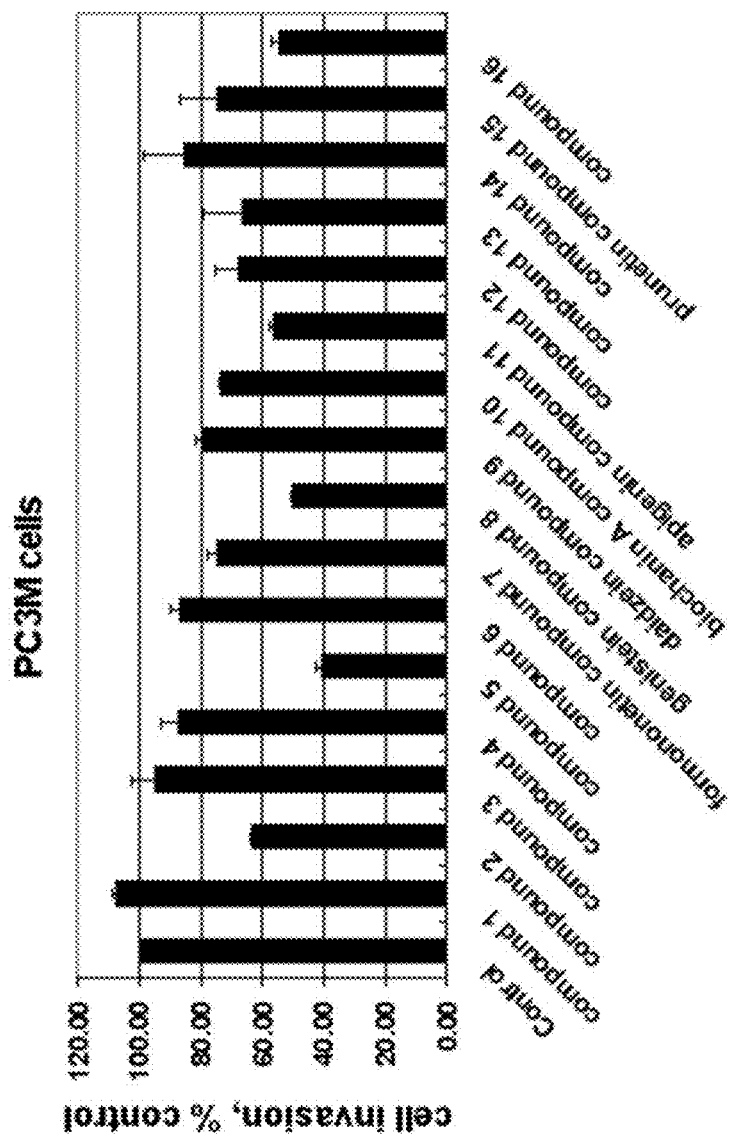
FIG. 7A-U. Exemplary synthesis of KBU2046.
Figure 7B:
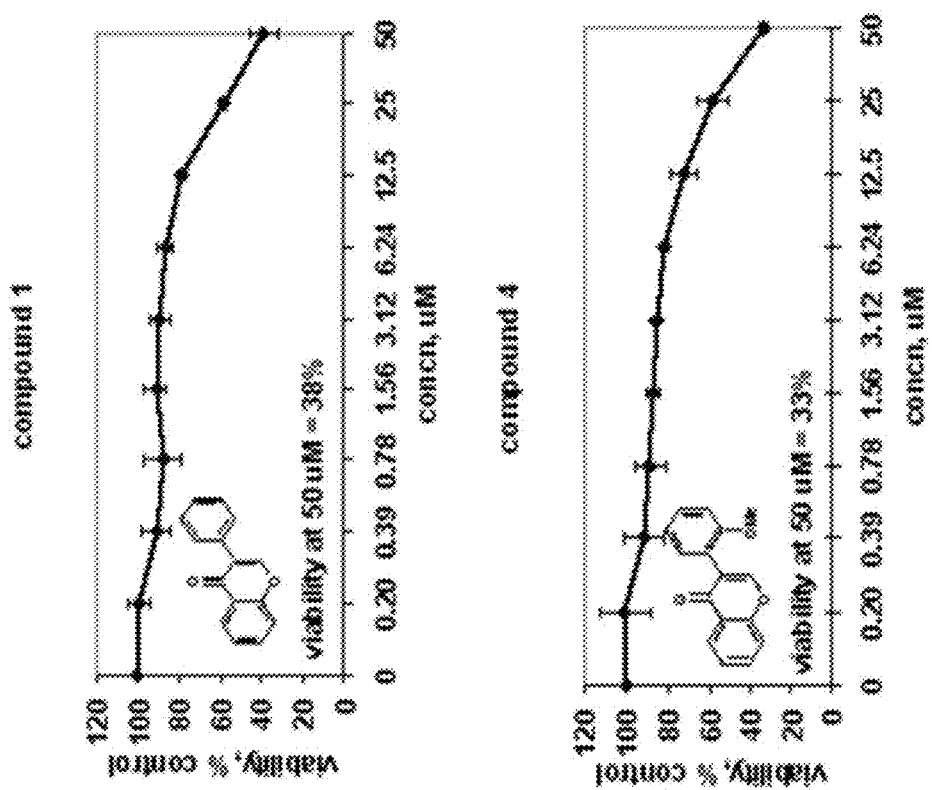
Figure 7C:
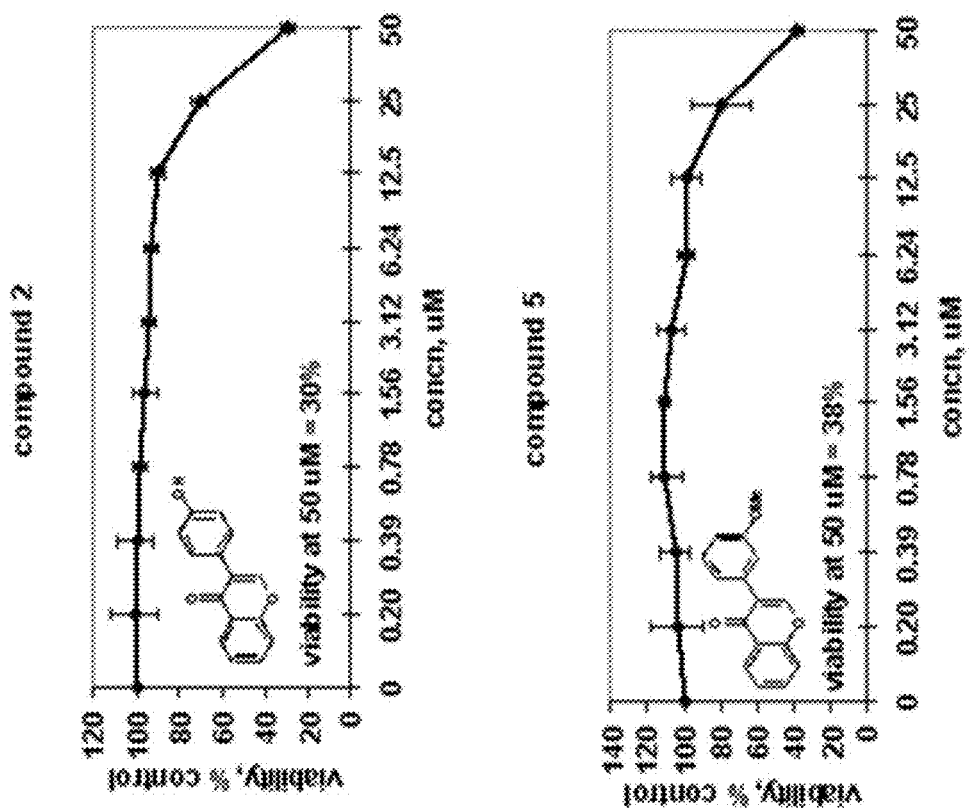
Figure 7D:
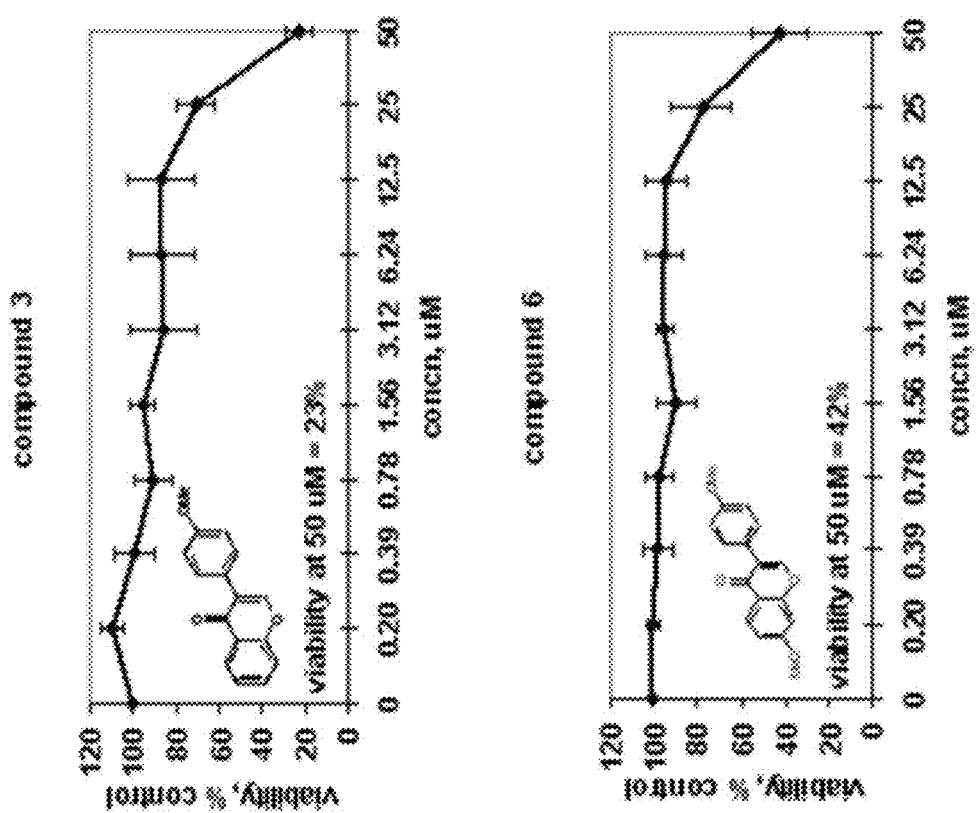
Figure 7E:
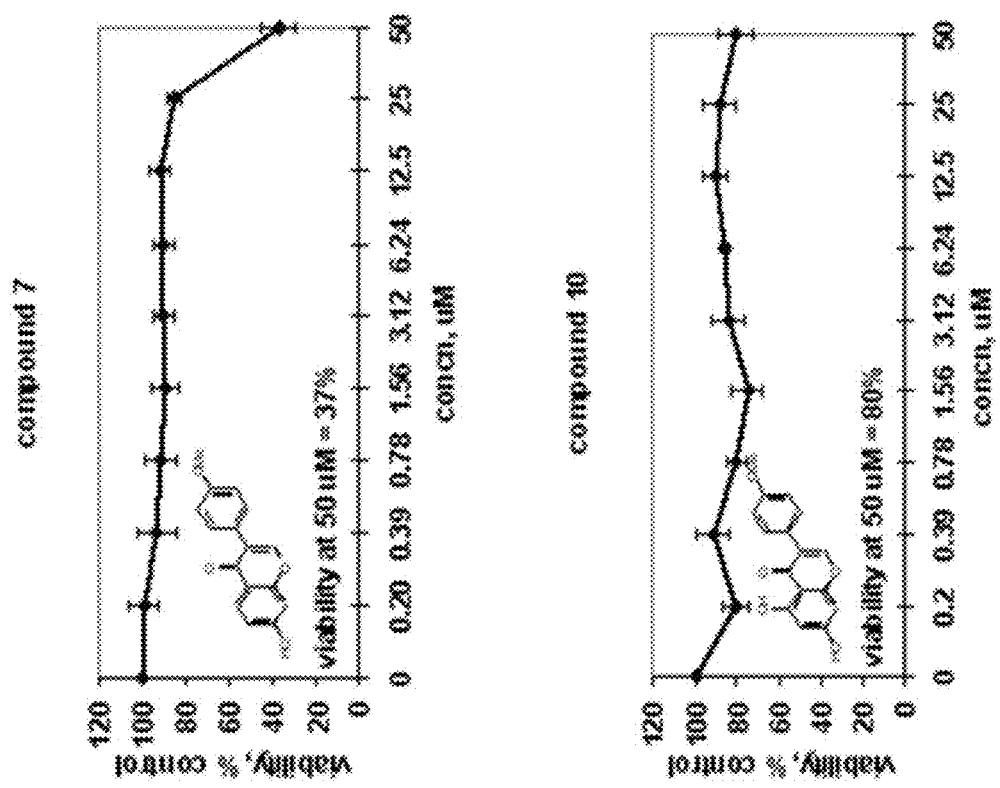
Figure 7G:
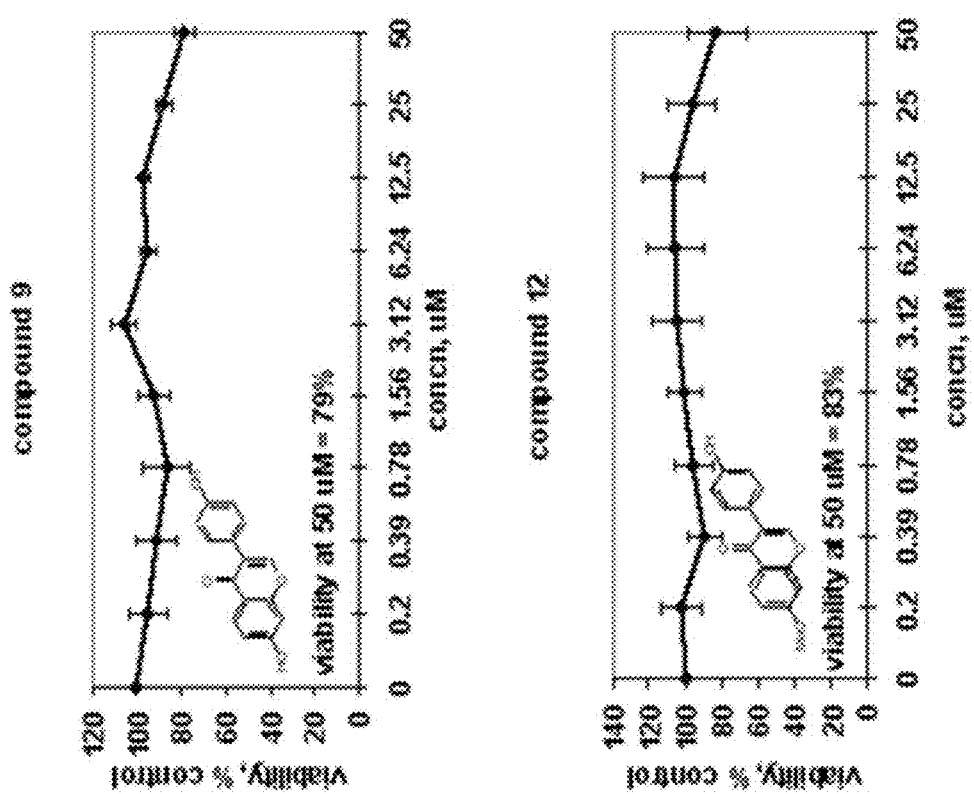
Figure 7H:
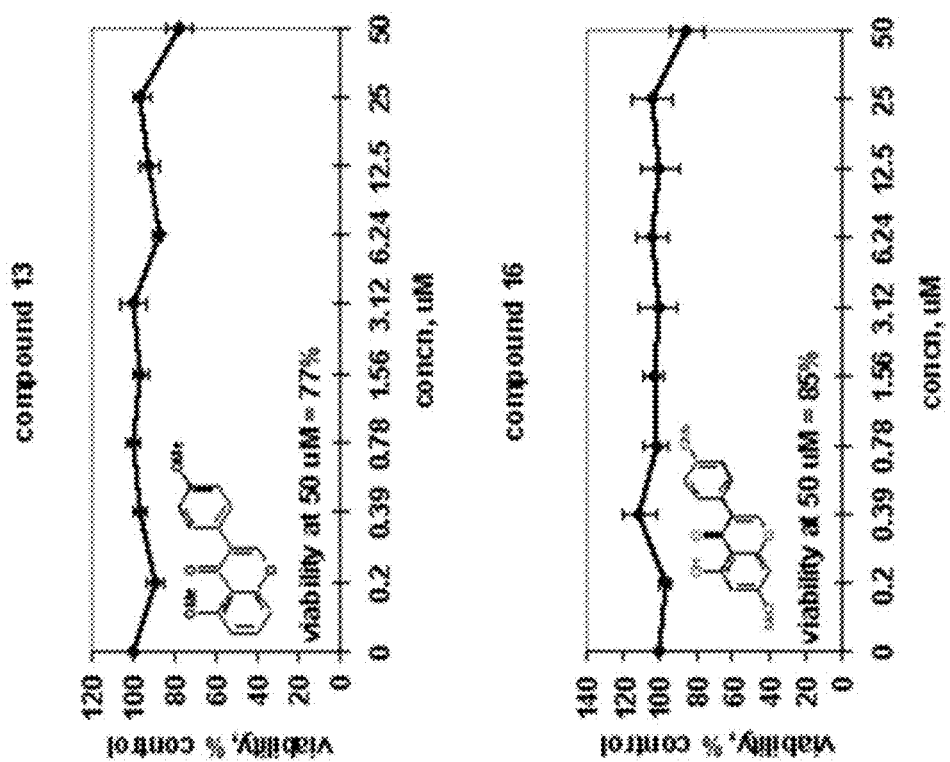
Figure 7I:
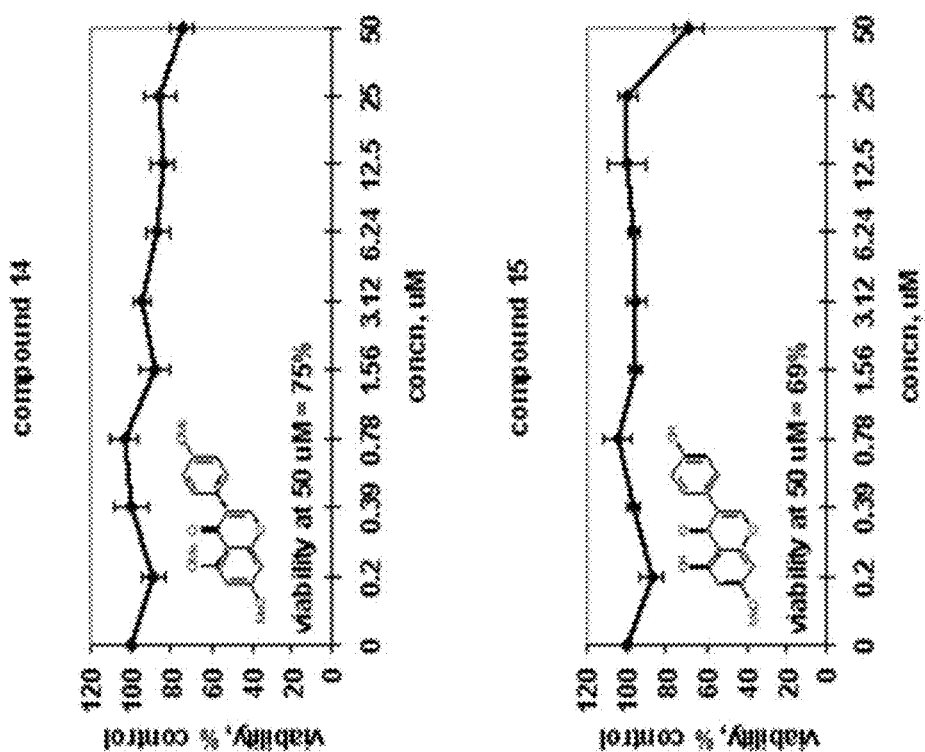
Figure 7J:
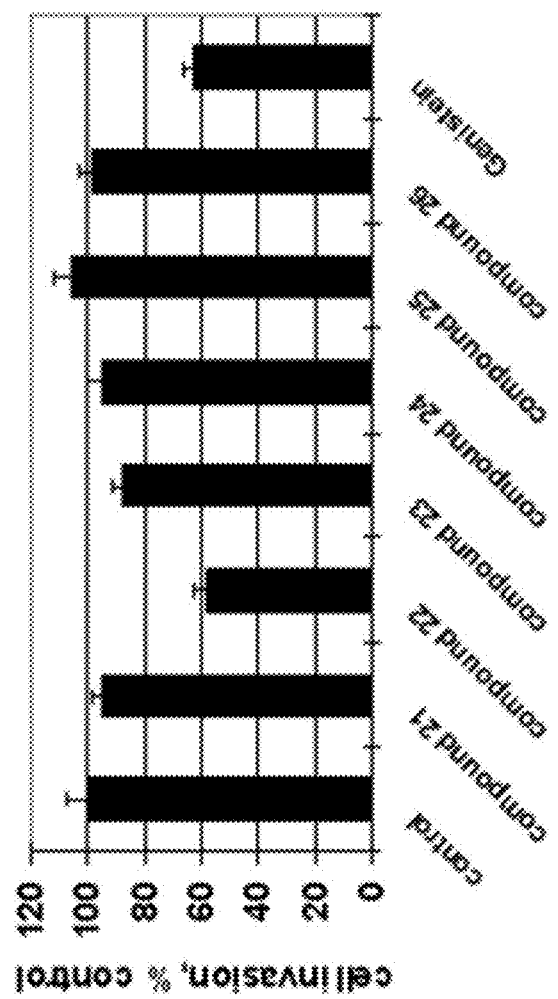
FIGS. 7J-M. Synthetic round #2. Initial structure-activity relationship (SAR) data informed the second round of compound synthesis. Key biological findings: it is possible to retain anti-invasion efficacy while having minimal effect upon cell growth inhibition (compound 22). Additionally, reduction of the C2-C3 double bond does not confer loss of activity (compound 22) and appears to reduce off-target cell toxicity. Other findings: moving the C4 carbonyl group to generate the coumarin core confers loss of activity (e.g., compounds 23, 24 and 25).
Figure 7K:
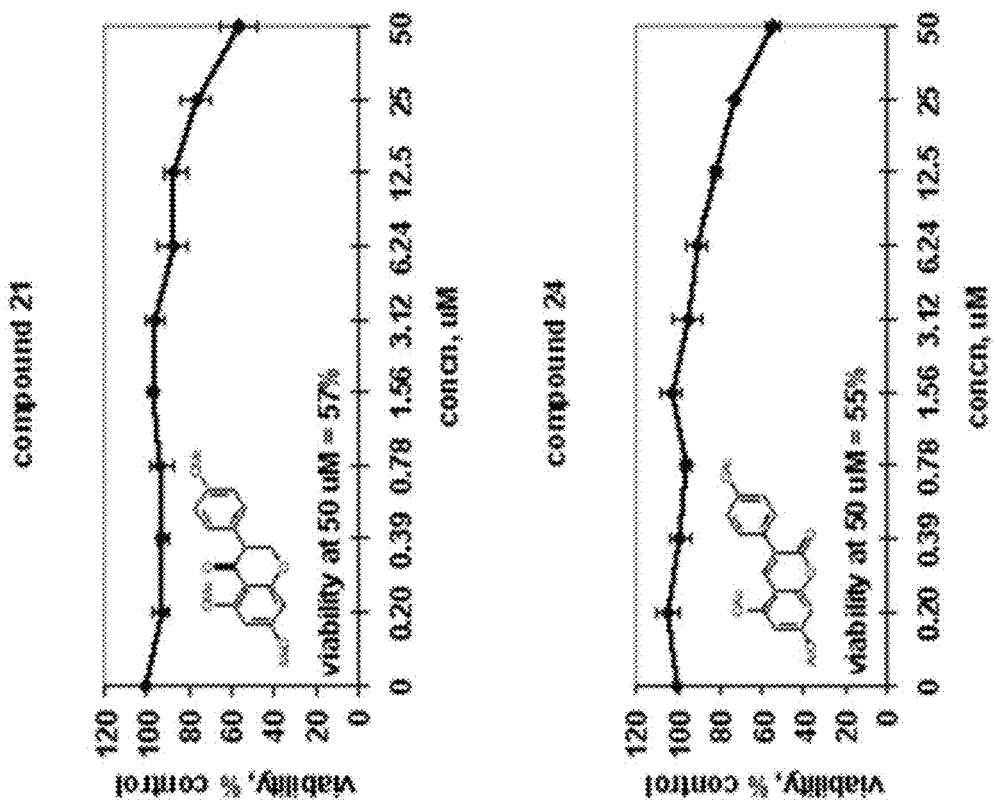
Figure 7L:
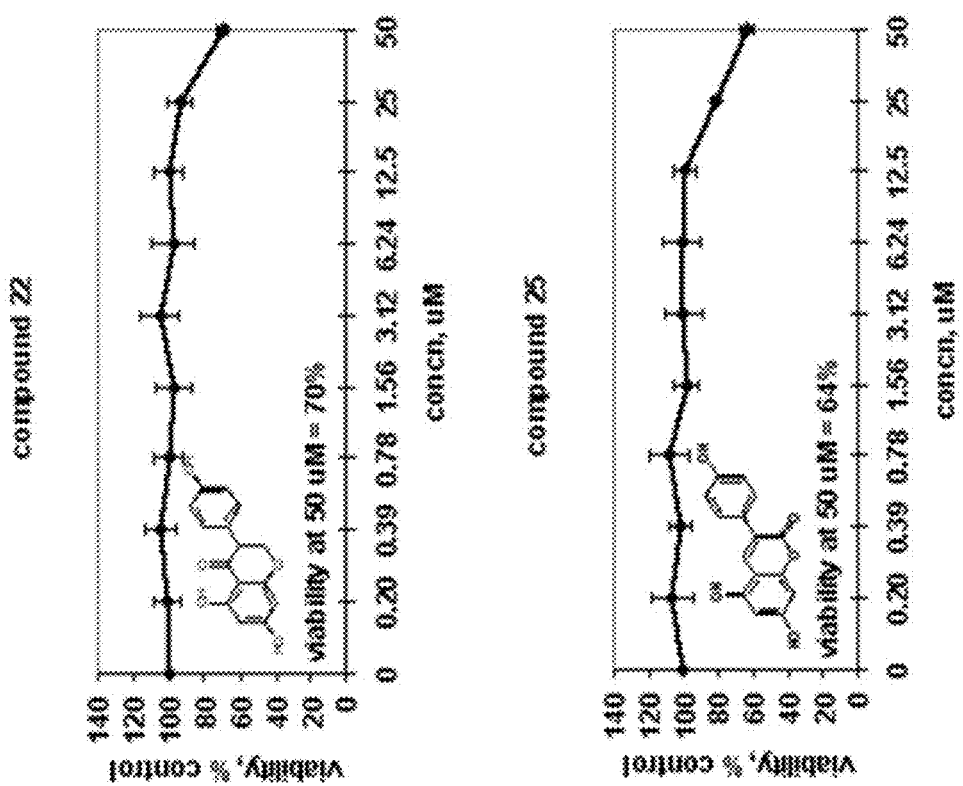
Figure 7M:
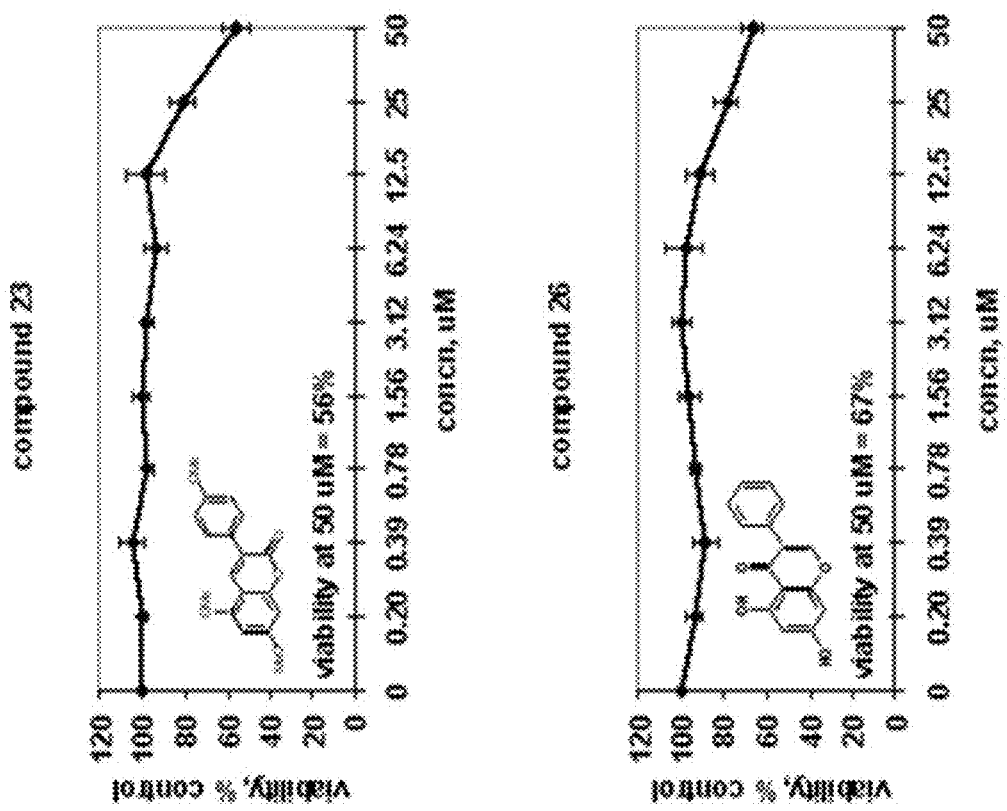
Figure 7N:
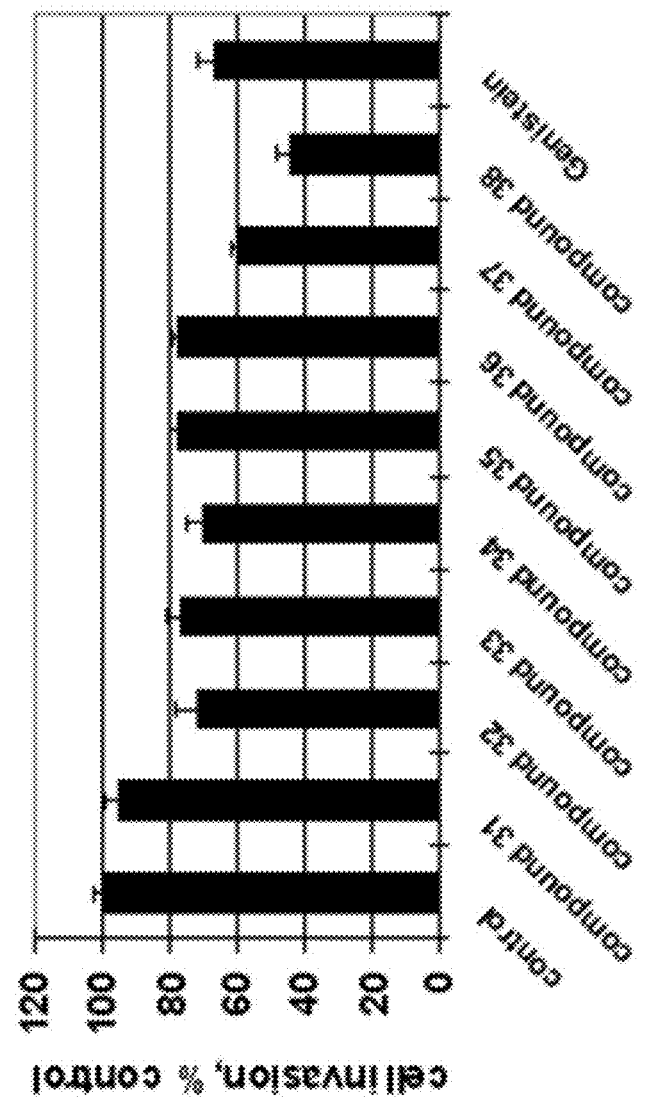
Figure 7Q:
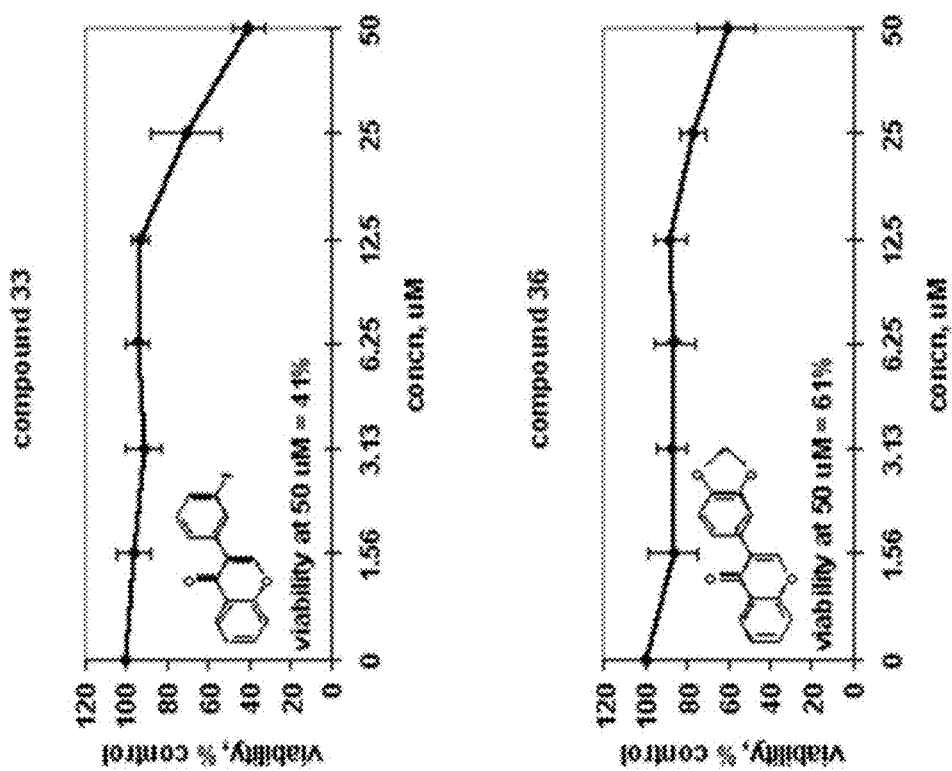
Figure 7R:
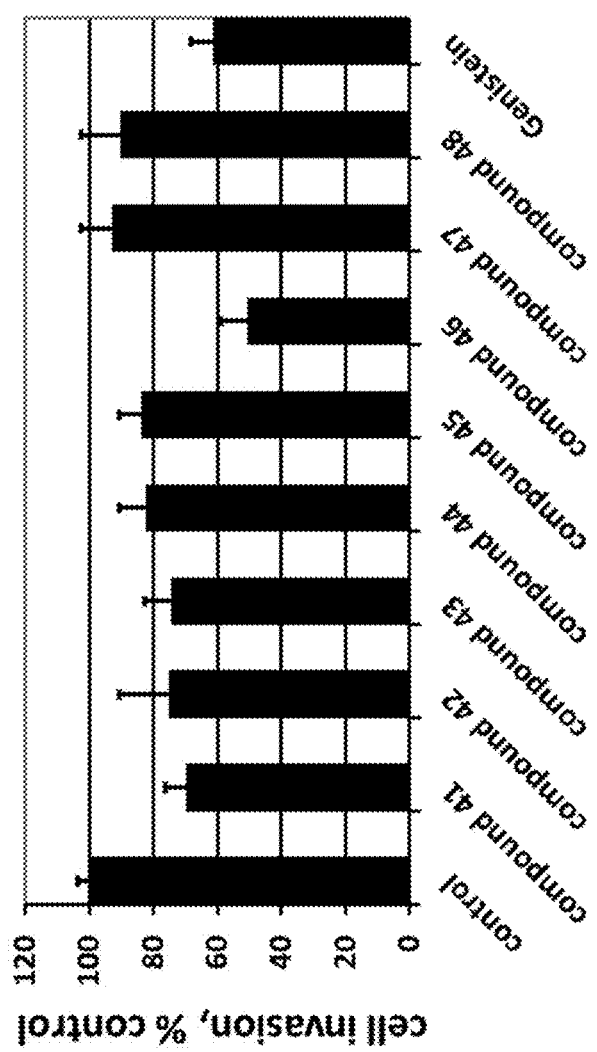
Figure 7U:
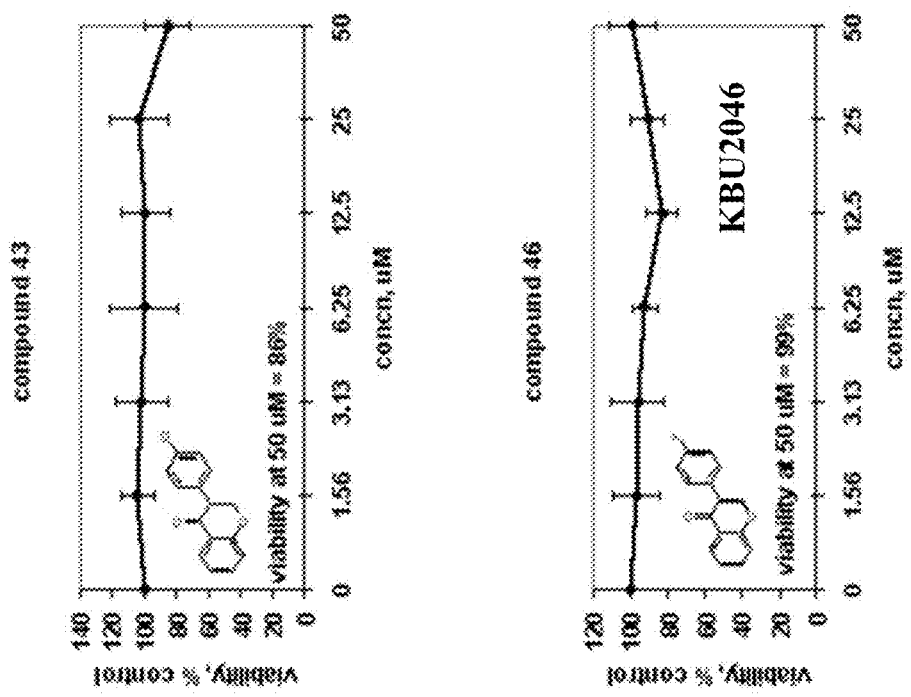
Figure 8:
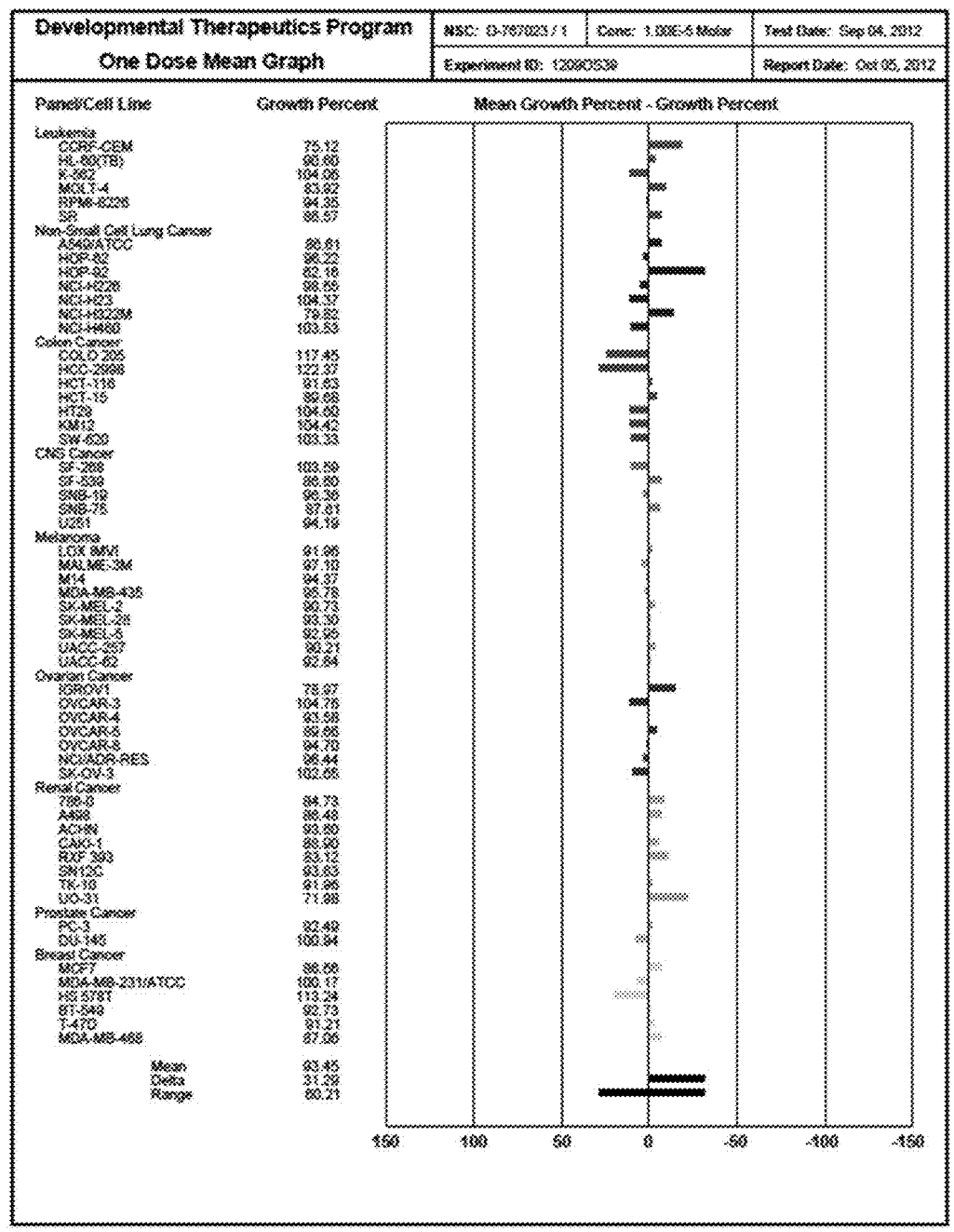
FIG. 8. KBU2046 has minimal-to-no cell toxicity in the NCI 60 cell line panel. KBU2046 was submitted to the Developmental Therapeutics Program (DTP) of the US National Cancer Institute (NCI), underwent initial screening across the NCI 60 cell line panel per DTP protocol (Shoemaker, 2006; herein incorporated by reference in its entirety), and the resultant COMPARE diagram is depicted. Based upon its lack of cell toxicity, NCI did not select KBU2046 to go on to multi-dose testing.
Figure 20:
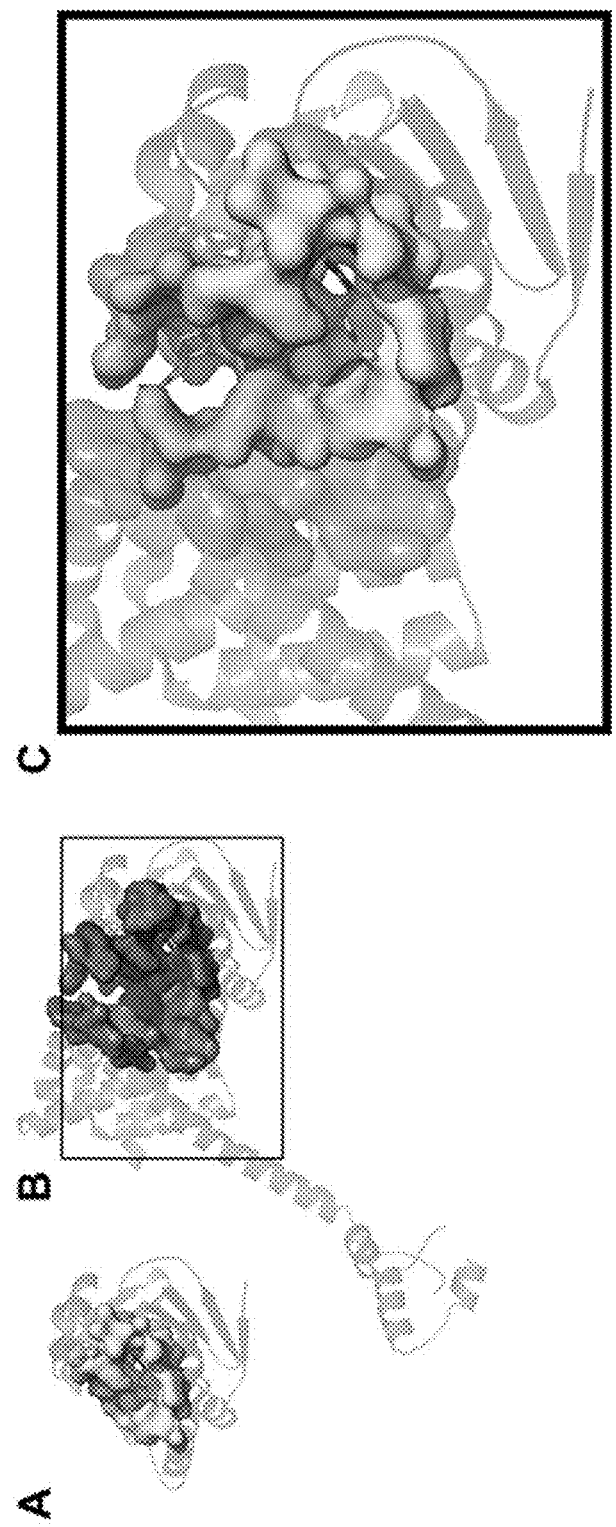
FIG. 20. The HSP90 nucleotide binding site surface (Panel A) shown with bound inhibitor (Wright et al., 2004; herein incorporated by reference in its entirety). When complexed with CDC37, a large cleft is formed at the interface (Panel B). The CDC37 Arg167 residue dissects the cleft into two distinct subpockets (Panel C). The nucleotide binding surface (C) is preserved, but a new sub-pocket is formed. KBU2046 is shown docked into the newly formed site (C). The KBU2046 compound was docked into the newly formed pocket. A suite of docking software, representing different methodologies and approaches was applied. When allowed in the docking procedures, side chains from the HSP90 β-CDC37 complex were allowed to be fully flexible. A consensus pose was reached with root mean square distance (RMSD) less than 1.1 Angstroms over all atoms that exhibits no steric clashing with the complex. This model suggests that the molecule is capable of binding to this secondary site. A dimer of the HSP90β structure in the closed conformation was modeled from *S. cerevisiae* HSP90A (PDB id=2cg9). In construction of the dimer, the HSP90 β-CDC37 interface interactions were maintained. Position and orientation of the extended CDC37 regions were guided by crosslinking data that showed inter-domain cross-links between residues 53-347, 107-347, and 69-286. This resulting structure shows agreement with other reported conformations (Vaughan et al., 2006; herein incorporated by reference in its entirety). In this model, both the ATP and proposed KBU2046 pockets remain intact in the dimerized complex.

These combined experiments indicate that KBU2046 is binding in a cleft that is only present when CDC37 and HSP90β interact. A comprehensive analysis of HSP90β and CDC37 experimental structural information, including X-ray crystallographic data (PDB IDs: luym, 3nmq, 3pry, 2cg9 and lus7) (Roe et al., 2004; Vaughan et al., 2006; Wright et al., 2004; herein incorporated by reference in their entireties) and chemical cross-linker physical mapping analysis (Chavez et al., 2013), indicates that CDC37/HSP90β heterocomplex formation results in the formation of a new pocket that modeling studies indicate allows for KBU2046 binding without any high energy steric interactions, and with a favorable energy score (FIGS. 6B, 6C, 6D; FIG. 20). In this computational arrangement, Arg$^{167}$ from CDC37 protrudes into a large cleft, engages in a hydrogen bond with the carboxyl side chain of Glu$^{33}$ from HSP90β, which promotes formation of a new pocket, into which KBU2046 binds.

KBU2046 does not Inhibit Kinase or Phosphatase Activity.

Three different assays systems were employed to detect inhibition.

Kinase Assay System #1.

The KINOMEscan™ assay (Ambit Biosciences). This assay evaluates 442 kinases, including 400 distinct parental kinases plus mutants known to alter activity or responsiveness. It does so in the context of an assay that measures the ability of putative inhibitors to inhibit binding of bacterial purified kinase to immobilized phospho-acceptor protein substrate. This approach has been successfully used by multiple groups to identify kinase interactions of several small molecule kinase inhibitors (Fabian et al., 2005; Karaman et al., 2008; herein incorporated by reference in their entireties). KBU2046 was tested at 10 μM. This assay was completely negative. There were two initial false positives (for a false positive rate of 0.4%), that were subsequently found to be negative in a dedicated follow up analysis. Specific and important negative findings include MKK4 and p38 MAPK (α, β, and γ isoforms). There was no evidence that KBU2046 inhibits kinase function by competing for phospho-acceptor binding.

Kinase Assay System #2.

The Kinex™ kinase assay system (Kinexus Proteomics Company). This platform uses recombinant human protein kinases expressed in an insect expression system, thus allowing an avenue for post-translational modification. Also, this platform measures inhibition of ATP binding. This platform putatively measured 200 different kinases, and we tested KBU2046 at 1 and 10 μM. This assay was also completely negative. This screen was informative for a number of kinases (e.g., where controls were active and at KBU2046 concentrations that did not interfere with detection). KBU2046 did not inhibit p38 MAPK (all isoforms) nor MKK4. There was no evidence that KBU2046 inhibits kinase function by competing for ATP binding in the active site.

Kinase Assay System #3.

KinaseProfiler™ and PhosphataseProfiler™ assay platforms (Millipore). This platform is radiometric-based (considered gold standard). It measures competition with respect to ATP for kinases and substrate protein for phosphatases. Most proteins were expressed via an insect-based system, and it evaluates a panel of 284 kinases and 20 phosphatases. There were two initial false positives, for a false positive rate of 0.7%, but both failed to be confirmed upon in-depth investigation. Important negative findings include: MKK4, MKK6, p38 MAPK, MAPKAPK2, ERK, MEK1, JNK1, 2 and 3, and numerous other MAPK cascade-associated kinases. There is no evidence that KBU2046 inhibits kinase activity by competing for ATP binding in the active site. No evidence supports inhibition of phosphatase activity.

Construction of Structural Model of HSP90 β, CDC37 and KBU2046 Interaction.

Analysis began with experimentally determined structural information, including the crystal structures of human HSP90 β (pDBs luym, 3nmq and 3pry) and HSP82•CDC37 complex from yeast (pDB Ius7), which were determined by X-ray diffraction-based crystallographic analysis. The HSP90β structure was probed using chemical cross-linking with mass spectrometry, employing chemical cross-linkers of various lengths, as previously described (Chavez et al., 2013; herein incorporated by reference in its entirety). In addition, the HSP90β structure was probed in human cells with the use of chemical cross-linkers called Protein Interaction Reporters (PIRs) (Chavez et al., 2013; herein incorporated by reference in its entirety). Cross-linked peptide samples were analyzed using ReACT (Weisbrod et al., 2013; herein incorporated by reference in its entirety) which allows targeted MS3 to be carried out efficiently on each released peptide that satisfies expected PIR mass relationships (Tang et al., 2005; herein incorporated by reference in its entirety).

It was found that KBU2046 does not bind directly to HSP90β or CDC37 (FIG. 18), but that it does bind to the HSP90β-CDC37 complex (FIG. 6A). Therefore, the complex affords a suitable binding pocket that is not independently present on either protein. In the absence of a complete, X-ray crystallographic structural model of HSP90β, a homology based model using existing structures from the protein data bank (PDB) was relied upon. Structures of the human HSP90β N-terminal ATPase domain (PDB ids=luym, 3nmq) and middle domain (PDB id=3pry) were used. The noncontiguous models cover 65% of the primary sequence, separated by a highly disordered region of 63 residues that terminates the ATP binding domain. No experimental models exist for the C-terminal region. The entirety of the HSP90β structure was then modeled against the HSP82 template from S. cerevisiae (PDB id=2cg9) (Leaver-Fay et al., 2011). A model of the complex of HSP90 β-CDC37 was completed through superposition of the HSP90β model onto the structure of the S. cerevisiae HSP82-CDC37 complex (PDB id=lus7). The sequence identity between HSP90β and HSP82 is 94% at the CDC37 interface (86% for entire protein), thus preserving the integrity of the interactions. A marked feature of the HSP90 structure is the nucleotide binding site. The site, with solvent accessible area of 496.2 Angstroms$^2$ and volume of 301.3 Angstums$^3$ (Binkowski et al., 2003b; herein incorporated by reference in its entirety), has been well characterized and targeted by a variety of compounds for anti-cancer activity. When complexed with CDC37, an expansive surface, with solvent accessible area of 1446.4 Angstroms$^2$ and volume of 2082.6 Angstroms$^3$, is formed at the interface (FIG. 20B). Arg167$_{cdc37}$ is drawn in to the nucleotide binding pocket and forms a hydrogen bond with the carboxyl side chain from Glu33$_{HSP90}$ (Roe et al., 2004; herein incorporated by reference in its entirety). Arg167$_{cdc37}$ does not preclude access to the nucleotide binding site or displace any bound ligands (Roe et al., 2004; herein incorporated by reference in its entirety). It does, however, divide the large cleft into two distinct pockets: a newly formed pocket and the undisturbed, yet smaller, nucleotide binding site. The new pocket has solvent accessible area of 429.2 Angstroms$^2$ and volume of 832.5 Angstroms$^3$ and meets the criteria of a structural feature only present in the HSP90β-CDC37 complexed state.

Example 4

Downstream Regulators

Figure 21A:
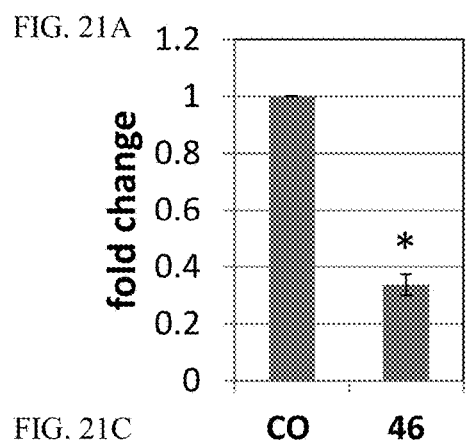
FIGS. 21A-C. KBU2046 disrupts osteonectin expression. PC3 cells were treated+/−with 10 uM KBU2046×3d (A), or were transfected with siRNA to osteonectin (siOST) or non-targeting (siCO) (B), and osteonectin/GAPDH expression measured by qRT/PCR. (C) PC3 cells were transfected with siOST, siCO, treated with +/−KBU2046, and cell invasion measured.
Figure 21B:
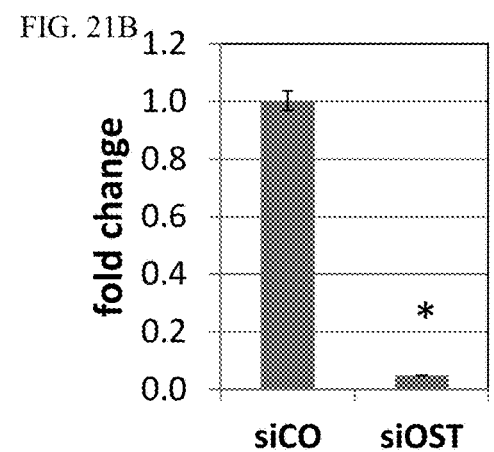
Figure 21C:
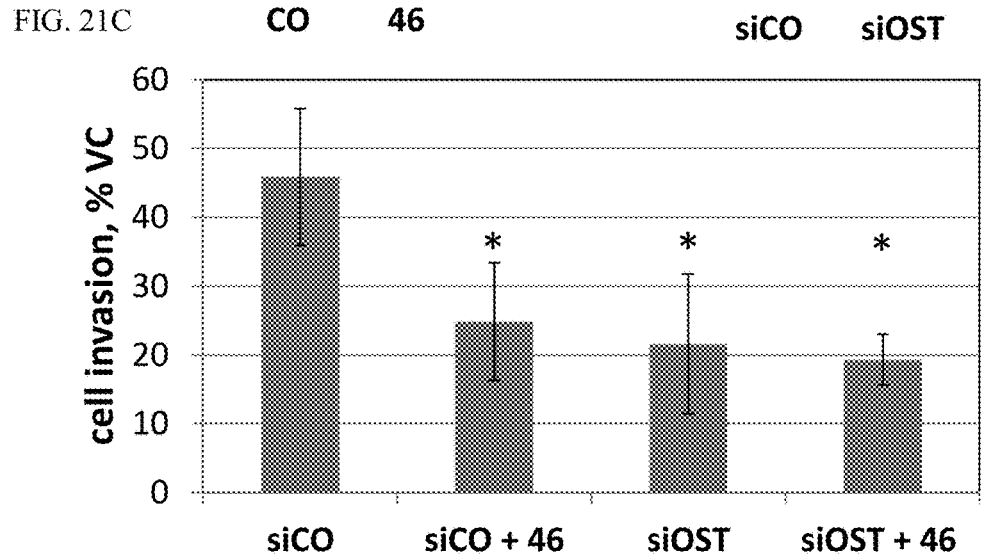

Having identified inhibition of Ser$^{226}$ phosphorylation as the molecular target of KBU2046 for inhibition of cell motilty, experiments were conducted during development of embodiments herein to identify downstream regulators of its action. PC3 cells with KBU2046, and screened for differentially expressed genes using two different SABiosciences (Qiagen) gene array platforms: Human Metastasis Array and Human Extracellular Matrix and Adhesion Molecule Array. KBU2046 was found to significantly suppress osteonectin expression by 2.0 fold. No other significant effects were identified. Separate experiments confirmed differential expression by gene-specific qRT/PCR (FIG. 21A). Osteonectin is an extracellular matrix protein that when overexpressed in PCa has been shown to increase both cell motility and invasion. Clinically, overexpression of osteonectin in primary PCa has been associated with the development of metastasis to bone. Together, these findings indicate that KBU2046 antimetastatic efficacy is mediated, at least in part, by suppression of osteonectin, which was confirmed by demonstrating that siRNA-mediated suppression of osteonectin inhibits human PCa cell invasion and abrogates KBU2046 therapeutic efficacy (FIGS. 21 B and C).

KBU2046 Disrupts HSP90β Chaperone Function

Biochemical methods were employed in experiments conducted during development of embodiments herein to demonstrate that KBU2046 is altering HSP90β/CDC37 heterocomplex formation and resultant chaperone function, that it does so across model systems whose findings are corroboratory, that it does so under rigorously defined in vitro systems utilizing recombinant purified proteins, and that it does so in intact cellular systems. At least the latter involves clinically relevant scenarios related to PCa through a primary effect upon androgen receptor (AR) biology, relating to the fact that AR is a client protein whose function requires HSP90 chaperone activity. Further, findings indicate that KBU2046 binds within a cleft that is formed between the interface of HSP90β and its co-chaperone, CDC37.

CDC37, a co-chaperone, mediates binding of over 350 client proteins to HSP90β, inclusive of over 190 kinases. Its arm-like structure (pdb ID: 2WOG) enables highly dynamic and kinetic conformational changes related to the binding of large numbers of kinases, bringing them in juxtaposition to Ser$^{226}$. It was contemplated that if KBU2046 bound to either CDC37 or HSP90β, the resultant chemical bonds would serve to alter the dynamic function of these two proteins, and their regulation of kinase accessibility to Ser$^{226}$. An exhaustive battery of assays designed to detect KBU2046 binding to HSP90β, CDC37, or HSP90β/CDC37 heterocomplexes was conducted, including: fluorescence-based thermal shift assay, dynamic light scattering, isothermal titration calorimetry, bio-layer interferometry. Assays based on physical measures of binding were negative. However, several biochemical measure did detect binding.

Figure 22A:
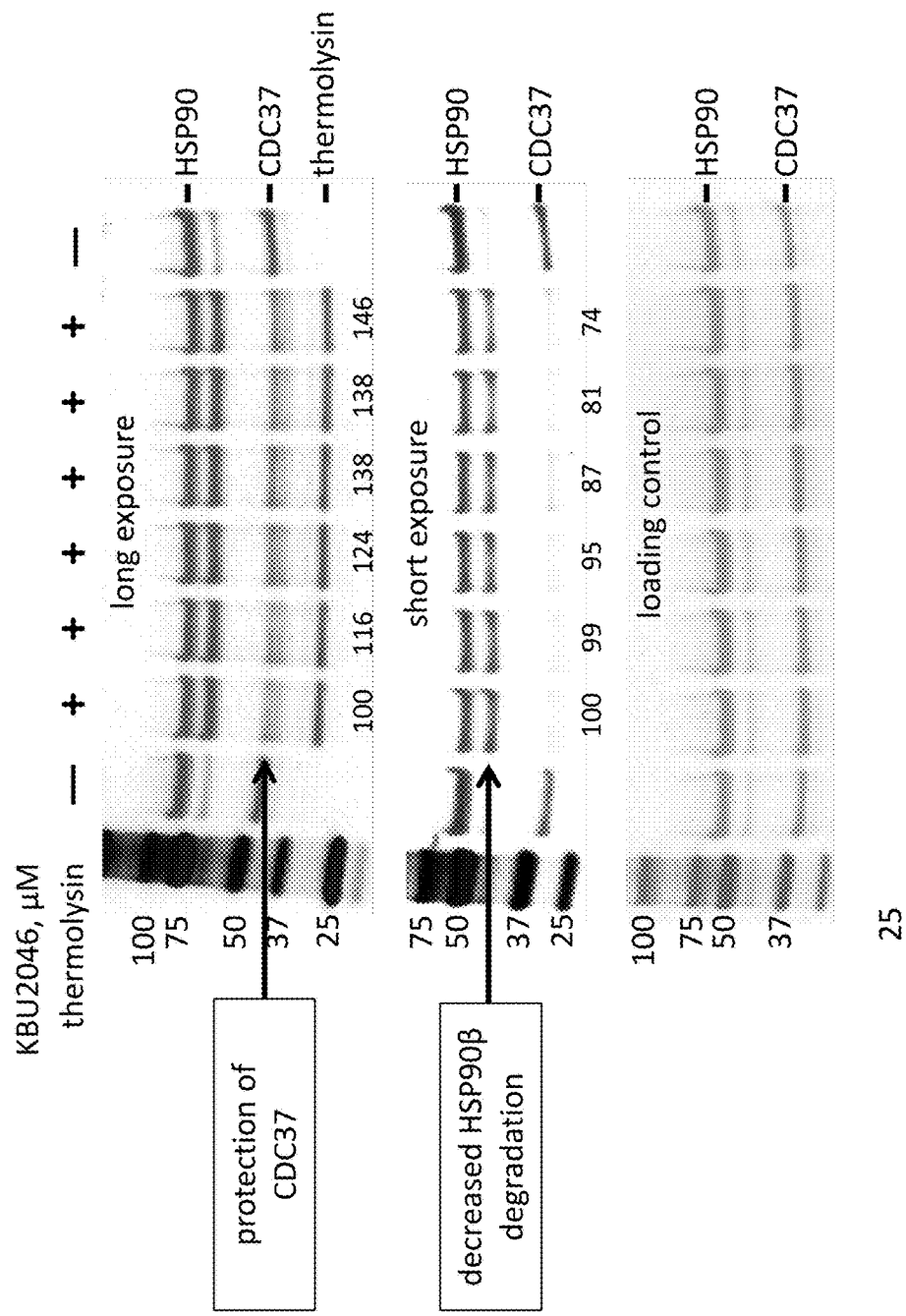
FIGS. 22A-C. KBU2046 binds to HSP90β/CDC37 heterocomplexes and inhibits invasion by inhibiting HSP9013 $Ser^{226}$ phosphorylation. (A) KBU2046 stabilizes HSP9013 and CDC37 proteins in a DARTS assay. Thermolysin was added to an equimolar mixture of recombinant purified HSP90β and CDC37 pre-incubated with KBU2046, followed by silver stain-based detection. The mean value of protein bands, indicated by arrows, is displayed below each lane. P values are ANOVA. (B) KBU2046 stabilizes HSP90β/CDC37/CK. HSP90β, CDC37 and casein kinase (CK), were added in an in vitro kinase assay, followed by Western blot for phospho-serine (P-ser) or with Ab specific for phosphorylated ser226 on HSP90β (P-ser226). The HSP90β primary degradation product exposes serine residues that CK can differentially access. In bottom panel, signal is shown to be dependent upon presence of CK. (C) In-silico model of KBU2046 bound to a CDC37-HSP90β heterocomplex.

The drug affinity responsive target stability (DARTS) assay measures the ability of a bound ligand to protect a target protein from protease digestion, and provides a sensitive measure of ligand-induced changes in protein structure, being particularly sensitive to changes in protein flexibility. Considering that CDC37 and HSP90β bind to form a heterocomplex, it was demonstrated that KBU2046 bound to heterocomplexes. When both proteins were present in a DARTS assay, KBU2046 protected both from protease digestion, significantly increasing CDC37 protein and decreasing HSP90β degradation product in a concentration-dependent fashion (FIG. 22A). When CDC37 or HSP90β were examined individually (e.g., not in a heterocomplex), no protection was observed.

Figure 23A:
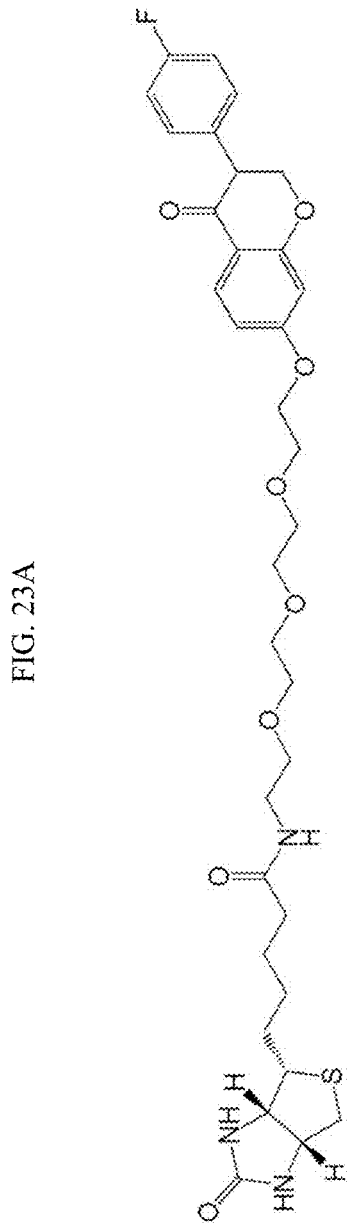
FIGS. 23A-C. KBU2046 biotin linker. (A) Chemical structure of KBU2046 linked to biotin (KBU2046-biotin). (B) KBU2046-biotin is biologically active. PC3-M cells were pre-treated with 10 μM KBU2046 or with KBU2046-biotin for three days, and single cell motility assays conducted. (C) KBU2046-biotin stains cells and is competed off by 10-fold free KBU2046.
Figure 23B:
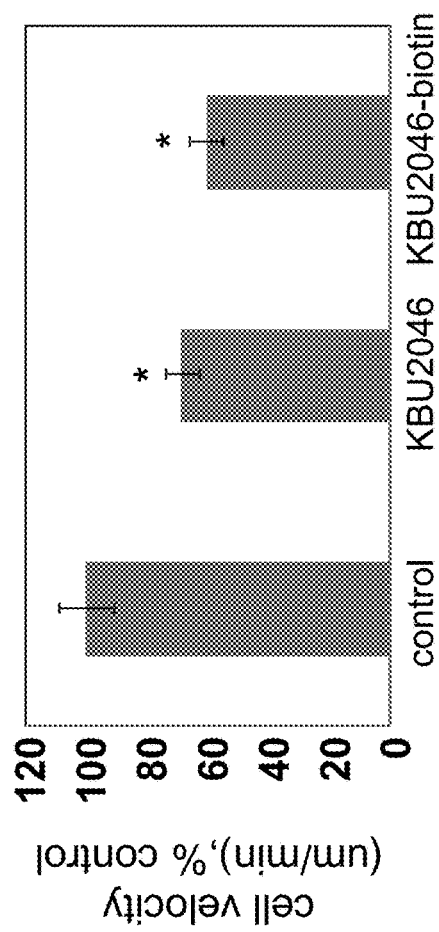
Figure 23C:
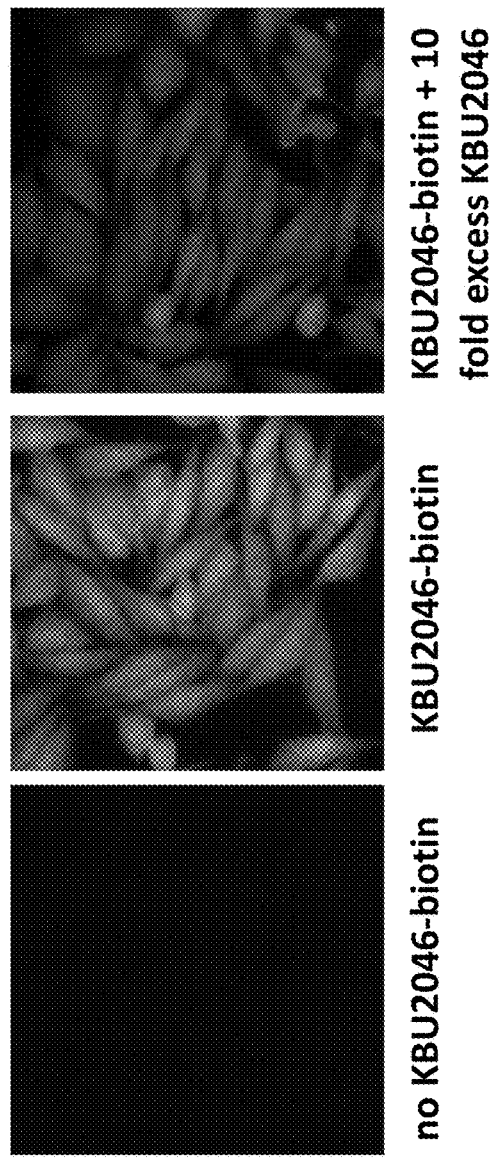

A chemical linker to was attached KBU2046 (FIG. 23), that retained biological activity and that bound to intact cells (e.g., with physiologic CDC37/HSP90β heterocomplexes), and experiments indicated that it did not bind a 9,000 human protein array (ProtoArray®; Invitrogen), inclusive of HSP90β and CDC37.

Figure 22B:
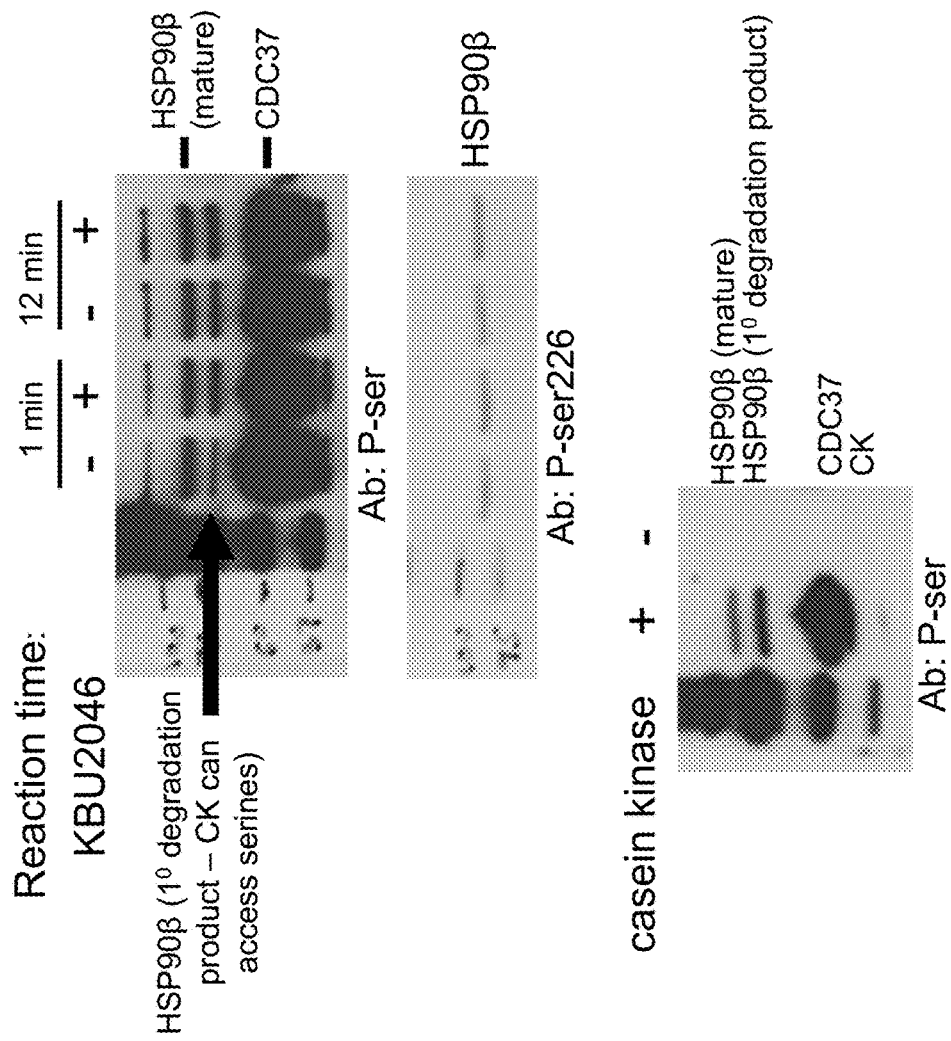

Experiments conducted during development of embodiments herein demonstrated that KBU2046 regulates heterocomplex function. In an in vitro system of recombinant HSP90β, CDC37 and casein kinase (CK) proteins (engineered by us), KBU2046 increased CK-mediated phosphorylation of HSP90β (FIG. 22B). CDC37 mediates binding of client proteins to HSP90β, that CK is a client protein kinase. KBU2046 does not modulate CK kinase activity. CK did not increase phosphorylation of Ser226. These findings all indicate that inside the cell KBU2046 stabilizes CDC37/HSP90β heterocomplex formation, this increases binding of certain client proteins, thereby inhibiting that of other client proteins which phosphorylate Ser226.

Figure 22C:
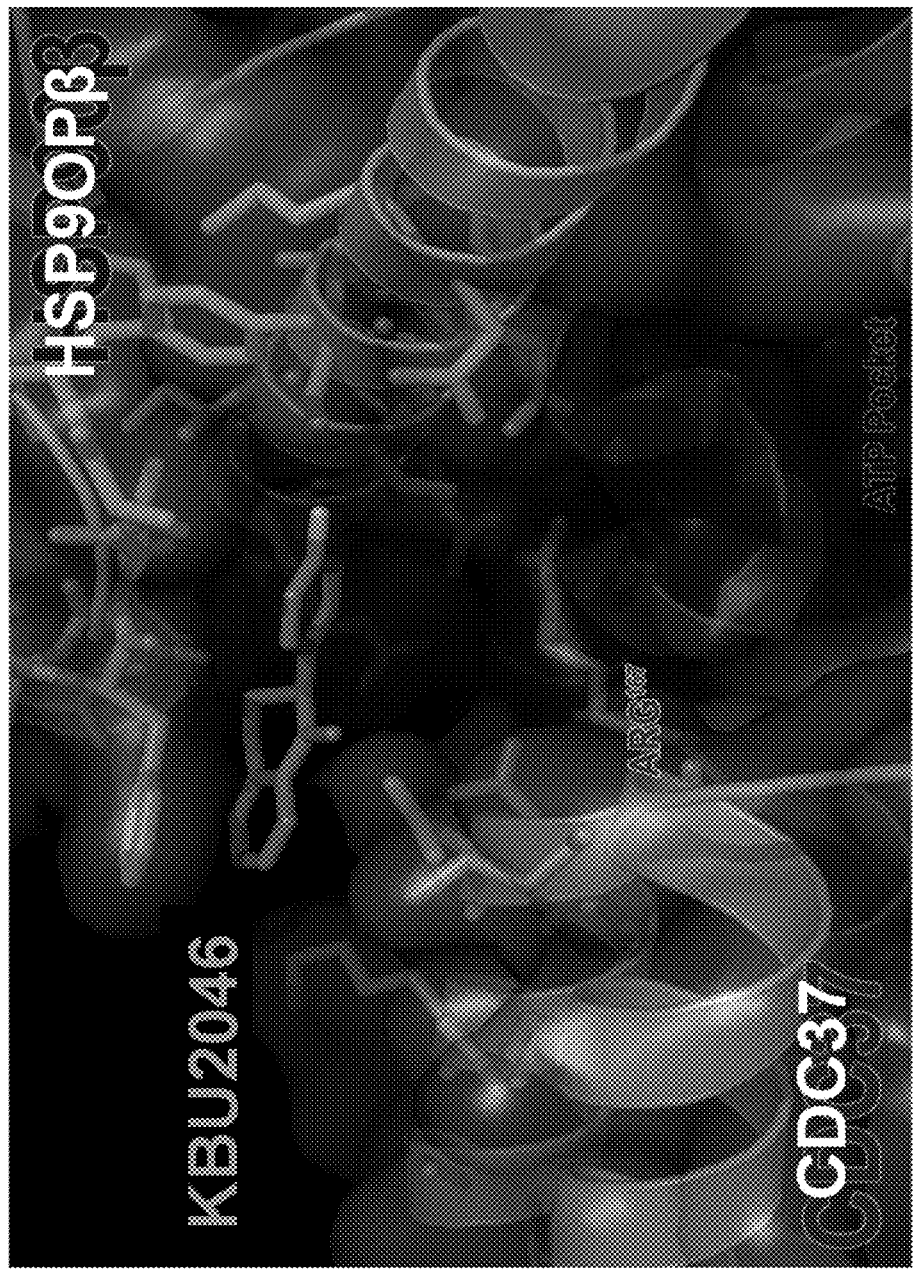

HSP90β and CDC37 structural information derived by a crosslinking approach wherein chemical cross-linking probes (of various lengths and ligand binding capacities) are coupled to MS3-based analysis, X-ray crystallographic structural information (Protein Database ID's: luym, 3nmq, 3pry and lus7), and ligand binding information informed by the DARTS experiments above. The structural information was integrated, through the APPLIED Pipeline platform at the Argonne National Laboratory Leadership Computing Facility. It integrates protein surface analysis, robust homology modeling, massively parallel docking simulations using mixed strategies, and advanced physics-based rescoring methodologies. The resultant informed model indicated that HSP90β and CDC37 binding forms a new pocket into which KBU2046 binds without high-energy steric interactions and with a favorable energy score (FIG. 22C). Arg167 from CDC37 protrudes into a large cleft, hydrogen bonds with Glu33 of HSP90β, and forms a new pocket. This model indicates that KBU2046 promotes protein-protein interaction. This model agrees with experimental DARTS data demonstrating that KBU2046 stabilizes HSP90β/CDC37 heterocomplexes (FIG. 22A), but does not stabilize HSP90β or CDC37 individually.

Having demonstrated that KBU2046 impacts chaperone function in cell free systems, experiments were conducted during development of embodiments herein using molecular and cellular-based assays to demonstrate the effect in cells. The chaperone action of HSP90 maintains AR in its active conformation, and inhibitors of HSP90 function block ligand-independent AR signaling. Therefore, if KBU2046 disrupts HSP90 function, as experiments conducted indicate, KBU2046 would disrupt AR-associated chaperone function, inhibit AR-dependent transcriptional activity and inhibit AR-dependent cell growth and enhance the therapeutic efficacy of AR-directed therapy; the experiments conducted during development of embodiments herein demonstrate as much.

Classic HSP90-targeting agents directly bind HSP90, interrupt its chaperone cycle, and thereby exert relatively profound changes on a central cellular process, which in turn induces direct cytotoxicity. At the systemic level, such profound pharmacologic effects disrupt normal cellular function, induce systemic toxicity, and thereby limit ultimate therapeutic efficacy. This is similar to the situation with cytotoxic chemotherapy. In contrast, KBU2046 represents a therapeutic manipulation that exerts a more selective effect upon HSP90 function and is not systemically toxic. However, one consequence of KBU2046's mechanistic effects is that its effects upon rapid-readout in vitro assay systems are less robust than cytotoxic chemotherapy or classic HSP90 inhibitors. Based on this, the experiments described herein involving KBU2046-mediated disruption of AR signaling were expected to procude small effects with short term in vitro assay, as was observed. However, corroboratory effects were demonstrated across multiple assays, involving measures of molecular interaction, cell signaling and cell growth. Further, even in the context of short term in vitro assay systems, enhanced efficacy with increased treatment time was observed.

Figure 24A:
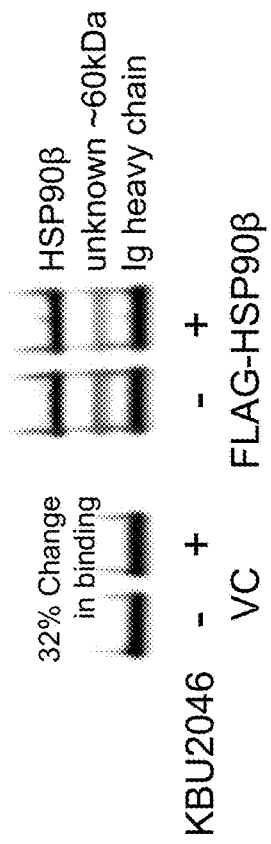
FIGS. 24A-D. KBU2046 inhibits the AR-chaperone pathway, and androgen-driven signaling and growth. (A) KBU2046 decreases binding of a ~62 kDa protein to HSP90β. PC3-M cells were transfected with FLAG- HSP90β, treated for 24 hr with 10 uM KBU2046, FLAG-HSP90β IP'ed, and protein detected by silver stain. (B) KBU2046 decreases binding of HOP to HSP90β. The same conditions (A), followed by Western blot for HOP. (C) KBU2046 inhibits AR transcriptional activity. LNCaP cells, in charcoal stripped serum (CSS) treated with 10 uM KBU2046 (46), 10 uM bicalutamide (B) or 1.0 nM R1881, and 24 hr later PSA measured by qRT/PCR (normalized to GAPDH and to untreated controls). (D) KBU2046 inhibits androgen-driven growth and increases bicalutamide efficacy. LNCaP and VCaP cells were pre-incubated×3 days in CSS, then treated as indicated for either 3 or 6 days, and cell number measured.
Figure 24B:
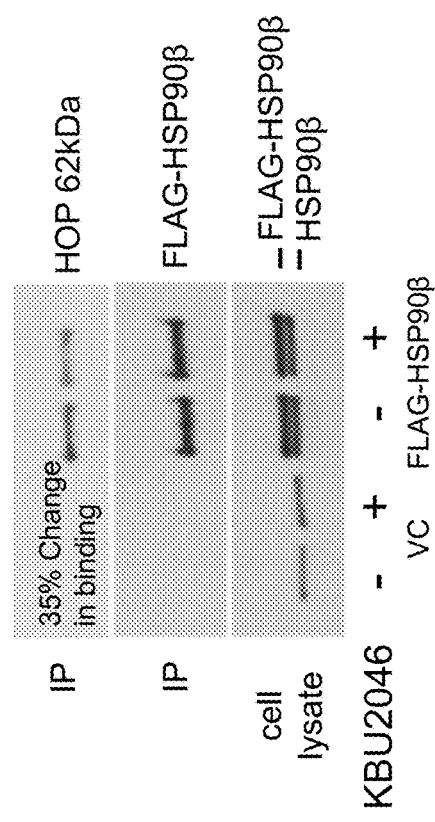
Figure 24C:
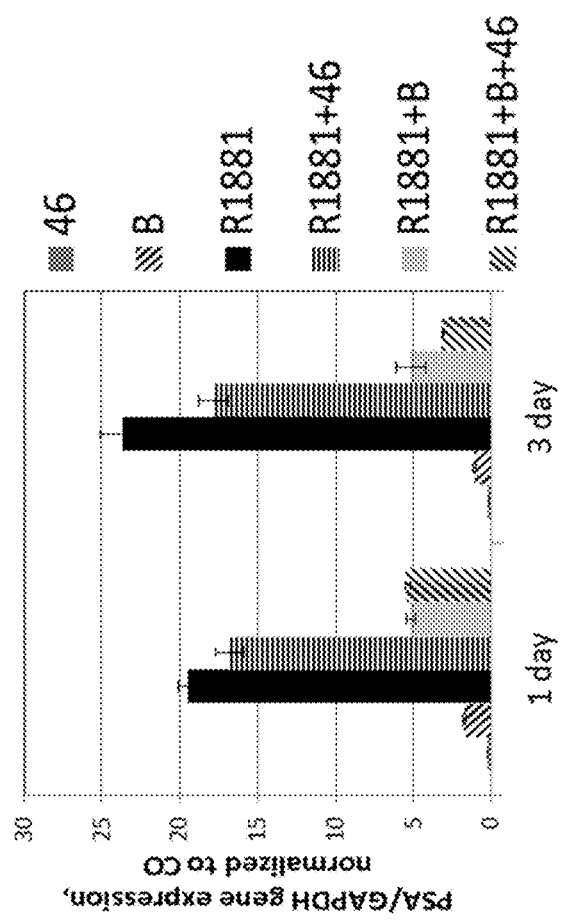
Figure 24D:
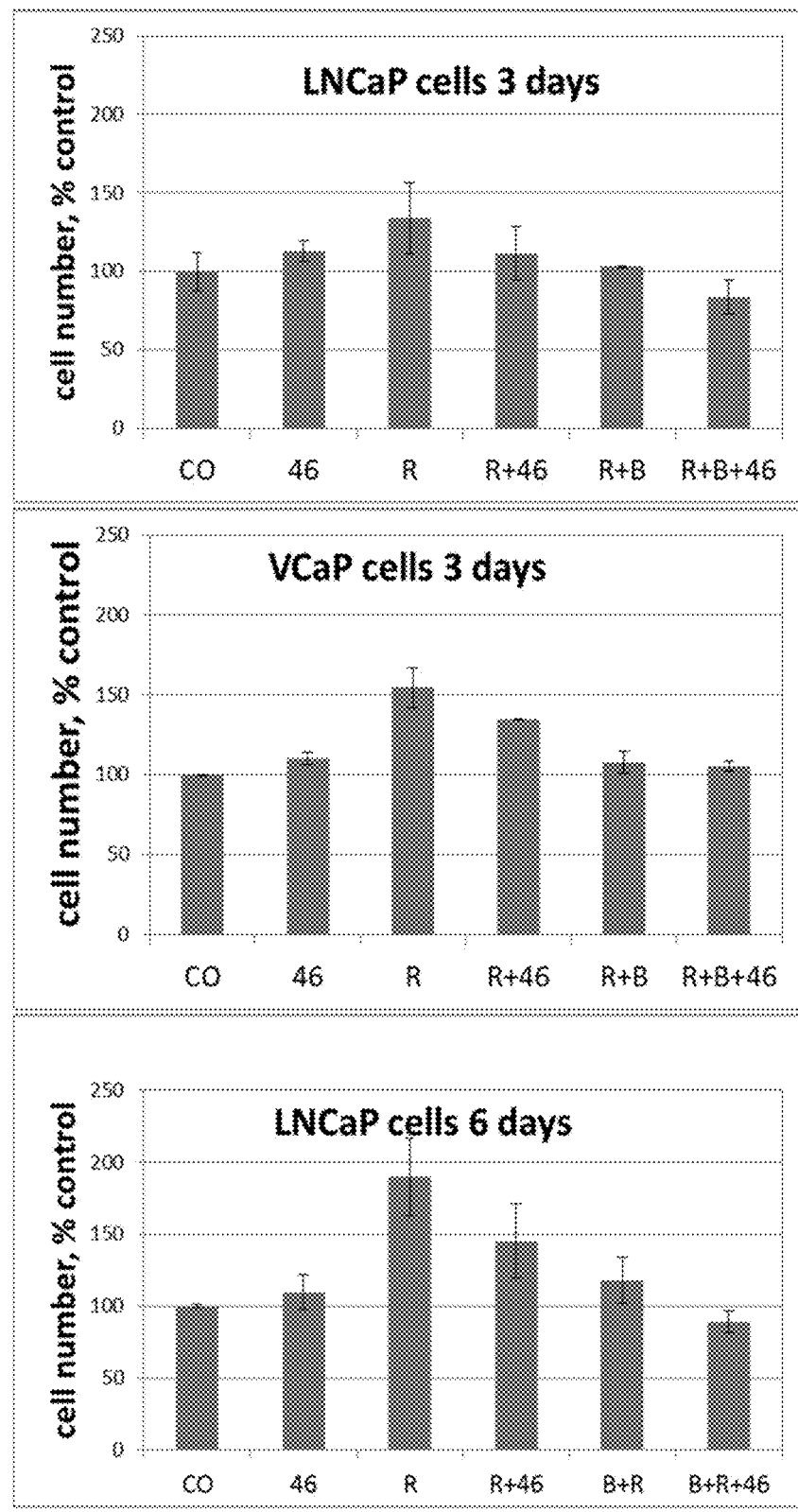

Specifically, performed FLAG IP followed by silver stain was performed using cells transfected with FLAG-HSP90β and treated with +/−KBU2046. KBU2046 disrupted binding of a ~60 kDa protein (FIG. 24A). MS-based proteomic analysis identified it a HOP. This is a very important finding. HOP is a member of the chaperone complex that brings AR to HSP90. Findings were confirmed by HOP-specific Western blot FIG. 24B). Thus, KBU2046 disrupts a molecular interaction known to be necessary for chaperone-mediated maintenance of active AR. KBU2046 disruption of AR-related chaperone activity decreases AR-responsive gene activation (FIG. 24C). AR positive LNCaP cells were grown under charcoal stripped serum (CSS) hormone-free conditions, treated with KBU2046, R1881 (e.g., androgen) and/or bicalutamide for 1 or 3 days and the expression of AR-responsive prostate specific antigen (PSA) measured by qRT/PCR. KBU2046 had no effect by itself, but it inhibited R1881-mediated PSA expression, with effects greater at 3 days. Though a weak agonist by itself in LNCaP cells (due to an AR T868A mutation), bicalutamide functionally inhibits the strong agonist action of R1881, and thus decreases R1881-mediated increases in PSA. Importantly, 3 days treatment with KBU2046 increases the therapeutic efficacy of bicalutamide. KBU2046 acts to inhibit androgen-driven cell growth, that it enhances bicalutamide efficacy, and that effects are amplified as treatment time increases from 3 to 6 days (FIG. 24D). Assays were performed this in both LNCaP (mutant AR) and VCaP cells.

REFERENCES

The following references, as well as those in the text above, as herein incorporated by reference in their entireties.

Andersen, O. M., and Markham, K R, eds. (2006). Flavanoids: Chemistry, Biochemistry and Applications, (Boca Raton: CRC Press).

Avram, M. J., Spyker, D. A, Henthorn, T. K, and Cassella, J. V. (2009). The pharmacokinetics and bioavailability of prochlorperazine delivered as a thermally generated aerosol in a single breath to volunteers. Clinical pharmacology and therapeutics 85, 71-77.

Barrett, P. H., Bell, B. M., Cobelli, C., Golde, H., Schumitzky, A, Vicini, P., and Foster, D. M. (1998). SAAM II: Simulation, Analysis, and Modeling Software for tracer and pharmacokinetic studies. Metabolism: clinical and experimental 47, 484-492.

Bergan, R, Hakim, F., Schwartz, G. N., Kyle, E., Cepada, R, Szabo, J. M., Fowler, D., Gress, R, and Neckers, L. (1996). Electroporation of synthetic oligodeoxynucleotides: a novel technique for ex vivo bone marrow purging. Blood 88, 731-741.

Binkowski, T. A, Adamian, L., and Liang, J. (2003). Inferring functional relationships of proteins from local sequence and spatial surface patterns. Journal of molecular biology 332, 505526.

Binkowski, T. A, and Joachimiak, A. (2008). Protein functional surfaces: global shape matching and local spatial alignments of ligand binding sites. BMC structural biology 8, 45.

Binkowski, T. A, Joachimiak, A, and Liang, J. (2005). Protein surface analysis for function annotation in high-throughput structural genomics pipeline. Protein science: a publication of the Protein Society 14, 2972-2981.

Breen, M. J., Moran, D. M., Liu, W., Huang, X., Vary, C. P., and Bergan, R C. (2013). Endoglin-mediated suppression of prostate cancer invasion is regulated by activin and bone morphogenetic protein type II receptors. PloS one 8, e72407.

Catherino, W. H., and Jordan, V. C. (1995). Increasing the number of tandem estrogen response elements increases the estrogenic activity of a tamoxifen analogue. Cancer Lett 92, 39-47.

Chavez, J. D., Weisbrod, C. R, Zheng, C., Eng, J. K, and Bruce, J. E. (2013). Protein interactions, post-translational modifications and topologies in human cells. Molecular & cellular proteomics: MCP 12, 1451-1467.

Cobelli, C., and Foster, D. M. (1998). Compartmental models: theory and practice using the SAAM II software system. Advances in experimental medicine and biology 445, 79-101.

Coussens, L. M., Fingleton, B., and Matrisian, L. M. (2002). Matrix metalloproteinase inhibitors and cancer: trials and tribulations. Science 295, 2387-2392.

Craft, C. S., Romero, D., Vary, C. P., and Bergan, R. C. (2007). Endoglin inhibits prostate cancer motility via activation of the ALK2-Smad1 pathway. Oncogene 26, 7240-7250.

Deng, Y, and Roux, B. (2008). Computation of binding free energy with molecular dynamics and grand canonical Monte Carlo simulations. The Journal of chemical physics 128, 115103.

Ding, Y., Xu, L., Jovanovic, B. D., Helenowski, 1. B., Kelly, D. L., Catalona, W. J., Yang, X. J., Pins, M., and Bergan, R C. (2007). The methodology used to measure differential gene expression affects the outcome. J Biomol Tech 18, 321-330.

du Manoir, J. M., Francia, G., Man, S., Mossoba, M., Medin, J. A, Viloria-Petit, A, Hicklin, D. J., Emmenegger, D., and Kerbel, R. S. (2006). Strategies for delaying or treating in vivo acquired resistance to trastuzumab in human breast cancer xenografts. Clinical cancer research: an official journal of the American Association for Cancer Research 12, 904-916.

Foster, D. M. (1998). Developing and testing integrated multicompartrnent models to describe a single-input multiple-output study using the SAAM II software system. Advances in experimental medicine and biology 445, 59-78.

Friedl, P., and Wolf, K. (2003). Tumour-cell invasion and migration: diversity and escape mechanisms. Nature reviews Cancer 3, 362-374.

Graves, A. P., Shivakumar, D. M., Boyce, S. E., Jacobson, M. P., Case, D. A., and Shoichet, B. K. (2008). Rescoring docking hit lists for model cavity sites: predictions and experimental testing. Journal of molecular biology 377, 914-934.

Guest, I., and Uetrecht, J. (1999). Drugs that induce neutropenia/agranulocytosis may target specific components of the stromal cell extracellular matrix. Medical hypotheses 53, 145-151.

Huang, x., Chen, S., Xu, L., Liu, Y Q., Deb, D. K., Platanias, L. C., and Bergan, R C. (2005). Genistein inhibits p38 MAP kinase activation, MMP-2, and cell invasion in human prostate epithelial cells. Cancer research 65, 3470-3478.

Jiang, W., Hodoscek, M., and Roux, R (2009). Computation of Absolute Hydration and Binding Free Energy with Free Energy Pel lurbation Distributed Replica-Exchange Molecular Dynamics (FEPIREMD). Journal of chemical theory and computation 5, 2583-2588.

Jiang, W., and Roux, B. (2010). Free Energy Perturbation Hamiltonian Replica-Exchange Molecular Dynamics (FEPIH-REMD) for Absolute Ligand Binding Free Energy Calculations. Journal of chemical theory and computation 6, 2559-2565.

Kataria, B. K., Ved, S. A., Nicodemus, H. F., Hoy, G. R, Lea, D., Dubois, M. Y., Mandema, 1. W., and Shafer, S. L. (1994). The phannacokinetics of propofol in children using three different data analysis approaches. Anesthesiology 80, 104-122.

Knodell, R. G., Ishak, K. G., Black, W. C., Chen, T. S., Craig, R, Kaplowitz, N., Kiernan, T. W., and Wollman, J. (1981). Formulation and application of a numerical scoring system for assessing histological activity in asymptomatic chronic active hepatitis. Hepatology 1, 431-435.

Krishna, S. N., and Bergan, R. C. (2014). Therapeutic modulation of prostate cancer metastasis. Future medicinal chemistry 6, 223-239.

Krishna, S. N., Luan, C. R., Mishra, R K., Xu, L., Scheidt, K. A., Anderson, W. F., and Bergan, R. C. (2013). A fluorescence-based thermal shift assay identifies inhibitors of mitogen activated protein kinase kinase 4. PloS one 8, e81504.

Lakshman, M., Xu, L., Ananthanarayanan, Y, Cooper, J., Takimoto, C. R., Helenowski, I., Pelling, J. C., and Bergan, R C. (2008). Dietary genistein inhibits metastasis of human prostate cancer in mice. Cancer research 68, 2024-2032.

Lang, P. T., Brozell, S. R, Mukherjee, S., Pettersen, E. F., Meng, E. C., Thomas, V., Rizzo, R. C., Case, D. A., James, T. L., and Kuntz, I. D. (2009). DOCK 6: combining techniques to model RNA-small molecule complexes. RNA 15, 1219-1230.

Leaver-Fay, A., Tyka, M., Lewis, S. M., Lange, O. F., Thompson, J., Jacak, R, Kaufman, K., Renfrew, P. D., Smith, C. A., Sheffler, W., et al. (2011). ROSETTA3: an object-oriented software suite for the simulation and design of macromolecules. Methods in enzymology 487 545-574.

Lipinski, C. A., Lombardo, F., Dominy, B. W., and Feeney, P. J. (2001). Experimental and computational approaches to estimate solubility and permeability in drug discovery and development settings. Adv Drug Deliv Rev 46, 3-26.

Liu, Y, Jovanovic, R, Pins, M., Lee, C., and Bergan, R C. (2002). Over expression of endoglin in human prostate cancer suppresses cell detachment, migration and invasion. Oncogene 21, 8272-8281.

Lomenick, B., Hao, R, Jonai, N., Chin, R. M., Aghajan, M., Warburton, S., Wang, J., Wu, R. P., Gomez, F., Loo, 1. A, et al. (2009). Target identification using drug af:fmity responsive target stability (DARTS). Proceedings of the Nationa! Academy of Sciences of the United States of America 106, 21984-21989.

Lundgren, D. H., Martinez, H., Wright, M. E., and Han, D. K. (2009). Protein identification using Sorcerer 2 and SEQUEST. Curr Protoc Bioinformatics Chapter 13, Unit 13 13.

Manas, E. S., Xu, Z. B., Unwalla, R. J., and Somers, W. S. (2004). Understanding the selectivity of genistein for human estrogen receptor-beta using X-ray crystallography and computational methods. Structure 12, 2197-2207.

Messina, M., McCaskill-Stevens, W., and Lampe, J. W. (2006). Addressing the soy and breast cancer relationship: review, commentary, and workshop proceedings. J Natl Cancer Inst 98, 1275-1284.

Minn, A 1., and Massague, J. (2008). Invasion and Metastasis. In CANCER: Principals and Practice of Oncology, V. T. DeVita, T. S. Lawrence, and S. A Rosenberg, eds. (New York: Lippincott Wiliams & Wilkins), pp. 135-146.

Morris, G. M., Huey, R, Lindstrom, W., Sanner, M. F., Belew, R K., Goodsell, D. S., and Olson, A J. (2009). AutoDock4 and AutoDockTools4: Automated docking with selective receptor flexibility. Journal of computational chemistry 30, 2785-2791.

Neckers, L., and Workman, P. (2012). Hsp90 molecular chaperone inhibitors: are we there yet? Clinical cancer research: an official journal of the American Association for Cancer Research 18, 64-76.

Pavese, J., Ogden, I. M., and Bergan, R C. (2013). An orthotopic murine model of humanprostate cancer metastasis. Journal of visualized experiments: JoVE, e50873.

Pavese, 1. M., Farmer, R L., and Bergan, R C. (2010). Inhibition of cancer cell invasion and metastasis by genistein. Cancer Metastasis Rev 29, 465-482.

Polier, S., Samant, R. S., Clarke, P. A., Workman, P., Prodromou, C., and Pearl, L. H. (2013). ATP-competitive inhibitors block protein kinase recruitment to the Hsp90-Cdc37 system. Nature chemical biology 9, 307-312.

Roe, S. M., Ali, M. M., Meyer, P., Vaughan, C. K., Panaretou, B., Piper, P. W., Prodromou, C., and Pearl, L. H. (2004). The Mechanism of Hsp90 regulation by the protein kinase-specific cochaperone p50(cdc37). Cell 116, 87-98.

Shoemaker, R. H. (2006). The NCI60 human tumour cell line anticancer drug screen. Nature reviews Cancer 6, 813-823.

Steeg, P. S. (2006). Tumor metastasis: mechanistic insights and clinical challenges. Nature medicine 12, 895-904.

Taipale, M., Krykbaeva, I., Koeva, M., Kayatekin, C., Westover, K. D., Karras, G. I., and Lindquist, S. (2012).

Quantitative analysis of HSP90-client interactions reveals principles of substrate recognition. Cell 150, 987-1001.

Talmadge, J. E., and Fidler, I. J. (2010). AACR centennial series: the biology of cancer metastasis: historical perspective. Cancer research 70, 5649-5669.

Tang, x., Munske, G. R., Siems, W. F., and Bruce, 1. E. (2005). Mass spectrometry identifiable cross-linking strategy for studying protein-protein interactions. Analytical chemistry 77, 311318.

Vaughan, C. K., Gohlke, U., Sobott, F., Good, V M., Ali, M. M., Prodromou, C., Robinson, C. V, Saibil, H. R., and Pearl, L. H. (2006). Structure of an Hsp90-Cdc37-Cdk4 complex. Molecular cell 23, 697-707.

Wang, J., Deng, Y, and Roux, B. (2006). Absolute binding free energy calculations using molecular dynamics simulations with restraining potentials. Biophysical journal 91, 2798-2814.

Weisbrod, C. R., Chavez, J. D., Eng, J. K., Yang, L., Zheng, C., and Bruce, J. E. (2013). In Vivo Protein Interaction Network Identified with a Novel Real-Time Cross-Linked Peptide Identification Strategy. Journal of proteome research.

Wells, A., Grahovac, J., Wheeler, S., Ma, B., and Lauffenburger, D. (2013). Targeting tumor cell motility as a strategy against invasion and metastasis. Trends in pharmacological sciences 34, 283-289.

Whitesell, L., Santagata, S., and Lin, N. U. (2012). Inhibiting HSP90 to treat cancer: a strategy in evolution. Current molecular medicine 12, 1108-1124.

Wright, L., Barril, x., Dymock, B., Sheridan, L., Surgenor, A, Beswick, M., Drysdale, M., Collier, A, Massey, A., Davies, N., et al. (2004). Structure-activity relationships in purine-based inhibitor binding to HSP90 isoforms. Chemistry & biology II, 775-785.

Xu, L., and Bergan, R. C. (2006). Genistein inhibits matrix metalloproteinase type 2 activation and prostate cancer cell invasion by blocking the transforming growth factor beta-mediated activation of mitogen-activated protein kinase-activated protein kinase 2-27-kDa heat shock protein pathway. Mol Pharmacol 70, 869-877.

Xu, L., Ding, Y., Catalona, W. J., Yang, X., Anderson, W. F., Jovanovic, B. D., Wellman, K., KµMer, J., Huang, X., Scheidt, K. A, et al. (2009). MEK4 Function, Genistein Treatment, and Invasion of Human Prostate Cancer Cells. Journal of the National Cancer Institute 101, 11411155.

Zubriene, A, Gutkowska, M., Matuliene, 1., Chaleckis, R., Michailoviene, V, Voroncova, A., Venclovas, C., Zylicz, A., Zylicz, M., and Matulis, D. (2010). Thermodynamics of radicicol binding to human Hsp90 alpha and beta isoforms. Biophysical chemistry 152, 153-163.

The invention claimed is:

1. A method for treating a subject suffering from cancer comprising administering the subject a compound having formula of:

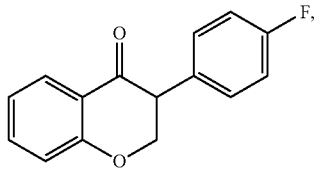 [SMILES: O=C1c2ccccc2OCC1c1ccc(F)cc1]

wherein the cancer is not prostate cancer or breast cancer.

2. The method of claim 1, wherein the compound is administered prior to surgical removal of a tumor.

3. The method of claim 1, wherein the compound is administered after surgical removal of a tumor.

4. The method of claim 1, wherein the compound is co-administered with a second cancer therapeutic agent.

5. The method of claim 4, wherein the second cancer therapeutic agent is a chemotherapeutic agent.

6. The method of claim 4, wherein the second cancer therapeutic agent is an anti-motility agent.

* * * * *

```
                         SEQUENCE LISTING

<160> NUMBER OF SEQ ID NOS: 19

<210> SEQ ID NO 1
<211> LENGTH: 22
<212> TYPE: PRT
<213> ORGANISM: Homo sapiens

<400> SEQUENCE: 1

Leu Leu Lys Pro Gly Glu Glu Pro Ser Glu Tyr Thr Asp Glu Glu Asp
1               5                   10                  15

Thr Lys Asp His Asn Lys
            20

<210> SEQ ID NO 2
<211> LENGTH: 25
<212> TYPE: PRT
<213> ORGANISM: Homo sapiens

<400> SEQUENCE: 2

Asn Gly Ser Leu Asp Ser Pro Gly Lys Gln Asp Thr Glu Glu Asp Glu
1               5                   10                  15

Glu Glu Asp Glu Lys Asp Lys Gly Lys
            20                  25

<210> SEQ ID NO 3
<211> LENGTH: 14
<212> TYPE: PRT
<213> ORGANISM: Homo sapiens

<400> SEQUENCE: 3

Ser Arg Ser Asp Ile Asp Val Asn Ala Ala Ala Gly Ala Lys
1               5                   10

<210> SEQ ID NO 4
<211> LENGTH: 12
<212> TYPE: PRT
<213> ORGANISM: Homo sapiens
```

```
<400> SEQUENCE: 4

Cys Asn Thr Asp Asp Thr Ile Gly Asp Leu Lys Lys
1               5                  10

<210> SEQ ID NO 5
<211> LENGTH: 27
<212> TYPE: PRT
<213> ORGANISM: Homo sapiens

<400> SEQUENCE: 5

Gly His His Val Thr Asp Ser Glu Asn Asp Glu Pro Leu Asn Leu Asn
1               5                  10                  15

Ala Ser Asp Ser Glu Ser Glu Glu Leu His Arg
            20                  25

<210> SEQ ID NO 6
<211> LENGTH: 24
<212> TYPE: PRT
<213> ORGANISM: Homo sapiens

<400> SEQUENCE: 6

Val Gly Pro Gly Asn His Gly Thr Glu Gly Ser Gly Gly Glu Arg His
1               5                  10                  15

Ser Asp Thr Asp Ser Asp Arg Arg
            20

<210> SEQ ID NO 7
<211> LENGTH: 24
<212> TYPE: PRT
<213> ORGANISM: Homo sapiens

<400> SEQUENCE: 7

Val Gly Pro Gly Asn His Gly Thr Glu Gly Ser Gly Gly Glu Arg His
1               5                  10                  15

Ser Asp Thr Asp Ser Asp Arg Arg
            20

<210> SEQ ID NO 8
<211> LENGTH: 17
<212> TYPE: PRT
<213> ORGANISM: Homo sapiens

<400> SEQUENCE: 8

Ser Glu Asp Gly Tyr His Ser Asp Gly Asp Tyr Gly Glu His Asp Tyr
1               5                  10                  15

Arg

<210> SEQ ID NO 9
<211> LENGTH: 10
<212> TYPE: PRT
<213> ORGANISM: Homo sapiens

<400> SEQUENCE: 9

Ser Glu Ser Ser Asp Phe Val Val Pro Lys
1               5                  10

<210> SEQ ID NO 10
<211> LENGTH: 24
<212> TYPE: PRT
<213> ORGANISM: Homo sapiens

<400> SEQUENCE: 10
```

```
Asp Arg Pro His Ala Ser Gly Thr Asp Gly Asp Glu Ser Glu Glu Asp
1               5                   10                  15

Pro Pro Glu His Lys Pro Ser Lys
            20
```

<210> SEQ ID NO 11
<211> LENGTH: 17
<212> TYPE: PRT
<213> ORGANISM: Homo sapiens

<400> SEQUENCE: 11

```
Glu Arg Asp His Ser Pro Thr Pro Ser Val Phe Asn Ser Asp Glu Glu
1               5                   10                  15

Arg
```

<210> SEQ ID NO 12
<211> LENGTH: 12
<212> TYPE: PRT
<213> ORGANISM: Homo sapiens

<400> SEQUENCE: 12

```
His Val Leu Ser Asp Leu Glu Asp Asp Glu Val Arg
1               5                   10
```

<210> SEQ ID NO 13
<211> LENGTH: 10
<212> TYPE: PRT
<213> ORGANISM: Homo sapiens

<400> SEQUENCE: 13

```
Asp Gln Lys Leu Ser Glu Leu Asp Asp Arg
1               5                   10
```

<210> SEQ ID NO 14
<211> LENGTH: 14
<212> TYPE: PRT
<213> ORGANISM: Homo sapiens

<400> SEQUENCE: 14

```
Asp Leu Leu Ser Asp Leu Gln Asp Ile Ser Asp Ser Glu Arg
1               5                   10
```

<210> SEQ ID NO 15
<211> LENGTH: 17
<212> TYPE: PRT
<213> ORGANISM: Homo sapiens

<400> SEQUENCE: 15

```
Met Gln Asn Thr Asp Asp Glu Glu Arg Pro Gln Leu Ser Asp Asp Glu
1               5                   10                  15

Arg
```

<210> SEQ ID NO 16
<211> LENGTH: 24
<212> TYPE: PRT
<213> ORGANISM: Homo sapiens

<400> SEQUENCE: 16

```
Asp Arg Pro His Ala Ser Gly Thr Asp Gly Asp Glu Ser Glu Glu Asp
1               5                   10                  15

Pro Pro Glu His Lys Pro Ser Lys
            20
```

```
<210> SEQ ID NO 17
<211> LENGTH: 22
<212> TYPE: PRT
<213> ORGANISM: Homo sapiens

<400> SEQUENCE: 17

Thr Lys Phe Ala Ser Asp Asp Glu His Asp Glu His Asp Glu Asn Gly
1               5                   10                  15

Ala Thr Gly Pro Val Lys
            20

<210> SEQ ID NO 18
<211> LENGTH: 26
<212> TYPE: PRT
<213> ORGANISM: Homo sapiens

<400> SEQUENCE: 18

Glu Ile Ser Asp Asp Glu Ala Glu Glu Lys Gly Glu Lys Glu Glu
1               5                   10                  15

Glu Asp Lys Asp Asp Glu Glu Lys Pro Lys
            20                  25

<210> SEQ ID NO 19
<211> LENGTH: 21
<212> TYPE: PRT
<213> ORGANISM: Homo sapiens

<400> SEQUENCE: 19

Ala Ala Leu Asp Ala Leu Asn Thr Asp Asp Glu Asn Asp Glu Glu Glu
1               5                   10                  15

Tyr Glu Ala Trp Lys
            20
```